(12) United States Patent
Eldar-Finkelman et al.

(10) Patent No.: US 8,088,941 B2
(45) Date of Patent: Jan. 3, 2012

(54) GLYCOGEN SYNTHASE KINASE-3 INHIBITORS

(75) Inventors: Hagit Eldar-Finkelman, Shoham (IL); Moshe Portnoy, Givat Shmuel (IL)

(73) Assignee: Tel Aviv University Future Technology Development L.P., Tel-Aviv (IL)

( * ) Notice: Subject to any disclaimer, the term of this patent is extended or adjusted under 35 U.S.C. 154(b) by 0 days.

(21) Appl. No.: 12/149,336

(22) Filed: Apr. 30, 2008

(65) Prior Publication Data

US 2008/0312188 A1 Dec. 18, 2008

Related U.S. Application Data

(60) Continuation of application No. 11/280,209, filed on Nov. 17, 2005, now Pat. No. 7,378,432, which is a continuation-in-part of application No. PCT/IL2004/000570, filed on Jun. 27, 2004, and a continuation-in-part of application No. 10/810,578, filed on Mar. 29, 2004, now Pat. No. 7,157,422, which is a division of application No. 09/951,902, filed on Sep. 14, 2001, now Pat. No. 6,780,625.

(60) Provisional application No. 60/628,542, filed on Nov. 18, 2004, provisional application No. 60/482,719, filed on Jun. 27, 2003, provisional application No. 60/528,495, filed on Dec. 11, 2003.

(51) Int. Cl.
*C07F 9/02* (2006.01)
*A61K 31/155* (2006.01)

(52) U.S. Cl. .......................... 558/70; 514/634

(58) Field of Classification Search .................. 558/70; 514/634
See application file for complete search history.

(56) References Cited

U.S. PATENT DOCUMENTS

| | | | |
|---|---|---|---|
| 1,471,621 A | 10/1923 | McCord | |
| 2,046,068 A | 6/1936 | Gray | |
| 3,193,159 A | 7/1965 | Swindler | |
| 4,186,646 A | 2/1980 | Martin | |
| 5,462,101 A | 10/1995 | Mouchmouchian | |
| 5,749,925 A | 5/1998 | Bocker et al. | |
| 5,861,266 A | 1/1999 | Ullrich et al. | |
| 6,057,117 A | 5/2000 | Harrison et al. | |
| 6,153,618 A | 11/2000 | Schultz et al. | |
| 6,326,174 B1 | 12/2001 | Joyce et al. | |
| 6,441,140 B1 | 8/2002 | Comb et al. | |
| 6,495,376 B1 | 12/2002 | Lu et al. | |
| 6,780,625 B2 | 8/2004 | Eldar-Finkelman | |
| 6,982,318 B1 | 1/2006 | Comb et al. | |
| 7,157,422 B2 | 1/2007 | Eldar-Finkelman | |
| 7,348,308 B2 | 3/2008 | Eldar | |
| 7,378,432 B2 | 5/2008 | Eldar et al. | |
| 7,446,092 B2 | 11/2008 | Eldar | |
| 2002/0147146 A1 | 10/2002 | Eldar-Finkelman | |
| 2004/0162234 A1 | 8/2004 | Eldar-Finkelman | |
| 2006/0069066 A1 | 3/2006 | Eldar-Finkelman et al. | |
| 2006/0135408 A1 | 6/2006 | Eldar-Finkelman | |
| 2007/0072791 A1 | 3/2007 | Eldar-Finkelman | |
| 2007/0196883 A1 | 8/2007 | Alessi et al. | |
| 2009/0062180 A1 | 3/2009 | Eldar | |

FOREIGN PATENT DOCUMENTS

| | | |
|---|---|---|
| EP | 1413593 | 4/2004 |
| GB | 781806 | 8/1957 |
| GB | 785457 | 10/1957 |
| JP | 49-125510 | 12/1974 |
| JP | 57-212704 | 12/1982 |
| JP | 58-071937 | 4/1983 |
| JP | 63-250063 | 10/1988 |
| WO | WO 95/01376 | 1/1995 |
| WO | WO 97/33601 | 9/1997 |
| WO | WO 97/41854 | 11/1997 |
| WO | WO 98/05961 | 2/1998 |
| WO | WO 98/16528 | 4/1998 |
| WO | WO 00/45237 | 8/2000 |
| WO | WO 00/59206 | 10/2000 |
| WO | WO 00/74663 | 12/2000 |
| WO | WO 01/49709 | 7/2001 |
| WO | WO 02/16318 | 2/2002 |
| WO | WO 02/24941 | 3/2002 |
| WO | WO 03/008479 | 1/2003 |
| WO | WO 2004/052404 | 6/2004 |
| WO | WO 2004/052414 | 6/2004 |
| WO | WO 2005/000192 | 1/2005 |
| WO | WO 2006/054298 | 5/2006 |

OTHER PUBLICATIONS

Kubinyi, 3D QSAR in Drug Design: Ligand-Protein Interactions and Molecular Similarity, vol. 2-3, Springer, 1998, 800 pages.*
Luduena et al. (CAPLUS Abstract of Archives Internationales de Pharmacodynamie et de Therapie (1955), 101, 17-37).*
Kubinyi (3D QSAR in Drug Design: Ligand-Protein Interactions and Molecular Similarity, vol. 2-3, Springer, 1998, 800 pages) TOC and p. 243 provided.*
Harms et al. (CAPLUS Abstract of DE 4402189).*
Harms et al. (CAPLUS Abstract of DE 4402189, published Jul. 27, 1995).*
Chen et al. "The Mood-Stbilizing Agent Valproate Inhibits the Activity of Glycogen Synthase Kinase-3", Journal of Neurochemistry, 72: 1327-1330, 1999. Cheng et al. "'Insulin-Like' Effects of Lithium Ion on Isolated Rat Adipocytes. II. Specific Activation of Glycogen Synthase", Molecular & Cellular Biochemistry, 56(2): 183-189, 1983. Abstract.
Coghlan et al. "Selective Small Molecule Inhibitors of Glycogen Synthase Kinase-3 Modulate Glycogen Metabolism and Gene Transcription", Chemistry & Biology, 7: 793-803, 2000.
Cross et al. "The Inhibition of Glycogen Synthase Kinase-3 by Insulin or Insulin-Like Growth Factor 1 in the Rat Skeletal Muscle Cell Line L6 is Blocked by Wortmannin, But Not by Rapamycin: Evidence That Wortmannin Blocks Activation of the Mitogen-Activated Protein Kinase Pathway in L6 Cells Between Ras and Raf", Biochemical Journal, 303: 21-26, 1994.

(Continued)

Primary Examiner — Robert Havlin

(57) ABSTRACT

Novel compounds designed to allow interactions with binding sites of GSK-3 and hence are capable of inhibiting GSK-3 activity, via inhibition of substrate binding are disclosed. Further disclosed are pharmaceutical compositions including same and methods of using same in the treatment of GSK-3 mediated conditions.

24 Claims, 15 Drawing Sheets

OTHER PUBLICATIONS

Damiens et al. "Anti-Mitotic Properties of Indirubin-3'-Monoxime, A CDK/GSK-3 Inhibitor: Induction of Endoreplication Following Prophase Arrest", Oncogene, 20: 3786-3797, 2001.
Eldar-Finkelman et al. "Glycogen Synthase Kinase 3: An Emerging Therapeutic Target", Trends in Molecular Medicine, 8(3): 126-132, 2002.
Woodgett "Judging a Protein by More Than Its Name: GSK-3", Science's STKE, 100(RE12): 1-11, 2001.
International Preliminary Examination Report Dated Sep. 6, 2005 From the International Preliminary Examining Authority Re.: Application No. PCT/IL03/01057.
Office Action Dated Dec. 12, 2008 From the State Intellectual Property Office of the People's Republic of China Re.: Application No. 200480024017.5.
Office Action Dated Oct. 22, 2008 From the Israeli Patent Office Re.: Application No. 172038.
Official Action Dated Feb. 8, 2008 From the US Patent and Trademark Office Re.: U.S. Appl. No. 10/538,171.
Official Action Dated Apr. 24, 2007 From the US Patent and Trademark Office Re.: U.S. Appl. No. 11/602,406.
International Preliminary Report on Patentability Dated May 31, 2007 From the International Bureau of WIPO Re.: Application No. PCT/IL2005/001218.
Official Action Dated Aug. 2, 2007 From the US Patent and Trademark Office Re.: U.S. Appl. No. 11/280,209.
Official Action Dated Aug. 20, 2007 From the US Patent and Trademark Office Re.: U.S. Appl. No. 10/538,171.
American Diabetes Association "Standards of Medical Care for Patients With Diabetes Mellitus", Diabetes Care, 17(6): 616-623, 1994.
Barber et al. "Insulin Rescues Retinal Neurons From Apoptosis by a Phosphotidylinositol 3-Kinase/Akt-Mediated Mechanism That Reduces the Activation of Caspase-3", The Journal of Biological Chemistry, 276(350): 32814-32821, 2001.
Barrett et al. "Proteinase Inhibitors", Research Monographs in Cell and Tissue Physiology, V-XXII,1986.
Bijur et al. "Glycogen Synthase Kinese-3? Facilities Staurosporine- and Heat-Induced Apotosis", The Journal of Biological Chemistry, 275(11): 7583-7590, 2000.
Burke et al. "Potent Inhibition of Insulin Receptor Dephosphorylation by a Hexamer Peptide Containing the Phosphotyrosyl Mimetic F2Pmp", Biochemical and Biophysical Research Communications, 204(1): 129-134, 1994.
Burke et al. "Small Molecule Interactions With Protein-Tyrosine Phosphatase PTP1B and Their Use in Inhibitor Design", Biochemistry, 35: 15989-15996, 1996.
Chen et al. "Why is Phosphonodifluoromethyl Phenylalanine a More Potent Inhibitory Moiety Than Phosphonomethyl Phenylalaline Towards Protein-Tyrosine Phosphatases?", Biochemical and Biophysical Research Communications, 216(3): 976-984, 1995.
Cheng et al. "Insulin-Like' Effects of Lithium Ion on Isolated Rat Adipocytes L. Stimulation of Glycogenesis Beyond Glucose Transport", Molecular and Cellular Biochemistry, 56: 177-182, 1983.
Chu et al. "Sequential Phosphorylation by Mitogen-Activated Protein Kinase and Glycogen Synthase Kinase 3 Represses Transcriptional Activation by Heat Shock Factor-1", The Journal of Biological Chemistry, 271(48): 30847-30857, 1996.
Correll et al. "Inhibition of GSK3? Mediates Cell Survival in Differentiated PC-12 Cells Undergoing Apoptosis", Society for Neuroscience, 25(2): 1519, 1999. Abstract No. 605.8.
Cross et al. "Inhibition of Glycogen Synthase Kinase-3 by Insulin Mediated by Protein Kinase B", Nature, 378: 785-789, 1995.
Cross et al. "Selective Small-Molecule Inhibitors of Glycogen Synthase Kinase-3 Activity Protect Primary Neurons From Death", Journal of Neurochemistry, 77: 94102, 2001.
Crowder et al. "Glycogen Synthase Kinase-3? Activity is Critical for Neuronal Death Caused by Inhibiting Physpatidylinositol 3-Kinase or Akt But Not for Death Caused by Nerve Growth Factor Withdrawal", The Journal of the Biological Chemistry, 275(44): 34266-34271, 2000.

Dajani et al. "Crystal Structure of Glycogen Synthase Kinase 3?: Structural Basis for Phosphate-Primed Substrate Specificity and Autoinhibition", Cell, 105: 721-732, 2001.
Davies et al. "Specificity and Mechanism of Action of Some Commonly Used Protein Kinase Inhibitors", Biochemical Journal, 351: 95-105, 2000.
Devlin et al. "Textbook of Biochemistry With Clinical Correlation", Wiley-Liss, 4th Ed., XVII-XXV, 1997.
Donella-Deana et al. "Dephosphorylation of Phosphopeptides by Colcineurin (Protein Phosphatase 2B)", European Journal of Biochemistry, 219(1-2): 109-117, 1994. Tab.1, 2.
Dugas et al. "Bioorganic Chemistry of the Amino Acids: Chemical Synthesis of Proteins", Springer Verlag, NY, p. 54-92, 1981.
Eldar-Finkelman et al. "Expression and Characterization of Glycogen Synthase Kinase-3 Mutants and Their Effect on Glycogen Synthase Activity in Intact Cells", Proc. Natl. Acad. Sci. USA, 93(19): 10228-10233, 1996.
Eldar-Finkelman et al. "Increased Glycogen Synthase Kinase-3 Activity in Diabetes- and Obesity-Prone C57BL/6J Mice", Diabetes, 48(8): 1662-1666, 1999.
Eldar-Finkelman et al. "Phosphorylation of Insulin Receptor Substrate 1 by Glycogen Synthase Kinase 3 Impairs Insulin Action", Proc. Natl. Acad. Sci. USA, 94(18): 9660-9664, 1997.
Eldar-Finkleman et al. "The Insulin Mimetic Action of Glycogen Synthase Kinase-3 Inhibitors", Diabetologia, 45(Suppl.2): A 70, 38th Annual Meeting for the European Association for the Study of Diabetes (EASD), Budapest, Hungary, 2002. Abstract.
Fahraeus et al. "Inhibition of PRB Phosphorylation and Cell-Cycle Progression by A 20-Residue Peptide Derived From P16 CDKN2/INK4A", Current Biology, 6(1): 84-91, 1996.
Fiol et al. "A Secondary Phosphorylation of CREB341 at Ser129 is Required for the cAMP-Mediated Control of Gene Expression. A Role for Glycogen Synthase Kinase-3 in the Control of Gene Expression", The Journal of Biological Chemistr, 269(51): 32187-32193, 1994.
Fiol et al. "Formation of Protein Kinase Regognition Sites by Covalent Modification of Substrate. Molecular Mechanism for the Synergistic Action of Casein Kinase II and Glycogen Synthase Kinase 3", The Journal of Biological Chemistry, 262(29): 14042-14048, 1987.
Fiol et al. "Ordered Multisite Protein Phosphorylation. Analysis of Glycogen Synthase. Kinase-3 Action Using Model Peptide Substrates", The Journal of Biological Chemistry, 265(11): 6061-6065, 1990. vol. 2: Abstract.
Fiol et al. "Phosphoserine as A Recognition Determinant for Glycogen Synthase Kinase-3: Phosphorylation of a Synthetic Peptide Based on the G-Component of Protein Phosphatase-1", Archives of Biochemistry and Biophysics, 267(2): 797802, 1988.
Fu et al. "Design and Synthesis of a Pyrodone-Based Phosphtyrosine Mimetic", Bioorganic and Medicinal Chemistry Letters, 8(19): 2813-2816, 1998.
Gao et al. "Inhibition of Grb2 SH2 Domain Binding by Non-Phosphate-Containing Ligands. 2.4-(2-Malonyl)Phenylalanine as a Potent Phosphotyrosyl Mimetic", Journal of Medicinal Chemistry, 43(5): 911-920, 2000.
Gething et al. "Cell-Surface Expression of Influenza Haemagglutinin From a Cloned DNA Copy of the RNA Gene", Nature, 293(5834): 620-625, 1981.
Groves et al. "Structural Basis for Inhibition of the Protein Tyrosine Phosphatase 1B by Phosphotyrosine Peptide Mimetics", Biochemistry, 37(51): 17773-17783, 1998.
Hallstrom et al. "Regulation of Transcription Factor Pdr1p Function by an Hsp70 Protein in *Saccharomyces cerevisiae*", Molecular and Cellular Biology, 18(3): 1147-1155, 1998.
Hanger et al. "Glycogen Synthase Kinase-3 Induces Alzheimers Disease-Like Phosphorylation of Tau: Generation of Paired Helical Filament Epitopes and Neuronal Localisatoin of the Kinase", Neuroscience Letters, 147: 58-62, 1992.
Hawiger "Cellular Import of Functional Peptides to Block Intracellular Signaling", Current Opinion in Immunology, 9(2): 189-194, 1997.
Hawiger "Non-Invasive Intracellular Delivery of Functional Peptides", Current Opinion in Chemical Biology, 3: 89-94, 1999.
He et al. "Glycogen Synthase Kinase-3 and Dorsoventral Patterning in Xenopus Embryos", Nature, 374(6523): 617-622, 1995.

Higashimoto et al. "Human P53 is Phosphorylated on Serines 6 and 9 in Response to DNA Damage-Inducing Agents", The Journal of Biological Chemistry, 275(30): 23199-23203, 2000.

Hotamisligil et al. "IRS-1-Mediated Inhibition of Insulin Receptor Tyrosine Kinase Activity in TNT-?- and Obesity-Induced Insulin Resistance", Science, 271: 665-667, 1996.

Jicha et al. "A Confirmation- and Phosphorylation-Dependent Antibody Recognizing the Paired Helical Filaments of Alzheimer's Disease", Journal of Neurochemistry, 69: 2087-2095, 1997.

Klein et al. "A Molecular Mechanism for the Effect of Lithium on Development", Proc. Natl. Acad. Sci. USA, 93: 8455-8459, 1996.

Kole et al. "Protein-Tyrosine Phosphatase Inhibition by a Peptide Containing the Phosphotyrosyl Mimetic, L-O-Malonyltyrosine", Biochemical and Biophysical Research Communications, 209(3): 817-822, 1995.

Kole et al. "Specific Inhibition of Insulin Receptor Dephosphorylation by a Synthetic Dodecapeptide Containing Sulfotyrosyl Residues as Phosphotyrosyl Mimetic", Indian Journal of Biochemistry & Biophysics, 34(1-2): 50-55, 1997.

Latimer et al. "Stimulation of MAP Kinase by V-Raf Transformation of Fibroblasts Fails to Induce Hyperphosphorylation of Transfected Tau", FEBS Letters, 365: 42-46, 1995.

Leclerc et al. "Indirubins Inhibit Glycogen Synthase Kinase-3? and CDK5/P25, Two Proteins Kinases Involved in Abnormal Tau Phosphorylation in Alzheimer's Disease", The Journal of Biological Chemistry, 276(1): 251-260, 2001.

Lovestone et al. "Alzheimer's Disease-Like Phosphorylation of the Microtubule-Associated Protein Tau by Glycogen Synthase Kinase-3 in Transfected Mammalian Cells", Current Biology, 4: 1077-1086, 1995.

Lucas et al. "Decreased Nuclear Beta-Catenin, Tahyperphosphorylation and Neurodegeneration in GSK-3Beta Conditional Transgenic Mice", The EMBO Journal, 20:27-39, 2001.

Mandelkow et al. "Glycogen Synthase Kinase-3 and the Alzheimer-Like State of Micortubule-Associated Protein Tau", FEBS Letters, 314: 315-321, 1992.

Mandelkow et al. "Tau as a Marker for Alzheimer's Disease", Trends in Biochemical Sciences, 18(12): 480-483, 1983.

Manenti et al. "Affinity Purification and Characterization of Myristoylated Alaninerich Protein Kinase C Substrate (MARCKS) From Bovine Brain. Comparison of the Cytoplasmic and the Membrane-Bound Forms", The Journal of Biological Chemistry, 267(31): 22310-22315, 1992.

Maniatis "Signal Transduction: Catalysis by a Multiprotein IkB Kinase Complex", Science, 278(5339): 818, 1997. Extract.

Manji et al. "Lithium at 50: Have the Neuroprotective Effects of This Unique Cation Been Overlooked?", Biological Psychiatry, 46(7): 929-940, 1999.

McKinsey et al. "Phosphorylation of the PEST Domain of IkappaB-beta Regulates the Function of NF-KappaB/IkappaBbeta Complexes", The Journal of Biological Chemistry, 272(36): 22377-22380, 1997.

Merrifield et al. "Solid Phase Peptide Synthesis. I. The Synthesis of a Tetrapeptide", Journal of the American Chemical Society, 85: 2149-2154, 1963.

Mikol et al. "The Crystal Structures of the SH2 Domain of P56Ick Complexed With Two Phosphonopeptides Suggest a Gated Peptide Binding Site", Journal of Molecular Biology, 246(2): 344-355, 1995.

Mitchell et al. "Heat-Stable Inhibitor Protein Derived Peptide Substrate Analogs: Phosphorylation by cAMP-Dependent and cGMP-Dependent Protein Kinases", The American Chemical Society, 1994.

Moreno et al. "Glycogen Synthase Kinase 3 Phosphorylation of Different Residues in the Presence of Different Factors: Analysis on TAU Protein", Molecular and Cellular Biochemistry, 165(1):47-54, 1996. Tab.1.

Morrison et al. "Organic Chemistry", Allyn and Bacon, 5th Ed., V-XXIV,1987.

Mulot et al. "Phosphorylation of Tau by Glycogen Synthase Kinase-3 Beta In Vitro Produces Species With Similar Electrophoretic and Immunogenic Properties to PHF-Tau From Alzheimer's Disease Brain", Biochemical Society Transactions, 23(1): 45S, 1995.

Myers et al. "IRS-1 Activates Phosphatidylinositol 3'-Kinase by Associating With SRC Homology 2 Domains of P85D", Proc. Natl. Acad. Sci. USA, 89(21): 10350-10354, 1992.

Nikoulina et al. "Potential Role of Glycogen Synthase Kinase-3 in Skeletal Muscle Insulin Resitance of Type 2 Diabetes", Diabetes, 49(2): 263-271, 2000.

Nikoulina et al. "Regulation of Glycogen Synthase Activity in Cultured Skeletal Muscle Cells From Subjects With Type II Diabetes: Role of Chronic Hyperinsulinemia and Hyperglycemia", Diabetes, 46(6): 1017-1024, 1997.

Nonaka et al. "Chronic Lithium Treatment Robustly Protects Neurons in the Central Nervous System Against Excitotoxicity by Inhibiting N-Methyl-D-Aspartate Rectpro-Mediated Calcium Influx", Proc. Natl. Acad. Sci. USA, 95: 2642-2647, 1998.

Oelrichs et al. "Unique Toxic Peptides Isolated From Sawfly Larvae in Three Continents", Toxicon, 37(3): 537-544, 1999. Fig.3.

Otaka et al. "Synthesis and Application of N-Box-L-2-Amino-4-(Diethylphosphono)-4-,4-Difluorobutanoic Acid for Solid-Phase Synthesis of Nonhydrolyzable Phosphoserine Peptide Analogues", Tetrahedron Letters, 36(6): 927-930, 1995.

Othaka et al. "Development of New Methodology for the Synthesis of Functionalized ?—Fluorophosphonates and Its Practical Application to the Preparation of Phosphopeptide Mimetics", Chemical Communications, 12: 1081-1082, 2000.

Pap et al. "Role of Glycogen Synthase Kinase-3 in the Phosphatidylinositol 3-Kinase/Akt Cell Survival Pathway", The Journal of Biological Chemistry, 273: 19929-19932, 1998.

Phiel "Molecular Targets of Lithium Action", Annual Reviews in Pharmacological Toxicology, 41: 789-813, 2001.

Plotkin et al. "Insulin Mimetic Action of Synthetic Phosphorylated Peptide Inhibitors of Glycogen Synthase Kinase-3", Journal of Pharmacology and Experimental Therapeutics, 305(3): 974-980, 2003.

Roller et al. "Potent Inhibition of Protein-Tyrosine Phosphatase-1B Using the Phosphotyrosyl Mimetic Fluoro-O-Malonyl Tyrosine (FOMT)", Bioorganics and Medicinal Chemistry Letters, 8(16): 2149-2150, 1998.

Rubinfeld et al. "Binding of GSK3Beta to the APC-Beta-Catenin Complex and Regulation of Complex Assembly", Science, 272(5264): 1023-1026, 1996.

Sambrook et al. "Molecular Cloning: A Laboratory Manual", Cold Spring Harbour Press, 2nd Ed., V-XXXII,1989.

Schiller et al. "Synthesis for Side-Chain Cyclized Peptide Analogs on Solid Supports", International Journal of Peptide Protein Research, 25: 171-177, 1985.

Shapiro et al. "Combined Fmoc-Alloc Strategy for A General SPPS of Phosphoserine Peptides: Preparation of Phosphorylation-Dependent Tau Antisera", Bioorganics and Medicinal Chemistry, 5(1): 147-156, 1997.

Sherman et al. "Compatibility of Thioamides With Reverse Turn Features: Synthesis and Conformational Analysis of Two Model Cyclic Pseudopeptides Containing Thioamides as Backbone Modifications", Journal of the American Chemical Society, 112: 433-441, 1990.

Shulman et al. "Quantitation of Muscle Glycogen Synthesis in Normal Subjects and Subjects With Non-Insulin-Dependent Diabetes by 13C Nuclear Magnetic Resonance Spectroscopy", New England Journal of Medicine, 322(4): 223-228, 1990.

Stambolic et al. "Lithium Inhibits Glycogen Synthase Kinase-3 Activity and Mimics Wingless Signalling in Intact Cells", Current Biology, 6: 1664-1668, 1996.

Taniguchi et al. Myristoylated Alanine-Rich C Kinase Substrate (MARCKS), A Major Protein Kinase C Substrate, is an In Vivo Substrate of Proline-Directed Protein Kinase(s), The Journal of Biological Chemistry, 269(28): 18299-18302, 1994.

Tanti et al. "Serine/Threonine Phosphorylation of Insulin Receptor Substrate 1 Modulates Insulin Receptor Signaling", The Journal of Biological Chemistry, 269(8): 6051-6057, 1994.

Ter Haar et al. "Structure of GSK-3 Beta Reveals a Primed Phosphorylation Mechanism", Nature Structural Biology, 8(7): 593-596, 2001.

Thomas "Excitatory Amino Acids in Health and Disease", Journal of the American Geriatric Society, 43: 1279-1289, 1995.

Thorsett et al. "Dipeptide Mimics. Conformationally Restricted Inhibitors of Angiotensin-Converting Enzyme", Biochemical and Biophysical Research Communications, 111(1): 166-171, 1983.

Tong et al. "Activation of Glycogen Synthase Kinase-3 Beta (GSK-3 Beta) by Platelet Activating Factor Mediates Migration and Cell Death in Cerebellar Granule Neurons", European Journal of Neuroscience, 13: 1913-1922, 2001.

Veber et al. "Conformationally Restricted Bicyclic Analogs of Somatostatin", Proc. Natl. Acad. Sci. USA, 75(6): 2636-2640, 1978.

Welsh et al. "Glycogen Synthase Kinase-3 is Rapidly Inactivated in Response to Insulin and Phosphorylates Eukaryotic Initiation Factor Eif-2B", Biochemical Journal, 294(Pt 3): 625-629, 1993.

Wiemann et al. "Synthesis of Suitably Protected Hydroxymethylene Phosphonate- and 'Phosphat Phosphonate'-Analogues of Phosphoserine and Their Incorporation Into Synthetic Peptides", Tetrahedron, 56: 1331-1337, 2000.

Communication Pursuant to Article 94(3) EPC Dated Feb. 18, 2010 From the European Patent Office Re.: Application No. 03777156.5.

Office Action Dated Nov. 13, 2009 From the State Intellectual Property Office of the People's Republic of China Re.: Application No. 200580045212.0 and Its Translation Into English.

Official Action Dated Feb. 23, 2010 From the US Patent and Trademark Office Re.: U.S. Appl. No. 12/155,087.

Response Dated Mar. 11, 2010 to Office Action of Nov. 13, 2009 From the State Intellectual Property Office of the People's Republic of China Re.: Application No. 200580045212.0.

Response Dated Dec. 28, 2009 to Official Action of Nov. 30, 2009 From the US Patent and Trademark Office Re.: U.S. Appl. No. 12/155,087.

Official Action Dated Nov. 30, 2009 From the US Patent and Trademark Office Re.: U.S. Appl. No. 12/155,087.

Office Action Dated Dec. 17, 2008 From the Israeli Patent Office Re.: Application No. 168983 and Its Translation Into English.

Response Dated May 11, 2010 to Decision of Rejection of Feb. 12, 2010 From the State Intellectual Property Office of the People's Republic of China Re.: Application No. 200480024017.5.

Response Dated Jun. 22, 2010 to Official Action of Feb. 23, 2010 From the US Patent and Trademark Office Re.: U.S. Appl. No. 12/155,087.

Response Dated Jul. 11, 2010 to Communication Pursuant to Article 94(3) EPC of Mar. 11, 2010 From the European Patent Office Re.: Application No. 04744910.3.

Translation of Notice of Reason for Rejection Dated Jul. 13, 2010 From the Japanese Patent Office Re. Application No. 2005-502348.

Notice of Allowance Dated Jul. 26, 2010 From the US Patent and Trademark Office Re.: U.S. Appl. No. 12/155,087.

Response Dated Jun. 23, 2010 to Communication Pursuant to Article 94(3) EPC of Feb. 18, 2010 From the European Patent Office Re.: Application No. 03777156.5.

Office Action Dated Feb. 28, 2010 From the Israeli Patent Office Re.: Application No. 168983 and Its Translation Into English.

Translation of Decision of Rejection Dated Feb. 12, 2010 From the State Intellectual Property Office of the People's Republic of China Re.: Application No. 200480024017.5.

Communication Pursuant to Article 94(3) EPC Dated Mar. 11, 2010 From the European Patent Office Re.: Application No. 04744910.3.

Communication Pursuant to Article 94(3) EPC Dated Feb. 27, 2009 From the European Patent Office Re.: Application No. 05809234.7.

International Search Report and the Written Opinion Dated May 12, 2006 From the International Searching Authority Re.: Application No. PCT/IL2005/001218.

Notice of Allowance Dated Nov. 20, 2007 From the US Patent and Trademark Office Re.: U.S. Appl. No. 10/602,406.

Office Action Dated Jan. 10, 2011 From the Israeli Patent Office Re.: Application No. 172038 and Its Translation Into English.

Official Action Dated Mar. 15, 2006 From the US Patent and Trademark Office Re.: U.S. Appl. No. 10/810,578.

Official Action Dated Apr. 17, 2007 From the US Patent and Trademark Office Re.: U.S. Appl. No. 11/280,209.

Translation of Notice of the Reason for Rejection Dated Jan. 6, 2011 From the Korean Intellectual Property Office Re. Application No. 2005-7010710.

Fischer et al. "Cellular Delivery of Impermeable Effector Molecules in the Form of Conjugates With Peptides Capable of Mediating Membrane Translocation", Bioconjugate Chemistry, 12(6): 825-841, Nov./Dec. 2001.

Translation of Reason for Rejection Dated Mar. 1, 2011 From the Japanese Patent Office Re. Application No. 2006-516816.

Florentiev et al. "Synthesis and Physiocochemical and Coenzyme Properties of Alkyl-Substituted Analogs of the B6 Vitamins and Pyridoxal Phosphate", Methods in Enzymology, 18(Pt.A): 567-598, 1970.

Murakami et al. "Solvolysis of Organic Phosphates. Part IX. Structure-Reactivity Correlations for the Hydrolysis of Organic Orthophosphate Monoesters", Journal of the Chemical Society Perkin Transactions 2: Physical Organic Chemistry, 9: 1235-1241, 1973.

Pieper et al. "3-Deoxy-3-Fluoropyridoxamine 5'-Phosphate: Synthesis and Chemical and Biological Properties of a Coenzyme B6 Analog", Journal of the American Chemical Society, 119(8): 1809-1817, 1997.

Zherdev et al. "Pharmacokinetic Profile and Metabolism of 2-Ethyl-6-Methyl-3-Hydroxypyridine in Rats", Annali dell'Instituto Superiore die Sanita, 24(3): 467-473, 1988.

Burke et al. "4'-O[2(2-Fluoromalonyl)]-L-Tyrosine: A Phosphotyrosyl Mimic for the Preparation of Signal Transduction Inhabitory Peptides", Journal of Medicinal Chemistry, 39: 1021-1027, 1996.

Chen et al. "The Mood-Stabilizing Agent Valproate Inhibits the Activity of Glycogen Synthase Kinase-3", Journal of Neurochemistry, 72: 1327-1330, 1999.

Eldar-Finkleman et al. "The Insulin Mimetic Action of Glycogen Synthase Kinase-3 Inhibitors", Diabetologia, 45(Suppl.2): A 70, Abstract 205, 2002. 38th Annual Meeting for the European Association for the Study of Diabetes (EASD), Budapest, Hungary, 2002.

Hallstrom et al. "Regulation of Transcription Factor Pdr1p Function by An Hsp70 Protein in *Saccharomyces cerevisiae*", Molecular and Cellular Biology, 18(3): 1147-1155,1998.

Mulot et al. "PHF-Tau From Alzheimer's Brain Comprises Four Species on SDS-PAGE Which Can Be Mimicked by In Vitro Phosphorylation of Human Brain Tau by Glycogen Synthase Kinase-3 Beta", FEBS Letters, 349(3): 359-364, 1994.

Stambolieva et al. "Analogues of Vitamin B6. Synthesis and Properties of 3-Deoxypyridoxal Phosphate and 3-O-Methylpyridoxal Phosphate", Tetradedron, 26(13): 3083-3090, 1970.

Ye et al. "L-O-(2-Malonyl)Tyrosine: A New Phosphotyrosyl Mimetic for the Preparation of Src Homology 2 Domain Inhibitory Peptides", Journal of Medicinal Chemistry, 38(21): 4270-4275, 1995.

Zherdev et al. "Pharmacokinetic Profile and Metabolism of 2-Ethyl-6-Methyl-3-Hydroxypyridine in Rats", Annali dell'Instituto Superiore die Sanita, 24(3): 467-473, 1988.

Response Dated May 11, 2011 to Office Action of Jan. 10, 2011 From the Israeli Patent Office Re.: Application No. 172038.

Reexamination Decision (Decision No. 33055) Dated Jun. 17, 2011 From the Patent Reexamination Board of the State intellectual Property Office of the People's Republic of China Re.: Application No. 200480024017.5 and Its Translation Into English.

Translation of Office Action Dated Jun. 30, 2011 From the State Intellectual Property Office of the People's Republic of China Re.: Application No. 200580045212.0.

\* cited by examiner

Figure 1a
Figure 1b
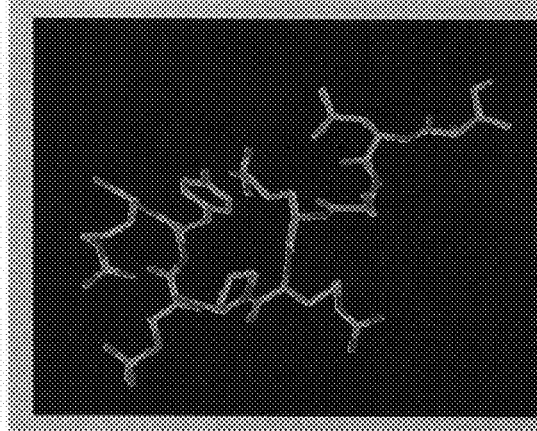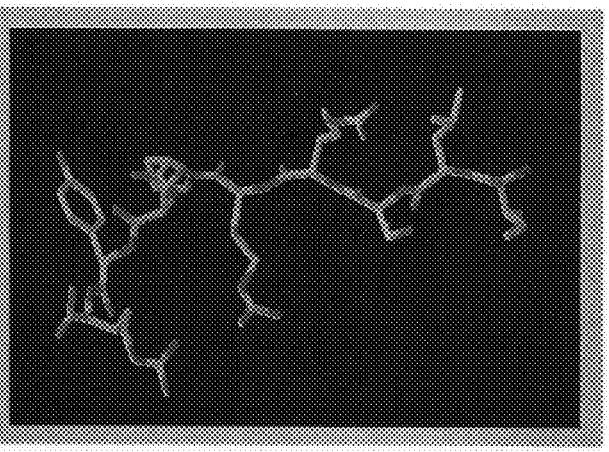
Figure 2
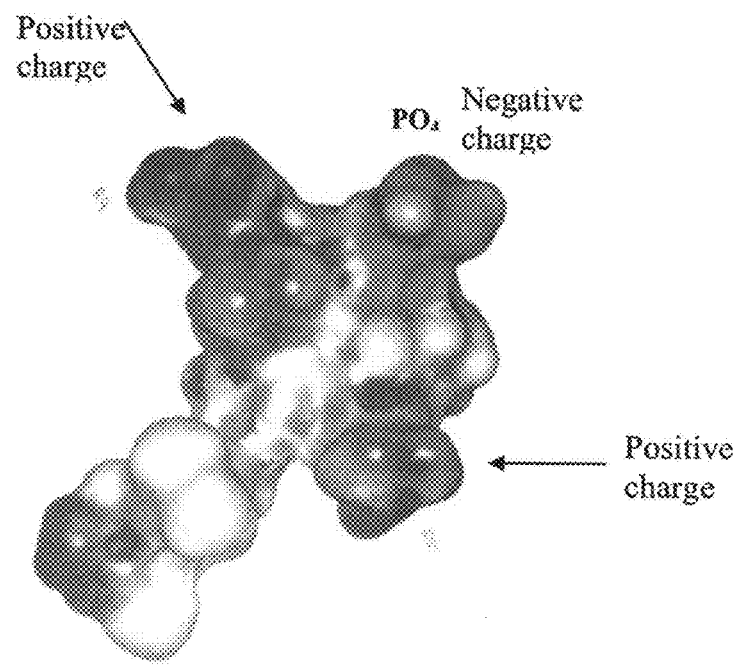

Phenyl Phosphate    Pyridoxal Phosphate (P-5-P)

GSC-2    GSC-1    GSC-3

GSC-5    GSC-4    GSC-21

GSC-6

GSC-7

GSC-8

GSC-9

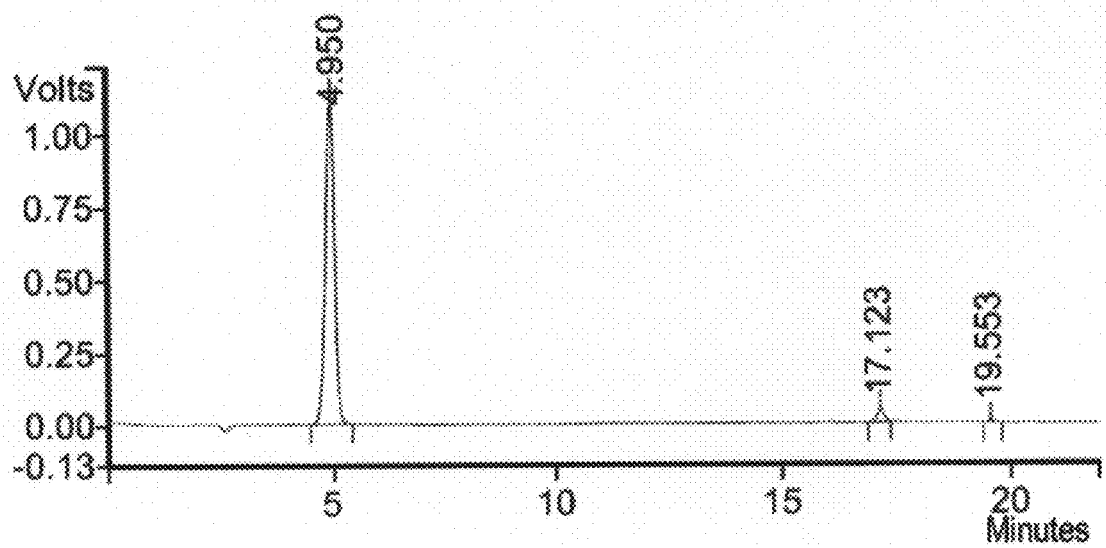

Figure 7a
Figure 7b
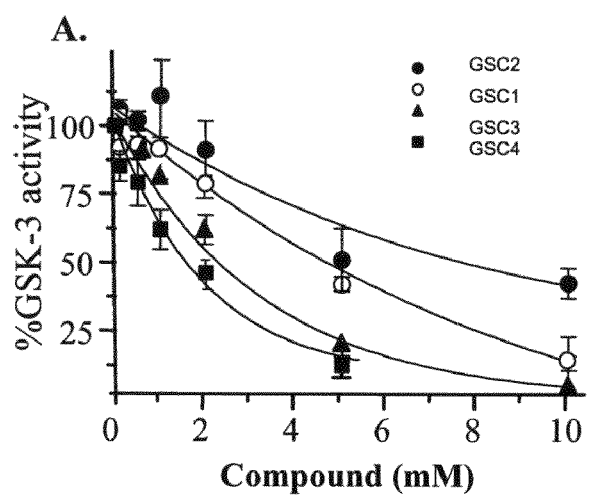
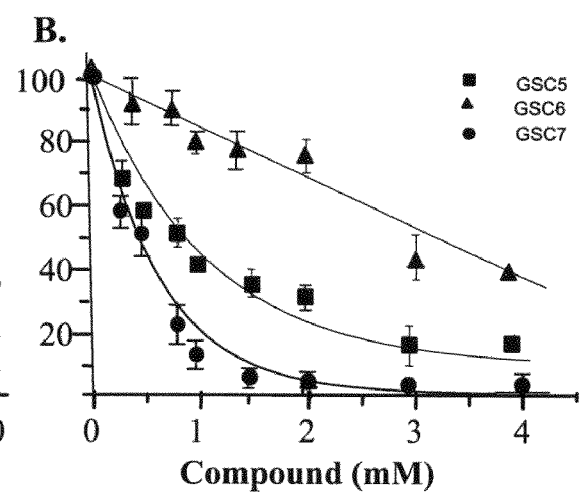

**3-Gua-3-Phos (*MP1*)**

3-gua-4-Phos (*MP5*)

4-Gua-4-Phos (*MP2*)

4-Gua-3-Phos (*MP4*)

2-Gua-3-Phos (*MP3*)

2-Gua-4-Phos (*MP6*)

GLYCOGEN SYNTHASE KINASE-3 INHIBITORS

RELATED APPLICATIONS

This Application is a Continuation of U.S. patent application Ser. No. 11/280,209 filed on Nov.17, 2005 which is a Continuation-In-Part (CIP) of PCT Patent Application No. PCT/IL2004/000570, filed on Jun. 27 2004, which claims priority from U.S. Provisional Application No. 60/482,719, filed on Jun. 27, 2003 and U.S. Provisional Application No. 60/528,495, filed on Dec. 11, 2003. This is also a Continuation-In-Part (CIP) of U.S. patent application Ser. No. 10/810,578, filed on Mar. 29, 2004, now U.S. Pat. No. 7,157,422 issued on Jan. 2, 2007, which is a Divisional of U.S. patent application Ser. No. 09/951,902, filed on Sep. 14, 2001, now U.S. Pat. No. 6,780,625, issued on Aug. 24, 2004. This application also claims priority from U.S. Provisional Patent Application No. 60/628,542, filed on Nov. 18, 2004.

FIELD AND BACKGROUND OF THE INVENTION

The present invention relates to novel compounds for inhibiting glycogen synthase kinase-3 (GSK-3) and their use in regulating biological conditions mediated by GSK-3 activity and, more particularly, to the use of these compounds in the treatment of biological conditions such as type II diabetes, neurodegenerative disorders and diseases and affective disorders.

Protein kinases, the enzymes that phosphorylate protein substrates, are key players in the signaling of extracellular events to the cytoplasm and the nucleus, and take part in practically any event relating to the life and death of cells, including mitosis, differentiation and apoptosis. As such, protein kinases have long been favorable drug targets. However, since the activity of protein kinases is crucial to the well being of the cell, while their inhibition oftentimes leads to cell death, their use as drug targets is limited. Although cell death is a desirable effect for anticancer drugs, it is a major drawback for most other therapeutics.

Glycogen synthase kinase-3 (GSK-3), a member of the protein kinases family, is a cytoplasmic proline-directed serine-threonine kinase that is involved in insulin signaling and metabolic regulation, as well as in Wnt signaling and the scheme of cell fate during embryonic development. Two similar isoforms of the enzyme, termed GSK-3α and GSK-3β, have been identified.

GSK-3 has long been considered as a favorable drug target among the protein kinase family since unlike other protein kinases, which are typically activated by signaling pathways, GSK-3 is normally activated in resting cells, and its activity is attenuated by the activation of certain signaling pathways such as those generated by the binding of insulin to its cell-surface receptor. Activation of the insulin receptor leads to the activation of protein kinase B (PKB, also called Akt), which in turn phosphorylates GSK-3, thereby inactivating it. The inhibition of GSK-3 presumably leads to the activation of glycogen synthesis. The intricate insulin-signaling pathway is further complicated by negative-feedback regulation of insulin signaling by GSK-3 itself, which phosphorylates insulin-receptor substrate-1 on serine residues (Eldar-Finkelman et al., 1997).

Therefore, synthetic GSK-3 inhibitors might mimic the action of certain hormones and growth factors, such as insulin, which use the GSK-3 pathway. In certain pathological situations, this scheme might permit the bypassing of a defective receptor, or another faulty component of the signaling machinery, such that the biological signal will take effect even when some upstream players of the signaling cascade are at fault, as in non-insulin-dependent type II diabetes.

The regulation of glycogen catabolism in cells is a critical biological function that involves a complex array of signaling elements, including the hormone insulin. Through a variety of mediators, insulin exerts its regulatory effect by increasing the synthesis of glycogen by glycogen synthase (GS). A key event in insulin action is the phosphorylation of insulin receptor substrates (IRS-1, IRS-2) on multiple-tyrosine residues, which results in simultaneous activation of several signaling components, including PI3 kinase (Myers et al, 1992)). Similarly, the activity of glycogen synthase is suppressed by its phosphorylation. There is a marked decrease in glycogen synthase activity and in glycogen levels in muscle of type II diabetes patients (Shulman et al., 1990).

One of the earliest changes associated with the onset of type II (non-insulin dependent) diabetes is insulin resistance. Insulin resistance is characterized by hyperinsulemia and hyperglycemia. Although the precise molecular mechanism underlying insulin resistance is unknown, defects in downstream components of the insulin signaling pathway are considered to be the cause.

Glycogen synthase kinase-3 (GSK-3) is one of the downstream components of insulin signaling. It was found that high activity of GSK-3 impairs insulin action in intact cells, by phosphorylating the insulin receptor substrate-1 (IRS-1) serine residues (Eldar-Finkelman et al, 1997), and likewise, that increased GSK-3 activity expressed in cells results in suppression of glycogen synthase activity (Eldar-Finkelman et al, 1996). Further studies conducted in this respect uncovered that GSK-3 activity is significantly increased in epididymal fat tissue of diabetic mice (Eldar-Finkelman et al, 1999). Subsequently, increased GSK-3 activity was detected in skeletal muscle of type II diabetes patients (Nickoulina et al, 2000). Additional recent studies further established the role of GSK-3 in glycogen metabolism and insulin signaling (for review see, Eldar-Finkelman, 2002 Woodgett, 2001), thereby suggesting that the inhibition of GSK-3 activity may represent a way to increase insulin activity in vivo.

GSK-3 is also considered to be an important player in the pathogenesis of Alzheimer's disease. GSK-3 was identified as one of the kinases that phosphorylate tau, a microtubule-associated protein, which is responsible for the formation of paired helical filaments (PHF), an early characteristic of Alzheimer's disease. Apparently, abnormal hyperphosphorylation of tau is the cause for destabilization of microtubules and PHF formation. Despite the fact that several protein kinases were shown to promote phosphorylation of tau, it was found that only GSK-3 phosphorylation directly affected tau ability to promote microtubule self-assembly (Mandelkow et al., 1992; Mulot et al., 1995). Further evidence for the GSK-3 role in this respect came from studies of cells overexpressing GSK-3 and from transgenic mice that specifically expressed GSK-3 in brain. In both cases GSK-3 led to generation of the PHF like epitope tau (Lucas et al., 2001).

GSK-3 is further linked with Alzheimer's disease by its role in cell apoptosis. The fact that insulin is a survival factor of neurons and initiates its anti-apoptotic action through activation of PI3 kinase and PKB, suggested that GSK-3, which is negatively regulated by these signaling components, promotes neuronal apoptosis. Several studies have indeed confirmed this view, and showed that GSK-3 is critically important in life and death decision. Furthermore, its apoptotic function was shown to be independent of PI3 kinase. Overexpression of GSK-3 in PC12 cells caused apoptosis (Pap et al., 1998). Activation of GSK-3 in cerebellar granule neurons mediated migration and cell death (Tong et al., 2001). In human neuroblastoma SH-SY5Y cells, over expression of GSK-3 facilitated stauroaporine-induced cell apoptosis (Bijur et al., 2000).

The relation between GSK-3 inhibition and the prevention of cells death has been further demonstrated by studies showing that expression of Frat1, a GSK-3 β inhibitor, was sufficient to rescue neurons from death induced by inhibition of PI3 kinase (Crowder et al., 2000).

Another implication of GSK-3 was detected in the context of affective disorders, i.e., bipolar disorders and manic depression. This linkage was based on the findings that lithium, a primary mood stabilizer frequently used in bipolar disease, is a strong and specific inhibitor of GSK-3 at the therapeutic concentration range used in clinics (Klein et al., 1996; Stambolic et al., 1996; Phiel et al., 2001). This discovery has led to a series of studies that were undertaken to determine if lithium could mimic loss of GSK-3 activity in cellular processes. Indeed, lithium was shown to cause activation of glycogen synthesis (Cheng et al., 1983), stabilization and accumulation of β-catenin (Stambolic et al., 1996), induction of axis duplication in *Xenopus* embryo (Klein et al., 1996), and protection of neuronal death (Bijur et al., 2000). Valproic acid, another commonly used mood stabilizer has also been found to be an effective GSK-3 inhibitor (Chen et al., 1999). Altogether, these studies indicated that GSK-3 is a major in vivo target of lithium and valproic acid and thus has important implications in novel therapeutic treatment of affective disorders.

One mechanism by which lithium and other GSK-3 inhibitors may act to treat bipolar disorder is to increase the survival of neurons subjected to aberrantly high levels of excitation induced by the neurotransmitter, glutamate (Nonaka et al., 1998). Glutamate-induced neuronal excitotoxicity is also believed to be a major cause of neurodegeneration associated with acute damage, such as in cerebral ischemia, traumatic brain injury and bacterial infection. Furthermore, it is believed that excessive glutamate signaling is a factor in the chronic neuronal damage seen in diseases such as Alzheimer's, Huntington's, Parkinson's, AIDS associated dementia, amyotrophic lateral sclerosis (AML) and multiple sclerosis (MS) (Thomas, 1995).

Consequently, GSK-3 inhibitors are believed to be a useful treatment in these and other neurodegenerative disorders. Indeed, dysregulation of GSK-3 activity has been recently implicated in several CNS disorders and neurodegenerative diseases, including schizophrenia (Beasley et al., 2001), stroke, and Alzheimer's disease (AD) (Bhat and Budd, 2002; Lucas et al., 2001; Mandelkow et al., 1992).

In view of the wide implication of GSK-3 in various signaling pathways, development of specific inhibitors for GSK-3 is considered both promising and important regarding various therapeutic interventions as well as basic research.

As is mentioned above, some mood stabilizers were found to inhibit GSK-3. However, while the inhibition of GSK-3 both by lithium chloride (LiCl) (PCT International patent application WO 97/41854) and by purine inhibitors (PCT International patent application WO 98/16528) has been reported, these inhibitors are not specific for GSK-3. In fact, it was shown that these drugs affect multiple signaling pathways, and inhibit other cellular targets, such as inositol monophosphatase (IMpase) and histone deacetylases (Berridge et al., 1989).

Similarly, an engineered cAMP response element binding protein (CREB), a known substrate of GSK-3, has been described (Fiol et al, 1994), along with other potential GSK-3 peptide inhibitors (Fiol et al, 1990). However, these substrates also only nominally inhibit GSK-3 activity.

Other GSK-3 inhibitors were recently reported. Two structurally related small molecules SB-216763 and SB-415286 (Glaxo SmithKline Pharmaceutical) that specifically inhibited GSK-3 were developed and were shown to modulate glycogen metabolism and gene transcription as well as to protect against neuronal death induced by reduction in PI3 kinase activity (Cross et al., 2001; Coghlan et al., 2000). Another study indicated that Induribin, the active ingredient of the traditional Chinese medicine for chronic myelocytic leukemia, is a GSK-3 inhibitor. However, Indirubin also inhibits cyclic-dependent protein kinase-2 (CDK-2) (Damiens et al., 2001). These GSK-3 inhibitors are ATP competitive and were identified by high throughput screening of chemical libraries. It is generally accepted that a major drawback of ATP-competitive inhibitors is their limited specificity (Davies et al., 2000).

A general strategy for developing specific peptide and other GSK-3 inhibitors is reported in WO 01/49709 and in U.S. Pat. No. 6,780,625, by the present inventor, which are incorporated by reference as if fully set forth herein. This general strategy is based on defining the structural features of a GSK-3 substrate, and developing GSK-3 inhibitors in accordance with these features. However, while these publications delineate these structural features and teach various short peptides that efficiently inhibit GSK-3 activity, they fail to teach the design and synthesis of small molecules that could serve as GSK-3 inhibitors. WO 2004/052414, by the present inventor, discloses that attaching a hydrophobic moiety to a terminus of a peptide GSK-3 inhibitor enhances its inhibition activity.

However, although peptides are intriguing drug targets, their use is oftentimes limited by, for example, biological instability, immunogenicity, poor capability to cross biological membranes such as cell membranes and the blood brain barrier (BBB), and the like.

There is thus a widely recognized need for, and it would be highly advantageous to have, non-peptidic compounds for inhibiting GSK-3 activity, devoid of the above limitations.

SUMMARY OF THE INVENTION

The present inventors have now surprisingly found that compounds which are designed according to the unique features of the recognition motif of a GSK-3 substrate exhibit substrate competitive inhibition activity toward GSK-3 and can therefore be efficiently used in various applications where reducing the activity of GSK-3 is beneficial.

Thus, according to one aspect of the present invention there is provided a compound comprising a negatively charged group and at least one amino moiety-containing group being covalently linked therebetween via a spacer, the spacer having a length, structure and flexibility selected for allowing at least one interaction between the negatively charged group and a first binding site in a catalytic domain of a GSK-3 and at least one interaction between the amino moiety-containing group and a second binding site in the catalytic domain of a GSK-3, such that the compound is capable of inhibiting a catalytic activity of a GSK-3, with the proviso that the compound is not selected from the group consisting of compounds having a general formula A or B:

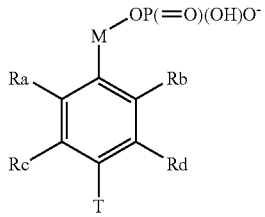

Formula A

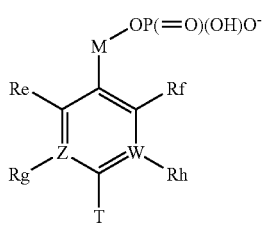

Formula B wherein, for Formula A: M is methylene or absent; Ra, Rb and T are each hydrogen; and Rc and Rd are each independently selected from the group consisting of hydrogen, —CH=N—NH—C(=NH)—NH$_2$, —CH$_2$—N(NH$_2$)—CH$_3$ and —CH$_2$—NH—C(=NH)—OH, and for Formula B: M is methylene or absent; Z and W are each independently nitrogen or carbon, at least one of Z and W being nitrogen; and Re, Rf, Rg, Rh and T are each independently selected from the group consisting of hydrogen, nitro, alkyl, halo, hydroxy and methyl.

According to further features in preferred embodiments of the invention described below, inhibiting the catalytic activity of a GSK-3 comprises diminishing a binding of a substrate to the catalytic domain.

According to still further features in the described preferred embodiments the first binding site comprises at least one amino acid residue selected from the group consisting of arginine 180, arginine 96, and lysine 205.

According to still further features in the described preferred embodiments the second binding site comprises at least one amino acid residue selected from the group consisting of aspartate 181, glutamate 97, aspartate 90, aspartate 181, glutamate 200, glutamine 89, tyrosine 215 and aspartate 95.

According to still further features in the described preferred embodiments the compound further comprises a hydrophobic moiety that is capable of interacting with a third binding site of a GSK-3.

According to still further features in the described preferred embodiments the third binding site is a part of the catalytic domain of the GSK-3.

According to still further features in the described preferred embodiments the third binding site comprises at least one amino acid residue selected from the group consisting of isoleucine 217, phenylalanine 67 and tyrosine 215.

According to still further features in the described preferred embodiments the hydrophobic moiety forms a part of the spacer.

According to still further features in the described preferred embodiments the length of the spacer ranges from 2 angstroms and 50 angstroms.

According to still further features in the described preferred embodiments the negatively charged group has the formula

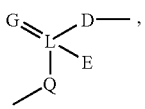

wherein L is selected from the group consisting of a phosphor atom, a sulfur atom, a silicon atom, a boron atom and a carbon atom; Q, G and D are each independently selected from the group consisting of oxygen and sulfur; and E is selected from the group consisting of hydroxy, alkoxy, aryloxy, carbonyl, thiocarbonyl, O-carboxy, thiohydroxy, thioalkoxy and thioaryloxy or absent.

According to still further features in the described preferred embodiments L is phosphor, Q, D and G are each oxygen and E is hydroxy.

According to still further features in the described preferred embodiments the amino moiety-containing group comprises at least one positively charged group.

According to still further features in the described preferred embodiments the at least one positively charged group is selected from the group consisting of ammonium ion and guanidinium ion.

According to still further features in the described preferred embodiments the at least one positively charged group has a chemical structure derived from a side chain of a positively charged amino acid.

According to still further features in the described preferred embodiments the positively charged amino acid is selected from the group consisting of arginine, lysine, histidine, proline and any derivative thereof.

According to still further features in the described preferred embodiments the at least one amino moiety-containing group is selected from the group consisting of guanidino, guanidinoalkyl, amino, aminoalkyl, hydrazine, guanyl and guanyloalkyl.

According to still further features in the described preferred embodiments at least one of the at least one amino moiety-containing group forms a part of the spacer.

According to still further features in the described preferred embodiments the spacer comprises at least one cyclic moiety.

According to still further features in the described preferred embodiments the at least one cyclic moiety is selected from the group consisting of an alicyclic, an aryl, a heteroaryl and a heteroalicyclic.

According to still further features in the described preferred embodiments the spacer comprises at least two cyclic moieties.

According to still further features in the described preferred embodiments at least two of the cyclic moieties are fused to one another.

According to still further features in the described preferred embodiments at least two of the cyclic moieties are linked to one another via a linker.

According to still further features in the described preferred embodiments the linker is selected from the group consisting of a bond, a heteroatom, a hydrocarbon chain and a hydrocarbon chain interrupted by at least one heteroatom.

According to still further features in the described preferred embodiments the compound has the general Formula I:

B-J-(S)$_1$-(S)$_2$ ... (S)$n$-K-(Q)$m$    Formula I wherein:

n is an integer from 0 to 10;

m is an integer from 1 to 6;

B is the negatively charged group;

Q is at least one of the at least one amino moiety-containing group; and

J-(S)$_1$-(S)$_2$ ... (S)n-K is the spacer, whereas:

K is selected from the group consisting of aryl, heteroaryl, alicylic, or heteroalicyclic; and J and S$_1$-Sn are each independently selected from the group consisting of a substituted or unsubstituted aryl, a substituted or unsubstituted heteroaryl, a substituted or unsubstituted alicylic, a substituted or unsubstituted heteroalicyclic, a bond, a heteroatom, a substituted or unsubstituted hydrocarbon chain, a substituted or unsubstituted hydrocarbon chain interrupted by at least one heteroatom, or absent.

According to still further features in the described preferred embodiments m is an integer from 1 to 2.

According to still further features in the described preferred embodiment's n is an integer from 0 to 2.

According to still further features in the described preferred embodiments n is 2 and each of S$_1$, S$_2$ and K is independently selected from the group consisting of aryl and heteroaryl.

According to still further features in the described preferred embodiments J is a hydrocarbon chain.

According to still further features in the described preferred embodiments J is alkyl.

According to still further features in the described preferred embodiments S$_1$ is aryl, S$_2$ is heteroaryl and K is aryl.

According to still further features in the described preferred embodiments S$_1$ is phenyl, S$_2$ is triazole and K is phenyl.

According to still further features in the described preferred embodiments at least one of J and S$_1$-Sn comprises at least one amino moiety-containing group.

According to still further features in the described preferred embodiments the at least one amino moiety-containing group forms a part of the K.

According to still further features in the described preferred embodiments at least one of J, (S)$_1$-(S)n and K comprises a hydrophobic moiety attached thereto.

According to still further features in the described preferred embodiments the hydrophobic moiety is selected from the group consisting of a fatty acid residue, a saturated alkylene chain having between 4 and 30 carbon atoms, an unsaturated alkylene chain having between 4 and 30 carbon atoms, an aryl, a cycloalkyl and a hydrophobic peptide sequence.

According to still further features in the described preferred embodiments the fatty acid is selected from the group consisting of myristic acid, lauric acid, palmitic acid, stearic acid, oleic acid, arachidonic acid, linoleic acid and linolenic acid.

According to still further features in the described preferred embodiments J is a hydrocarbon chain or absent and n is 0.

According to still further features in the described preferred embodiments such a compound has a general formula II:

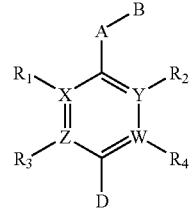

Formula II wherein:

X, Y, Z and W are each independently a carbon atom or a nitrogen atom;

A is the J;

B is the negatively charged group;

D is selected from the group consisting of hydrogen, alkyl, C$_1$ to C$_6$ substituted alkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonamide, carbonyl, ketoester, thiocarbonyl, ester, ether, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanyloalkyl, guanidino, guanidinoalkyl, amino, hydrazine, aminoalkyl and a hydrophobic moiety; and R$_1$, R$_2$, R$_3$ and R$_4$ are each independently selected from the group consisting of the amino moiety-containing group, hydrogen, a lone pair of electrons, alkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonamide, carbonyl, ketoester, thiocarbonyl, ester, ether, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanylinoalkyl, guanidino, guanidinoalkyl, amino, aminoalkyl, hydrazine and an ammonium ion, or a pharmaceutically acceptable salt thereof, provided that at least one of X, Y, Z and W is a nitrogen atom and/or at least one of R$_1$, R$_2$, R$_3$ and R$_4$ is the amino moiety-containing group.

According to further features in preferred embodiments of the invention described below, D in the above formula is a hydrophobic moiety, and thus, according to another aspect of the present invention there is provided a compound having the formula described above, wherein D is a hydrophobic moiety, as described herein. The compound according to this aspect of the present invention includes also the compounds excluded above, substituted by the hydrophobic moiety.

The compounds described hereinabove are capable of inhibiting an activity of GSK-3.

According to still further features in the described preferred embodiments A is alkyl.

According to still further features in the described preferred embodiments at least one of X, Y, Z and W is a nitrogen atom.

According to still further features in the described preferred embodiments at least two of X, Y, Z and W are nitrogen atoms. Preferably either X and Y are each a nitrogen atom or Z and W are each a nitrogen atom.

According to still further features in the described preferred embodiments at least one of $R_1$, $R_2$, $R_3$ and $R_4$ is a group containing at least one amino moiety.

According to still further features in the described preferred embodiments at least two of $R_1$, $R_2$, $R_3$ and $R_4$ are groups containing at least one amino moiety. Preferably either each of $R_1$ and $R_2$ or each of $R_3$ and $R_4$ is a group containing at least one amino moiety.

Examples of groups containing at least one amino moiety include, without limitation, guanidino, guanidinoalkyl, aminoalkyl, analogs thereof, derivatives thereof and any combination thereof.

According to still further features in the described preferred embodiments the group containing at least one amino moiety comprises at least one positively charged group.

According to still further features in the described preferred embodiments the positively charged group comprises an ammonium ion and/or a guanidinium ion. Alternatively, the positively charged group has a chemical structure that is derived from a side chain of a positively charged amino acid, such as, but not limited to, arginine, lysine, histidine, proline and any derivative thereof.

Preferred compounds according to the present invention further include compounds in which each of X, Y, Z and W is a carbon atom; and at least one of $R_1$, $R_2$, $R_3$ and $R_4$ is the group containing at least one amino moiety as described above.

Further preferred compounds are those in which each of X, Y and Z is a carbon atom and W is a nitrogen atom.

According to still another aspect of the present invention there is provided a pharmaceutical composition that comprises, as an active ingredient, any of the compounds described hereinabove, which is capable of inhibiting an activity of GSK-3, and a pharmaceutically acceptable carrier.

According to further features in preferred embodiments of the invention described below, the pharmaceutical composition is packaged in a packaging material and is identified in print, on or in the packaging material, for use in the treatment of a biological condition associated with GSK-3 activity, as is detailed hereinbelow.

According to still further features in the described preferred embodiments the pharmaceutical composition further comprises at least one additional active ingredient that is capable of altering an activity of GSK-3, as is detailed hereinbelow.

According to yet another aspect of the present invention there is provided a method of treating a biological condition associated with an activity of GSK-3, which is effected by administering to a subject in need thereof a therapeutically effective amount of a compound which comprises a negatively charged group and at least one amino moiety-containing group being linked therebetween via a spacer, wherein the spacer has a length, structure and flexibility suitable for enabling at least one interaction between the negatively charged group and a first binding site in the catalytic domain of a GSK-3 and at least one interaction between the amino moiety-containing group and a second binding site in the catalytic domain of a GSK-3, as is described hereinabove.

According to further features in preferred embodiments of the invention described below, the method according to this aspect of the present invention further comprises co-administering to the subject at least one additional active ingredient, which is capable of altering an activity of GSK-3.

The additional active ingredient can be an active ingredient that is capable of inhibiting an activity of GSK-3 or an active ingredient that is capable of downregulating an expression of GSK-3.

The biological condition according to the present invention is preferably selected from the group consisting of obesity, non-insulin dependent diabetes mellitus, an insulin-dependent condition, an affective disorder, a neurodegenerative disease or disorder and a psychotic disease or disorder.

The affective disorder can be a unipolar disorder (e.g., depression) or a bipolar disorder (e.g., manic depression).

The neurodegenerative disorder can results from an event selected from the group consisting of cerebral ischemia, stroke, traumatic brain injury and bacterial infection, or can be a chronic neurodegenerative disorder that results from a disease selected from the group consisting of Alzheimer's disease, Huntington's disease, Parkinson's disease, AIDS associated dementia, amyotrophic lateral sclerosis (AML) and multiple sclerosis.

According to an additional aspect of the present invention there is provided a method of inhibiting an activity of GSK-3, which comprises contacting cells expressing GSK-3 with an inhibitory effective amount of a compound which comprises a negatively charged group and at least one amino moiety-containing group being linked therebetween via a spacer, wherein the spacer has a length, structure and flexibility suitable for enabling at least one interaction between the negatively charged group and a first binding site in the catalytic domain of a GSK-3 and at least one interaction between the amino moiety-containing group and a second binding site in the catalytic domain of a GSK-3.

The activity can be a phosphorylation activity and/or an autophosphorylation activity.

According to yet an additional aspect of the present invention there is provided a method of potentiating insulin signaling, which comprises contacting insulin responsive cells with an effective amount of which comprises a negatively charged group and at least one amino moiety-containing group being linked therebetween via a spacer, wherein the spacer has a length, structure and flexibility suitable for enabling at least one interaction between the negatively charged group and a first binding site in the catalytic domain of a GSK-3 and at least one interaction between the amino moiety-containing group and a second binding site in the catalytic domain of a GSK-3.

In each of these methods, the contacting the cells can be effected in vitro or in vivo.

According to further features in preferred embodiments of the invention described below, each of the methods according to these additional aspects of the present invention further comprises contacting the cells with at least one an additional active ingredient, as is described hereinabove.

The present invention successfully addresses the shortcomings of the presently known configurations by providing newly designed, non-peptidic compounds for inhibiting GSK-3 activity, which can be efficiently used in the treatment of a variety of biological conditions.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the singular form "a," "an," and "the" include plural references unless the context clearly dictates otherwise. For example, the term "a compound" or "at least one compound" may include a plurality of compounds, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1a-b present computer images of the 3D structure of the peptides p9CREB (FIG. 1a) and CREB (FIG. 1b), as obtained by 2D $^1$H-NMR studies (hydrogen atoms not shown; carbon backbone is in gray, nitrogen atoms are in blue, oxygen atoms are in red and phosphor atoms are in yellow);

FIG. 2 is an image showing the electrostatic distribution of the p9CREB peptide, based on the 3D structure of the peptide obtained by 2D $^1$H-NMR studies;

FIGS. 4a-b present the ESI-MS (FIG. 4a) and an HPLC chromatogram (FIG. 4) of 3,5-Bis(2-aminoethyl)benzyl phosphate (GSC-21);

FIGS. 7a-b present comparative plots demonstrating the GSK-3 inhibition activity of GSC-1, GSC-2, GSC-3 and GSC-4 (FIG. 7a, black circles denote GSC-2, blanc circles denote GSC-1, black triangles denote GSC-3 and black rectangles denote GSC-4) and GSC-5, GSC-6 and GSC-7 (FIG. 7b, rectangles denote GSC-5, triangles denote GSC-6 and circles denote GSC-7) in in vitro inhibition assays with p9CREB peptide substrate;

DESCRIPTION OF THE PREFERRED EMBODIMENTS

Figure 3A:
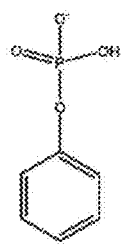
FIGS. 3a-b present the chemical structures of phenyl phosphate, pyridoxal phosphate (P-5-P), GSC-1, GSC-2, GSC-3 and of the novel compounds GSC-4, GSC-5 and GSC-21 (FIG. 3a) and of the novel compounds GSC-6, GSC-7, GSC-8 and GSC-9 (FIG. 3b)
Figure 3A:
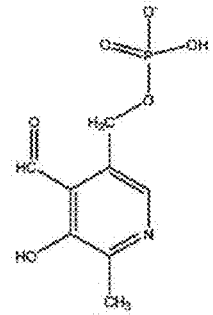
Figure 3A:
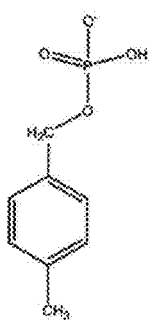
Figure 3A:
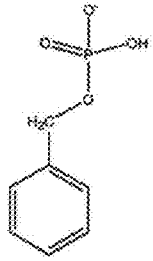
Figure 3A:
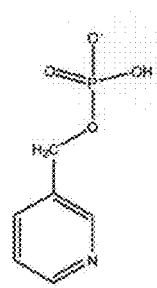
Figure 3A:
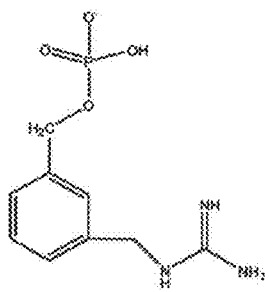
Figure 3A:
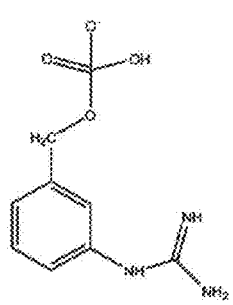
Figure 3A:
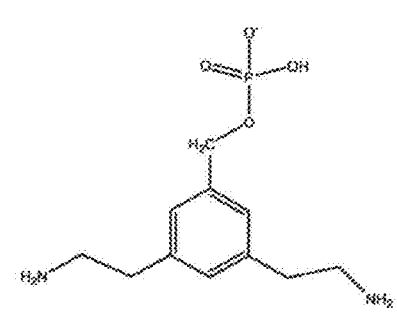

The present invention is of novel, non-peptidic compounds, which are capable of inhibiting GSK-3 activity and can therefore be used in the treatment of biological conditions mediated by GSK-3. Specifically, the present invention is of (i) compounds that are designed according to the pharmacophoric coordinates of a GSK-3 substrate, which may optionally have a hydrophobic moiety attached thereto; (ii) pharmaceutical compositions containing same; (iii) methods of using same for inhibiting GSK-3 activity and potentiating insulin signaling; and (iv) methods of using same in the treatment of biological conditions such as, but not limited to, obesity, non-insulin dependent diabetes mellitus, insulin-dependent conditions, affective disorders, neurodegenerative diseases and disorders and psychotic diseases or disorders.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

One of the parameters that are responsible for substrate-kinase recognition is an element located within the substrate, which is usually related to as a "recognition motif". As is discussed hereinabove, GSK-3, unlike other kinases, has a unique recognition motif, which includes the amino acid sequence $SX_1X_2X_3S(P)$, set forth in SEQ ID NO:1, where S is serine or threonine, each of $X_1$, $X_2$ and $X_3$ is any amino acid, and S(p) is phosphorylated serine or phosphorylated threonine.

As is widely taught in WO 01/49709 and in U.S. Pat. No. 6,780,625, which are incorporated by reference as if fully set forth herein, a set of short peptides which were designed and synthesized based on this recognition motif were tested for their activity either as substrates or as inhibitors. Base on these assays, a number of features which rendered these peptides active substrates or inhibitors toward GSK-3, were determined. One of the most important features was that the phosphorylated serine or threonine residue in the motif is necessary for binding both substrates and inhibitors to GSK-3. These assays further demonstrated that some of these peptides were highly potent and specific inhibitors of GSK-3. These peptides were defined as substrate competitive inhibitors.

Based on the findings that GSK-3 recognizes only pre-phosphorylated substrates, namely, substrates that have a phosphorylated serine or threonine residue, it was hypothesized that these pre-phosphorylated GSK-3 substrates has a unique structure which allows them to interact with the catalytic core of GSK-3. It was further hypothesized that determining this unique structure would enable the development of small molecules that could act as substrate competitive inhibitors of GSK-3.

Thus, in a search for small molecules that would mimic the inhibitory activity of the small GSK-3 peptide inhibitors described hereinabove, while reducing the present invention to practice, the three dimensional structure, as well as the unique structural features, of a short phosphorylated peptide substrate have been determined, and a number of compounds characterized by these features were selected and tested for their activity as GSK-3 inhibitors.

As a representative example of a GSK-3 substrate the short pre-phosphorylated peptide p9CREB (ILSRRPS(p)YR, SEQ ID NO:2) was selected. The three-dimensional structures of p9CREB, as well as of the corresponding non-phosphorylated peptide CREB (ILSRRPSYR, SEQ ID NO:3) were determined by 2D NMR, as is detailed in the Examples section that follows (see, Example 1).

As shown in FIGS. 1a and 1b, the phosphorylated p9CREB substrate has a defined structure in solution (FIG. 1a), whereby the corresponding non-phosphorylated peptide CREB does not exhibit any unique structure (FIG. 1b).

In view of these results it was suggested that the phosphate group in the phosphorylated peptide imposes a 'loop-like' structure, through a cation-pi interaction between tyrosine (Y8) and arginine (R4) (see, Tables 2 and 3), and as a result, the phosphorylated serine at the recognition motif is positioned outside the loop. Such a "bended" structure of the substrate renders the phosphorylated serine accessible to interact with the substrate binding pocket of the enzyme.

A support for this suggestion was indeed found in the recently published crystallization data of GSK-3, described by Dajani et al. (2001). The crystallization data of Dajani et al. show that the substrate binding site of GSK-3 comprises three positively charged residues, Arg 96, Arg 180, and Lys 205, which interact with a phosphate ion.

FIG. 2 presents the electrostatic distribution on the 'surface' of the p9CREB peptide, based on these findings.

While continuing to conceive the present invention, it was deduced from the findings described hereinabove that a small molecule that would mimic the structure of a GSK-3 substrate such that it would exerts substrate competitive inhibitory activity should be designed according to the following features:

The molecule should include a negatively charged group, preferably a phosphate group;

The negatively charged group should not be stearically hindered; and

The negatively charged group should preferably be flanked at least at one side or at both sides thereof by one or two positively charged groups.

Based on the above, a general formula of potential compounds for inhibiting GSK-3 activity has been designed (see, Example 2). As is described in the Examples section that follows (see, Example 3), preliminary experiments that were conducted with a 'first generation' of these compounds, namely, compounds having the most simplified structure of this formula, demonstrated the capability of these compounds to inhibit GSK-3 activity, thus providing a preliminary indication of the inhibitory potential of compounds having such a formula.

A more advanced generation of compounds, which includes novel compounds, was also designed and synthesized based on the above (see, for example, Example 2). As is described in the Examples section that follows (see, Example 3), experiments conducted with these compounds further demonstrated their capability to inhibit GSK-3 activity and also to enhance the glucose uptake in mice adipocytes, thus demonstrating the promising inhibitory and therapeutic effect exerted by compounds designed according to such a formula.

This 'first generation' compounds family was based on a mono aryl or heteroaryl core (having one aryl or heteroaryl ring), to which a negatively charged group and one or two positively charged groups are attached. This family is also collectively referred to herein as GSC molecules.

Additional studies on the pharmacophoric binding sites of the catalytic domain of GSK-3 were conducted in order to evaluate the interactions of the designed molecules with these binding sites and to further design small molecules that would strongly interact with these binding sites and thus would inhibit GSK-3 activity via competing with substrate binding. In these studies, the protein crystallography data of GSK-3 as taught by Ter Haar et al. (2001) served as a model.

As is described in the Examples section that follows (see, Example 4), it was deduced from these studies that the catalytic domain of GSK-3 includes various binding sites that can interact simultaneously with various functionalities (e.g., negatively and/or positively charged groups, hydrophobic moieties) of a small molecule. It was thus deduced that in order to achieve a maximized number and strength of interactions with these binding sites, small molecules should be designed such that most, if not all, the various functionalities would be in a suitable proximity and orientation to the binding sites. Thus, for example, it was deduced that design of small molecules in which the distance between the negatively charged group and the one or more positively charged group(s) is greater than that obtained with a single aromatic ring should be considered.

To this end, a second generation of compounds have been designed and successfully prepared (see, Example 5) and practiced (see, Example 6). These compounds were designed to include a spacer, linking the negatively charged group and one or more positively charged groups, which would have a suitable length, structure and flexibility, and hence would allow strong interactions with various binding sites in the catalytic core of GSK-3. Representative examples of such 'second generation' compounds are compounds in which the spacer is composed of three cyclic moieties, and further in which the negatively and positively charged groups are positioned in certain orientations to one another. As is described in the Examples section that follows (see, Example 6), experiments conducted with these compounds demonstrated their high capability to inhibit GSK-3 activity and further demonstrated the effect of the relative orientation between the functional groups (see, for example, FIG. 19).

Hence, according to one aspect of the present invention there is provided a compound which comprises a negatively charged group and at least one amino moiety-containing group being covalently linked therebetween via a spacer. The spacer is designed to have a length, structure and flexibility selected for allowing at least one interaction between the negatively charged group and a first binding site in a catalytic domain of a GSK-3 and at least one interaction between the amino moiety-containing group and a second binding site in the catalytic domain of a GSK-3, such that the compound is capable of inhibiting a catalytic activity of a GSK-3.

As used herein, the phrase "catalytic domain" describes a region of an enzyme in which the catalytic reaction occurs. This phrase therefore describes this part of an enzyme in which the substrate and/or other components that participate in the catalytic reaction interacts with the enzyme. In the context of the present invention, this phrase is particularly used to describe this part of an enzyme (a GSK-3) to which the substrate binds during the catalytic activity (e.g., phosphorylation). This phrase is therefore also referred to herein and in the art, interchangeably, as "substrate binding pocket", "catalytic site" "active site" and the like.

As used herein, the phrase "binding site" describes a specific site in the catalytic domain that includes one or more reactive groups through which the interactions with the substrate and/or other components can be effected. Typically, the binding site is composed of one or two amino acid residues, whereby the interactions typically involve reactive groups at the side chains of these amino acids. As is detailed hereinbelow, during the substrate binding, conformational changes of the catalytic domain of the enzyme occur so as to bring the reactive groups in suitable proximity and orientation, and allow their interaction with the functional groups of the substrate. Hence, the phrase "binding site" as used herein encompasses those amino acid residues that are positioned in such proximity and orientation that allows such interaction.

The interactions of the various functional groups of the compound with the various binding sites of the enzyme can be, for example, electrostatic interactions, hydrogen bonding interactions, hydrophobic interactions, aromatic interactions, π-stacking interactions, and the like, depending on the reactive groups that participate in the interactions and their proximity and orientation to one another.

Exemplary electrostatic interactions include anion-cation interactions and acid-base interactions such as, for example, interactions between ammonium cation and carboxylate anion.

Exemplary hydrogen bonding interactions include interactions between hydrogens of amine, hydroxel or thiol of one or more component(s) and e.g., oxygen, nitrogen and sulfur atoms of other component(s).

Exemplary hydrophobic interactions include interactions between two or more hydrocarbon moieties such as alkyl, cycloalkyl and aryl.

Exemplary aromatic interactions include interactions between two or more aromatic moieties such as aryls and heteroaryls, which are based on overlap in the aromatized molecular orbitals of the moieties.

Exemplary π-stacking interactions include interactions between two or more moieties that contain π-electrons (e.g., unsaturated moieties), which are based on overlap in the π-orbitals of the moieties.

As is briefly discussed hereinabove and is well known in the art, substrate competitive enzyme inhibitors act by binding to the catalytic domain of an enzyme and thus reducing the proportion of enzyme molecules that are bound to the enzyme during the catalytic process. When an enzyme interacts with a substrate or an inhibitor, the initial interaction rapidly induces conformational changes in the enzyme that strengthen binding and bring catalytic sites close to functional groups in the substrate or inhibitor. Enzyme-substrate/inhibitor interactions orient reactive groups present in both the enzyme and the substrate/inhibitor and bring them into proximity with one another. The binding of the substrate/inhibitor to the enzyme aligns the reactive groups so that the relevant molecular orbitals overlap.

Thus, an efficient substrate competitive inhibitor should be designed such that the reactive groups of the inhibitor would be positioned in sufficient proximity to corresponding reactive groups (typically side chains of amino acid residues) in the enzyme catalytic domain, so as to allow the presence of an effective concentration of the inhibitor in the catalytic domain and, in addition, the reactive groups of the inhibitor should be positioned in a proper orientation, to allow overlap. Still in addition, an inhibitor should have a restriction of its conformational flexibility, so as to avoid conformational changes that would affect or weaken the interactions and should include structural elements that are known to be involved in the interactions.

As is further discussed hereinabove, initial studies have uncovered that GSK-3 substrates have a negatively charged group and one or more positively charged groups, whereby the negatively charged group is positioned in a special spatial orientation. Substrate competitive GSK-3 inhibitors should therefore include both these groups and the relative orientation thereof. Hence, in order to allow strong interactions between these functional groups and reactive groups in the catalytic domain of GSK-3, an inhibitor should be designed such that these functional groups would be in optimal proximity and orientation towards the enzyme's reactive groups. The proximity and orientation of these functional groups are determined, according to the present embodiments, by selecting a spacer that links these functional groups such that when interacting with reactive groups in the catalytic domain, each functional group would be in an optimal proximity and orientation towards one or more compatible reactive groups in the enzyme binding sites. A suitable spacer would therefore have suitable length, flexibility and structure that would allow efficient interaction, in terms of proximity and orientation, between each functional group and one or more compatible reactive group.

As described hereinabove, previous studies on the crystallography of GSK-3 have shown that GSK-3 substrates interact with the catalytic domain of the enzyme such that the negatively charged group (e.g., phosphate) interacts with one or more of arginine 180, arginine 96, and lysine 205 (see, Dajani et al. 2001 and Ter Haar et al. 2001). Hence, according to a preferred embodiment of the present invention, the first binding site (with which the negatively charged group can interact, as described hereinabove) comprises one or more of these amino acid residues. Thus, the compounds are designed such that interactions between the negatively charged group and one or more of these amino acid residues are allowed. These interactions are preferably electrostatic interactions. However, any other chemically compatible binding sites in the catalytic domain of GSK-3 that are arranged in proximity and orientation that allows interactions with the negatively charged group of the inhibitor are also within the scope of the present invention.

As is detailed in the Examples section that follows (see, Example 4), molecular modeling studies of the interaction of substrate competitive inhibitors have shown that, depending on mutual proximity and orientation, the amino moiety-containing group(s) interact with one or more of aspartate 181, glutamate 97, aspartate 90, aspartate 181, glutamate 200, glutamine 89, tyrosine 215 and aspartate 95. Hence, according to a preferred embodiment of the present invention, the second binding site (with which the amino moiety-containing group(s) can interact, as described hereinabove) comprises one or more of these amino acid residues. Thus, the compounds are designed such that interactions between the amino moiety-containing group(s) and one or more of these amino acid residues are allowed. These interactions can be, for example electrostatic interactions and/or hydrogen binding interactions. However, any other chemically compatible binding sites in the catalytic domain of GSK-3 that are arranged in proximity and orientation that allows interactions with the amino moiety-containing group (s) of the inhibitor are also within the scope of the present invention.

While the compounds described herein preferably comprise one negatively charged group, they may comprise one or more (e.g., two, three) amino moiety-containing groups. Hence the second binding site described herein includes all of those reactive groups that interact with all of the amino moiety-containing groups.

The compounds described herein can further include a hydrophobic moiety that may participate in the interactions of the compound with the enzyme. The hydrophobic moiety can be attached to the spacer such that the length, structure and flexibility of the spacer would allow its interactions with another (third) binding site of the enzyme. Optionally or in addition, the hydrophobic moiety can form a part of the spacer itself, by selecting a hydrophobic spacer.

The interactions of a hydrophobic moiety may be within the catalytic domain and/or within another region of the enzyme. Thus, for example, these interactions can be within a hydrophobic patch that is present within the enzyme, as was previously reported by Dajani et al. (2001). In another example, these interactions can be with one or more of the amino acid residues isoleucine 217, phenylalanine 67 and tyrosine 215 in the catalytic domain of a GSK-3. However, any other hydrophobic binding sites in the catalytic domain of GSK-3 that are arranged in proximity and orientation that allows interactions with the hydrophobic moiety of the inhibitor are also within the scope of the present invention. These interactions can be hydrophobic interactions, aromatic interactions and/or π-stacking interactions, depending on the chemical structure of the moiety and the binding site. Additional description of hydrophobic moieties is set forth below.

The present inventors have uncovered that an optimal distance between the negatively charged group and the amino moiety-containing group ranges from about 2 angstroms and about 50 angstroms. Hence, according to a preferred embodiment of the present invention, the length of spacer ranges from about 2 angstroms and about 50 angstroms, more preferably from about 2 angstroms and about 20 angstroms, and more preferably from about 2 angstroms and about 10 angstroms. An exemplary spacer would thus have a length of about 7-8 angstroms.

The present inventors have further uncovered that the flexibility of the spacer should preferably be restricted. Hence, the spacer preferably comprises one or more cyclic moieties. Depending on the features of the GSK-3 and the nature of the functional moieties (e.g., negatively charged group, amino moiety-containing group, hydrophobic moiety) in the compound, in cases where the spacer comprises two or more cyclic moieties, the moieties can be either fused and/or non-fused. When non-fused, each two cyclic moieties can be linked to one another via linker such as, but not limited to, a bond, a heteroatom (e.g., oxygen, nitrogen, sulfur) or a hydrocarbon chain, as these terms are defined hereinbelow. The hydrocarbon chain can optionally be interrupted by one or more heteroatoms (e.g., oxygen, nitrogen, sulfur and the likes).

The presence (in cases where the cyclic moieties are non-fused) and absence (in cases where the cyclic moieties are fused) of a linker, as well as its nature, depend on the degree of flexibility that is required so as to allow the above described interactions. Thus, in cases where the flexibility should be substantially restricted, a rigid spacer that comprises two or more fused cyclic moieties is preferred. Alternatively, a rigid spacer that comprises two or more aromatic moieties (aryl and/or heteroaryl) is preferred. In cases where restricting the flexibility is required only to some extent, a semi-rigid spacer that allows free rotation of one or more bonds is preferred. In most cases it is desirable to have a spacer that provides the compound with at least some rotatability that would allow the functional groups to readily interact with the reactive groups in the binding sites.

In a preferred embodiment of the present invention, the spacer comprises two or more, preferably three cyclic moieties, which are covalently linked to one another via a bond.

In each of these embodiments, each of the cyclic moieties can be, for example, a carbocylic moiety or a heterocyclic moiety.

As used herein, a "carbocylic moiety" describes an all-carbon, saturated or unsaturated cyclic moiety, whereby a "heterocyclic moiety" describes a saturated or unsaturated cyclic moiety that includes one or more heteroatoms such as nitrogen, oxygen, sulfur, phosphor, silicone and the like.

Carbocylic moieties include cycloalkyls and aryls, as these terms are defined hereinbelow. Heterocyclic moieties include heteroalicyclics and heteroaryls, as these terms are defined hereinbelow.

Aromatic cyclic moieties (aryls and heteroaryls), by being more rigid than non-aromatic cyclic moieties (cycloalkyls and heteroalicyclics), are preferred due to the restriction of conformational changes in their structures. However, a combination of aromatic and non-aromatic cyclic moieties can also allow the desired interactions.

In cases where the spacer comprises a heterocyclic moiety that contains one or more nitrogen atoms, this moiety can serve as an amino moiety-containing group that participates in the interactions with the binding sites.

In cases where the spacer comprises carbocyclic moiety and/or a hydrocarbon chain, these moieties can serve as hydrophobic and/or aromatic moieties that participate in the interactions with the binding sites, as discussed hereinabove.

Thus, the spacer can be further selected so as to have a structure that would allow or restrict interactions thereof with binding sites of the enzyme. Exemplary spacers that have a structure that allows interactions with binding sites include, without limitations, hydrophobic moiety-containing spacers, aromatic moiety-containing spacers and amino moiety-containing (e.g., heterocylic) spacers.

The structure of the spacer, however, can further affect its flexibility, stability and other features that may be implicated with the interactions of the compound with the binding sites in the catalytic domain of GSK-3.

Preferred compounds according to the present embodiments therefore include a rigid or a semi-rigid spacer, to which a negatively charged group is attached. As this structure mimics the unique structure of a GSK-3 substrate by providing a negatively charged group which is not stearically hindered and has a geometrical structure similar or identical to a phosphate group, and further by allowing interactions of the negatively charged group and an amino moiety-containing group with binding sites of GSK-3, these compounds are capable of inhibiting GSK-3 activity, preferably via inhibition of the substrate binding to the enzyme.

The phrases "negatively charged group" and "positively charged group", as used herein, refer to an ionizable group, which upon ionization, typically in an aqueous medium, has at least one negative or positive charge, respectively. The charged groups can be present in the compounds described herein either in their ionized form or as a pre-ionized form.

The negatively charged group, according to preferred embodiments of the present invention, has the formula

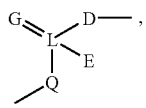

wherein L is selected from the group consisting of a phosphor atom, a sulfur atom, a silicon atom, a boron atom and a carbon atom; Q, G and D are each independently selected from the group consisting of oxygen and sulfur; and E is selected from the group consisting of hydroxy, alkoxy, aryloxy, carbonyl, thiocarbonyl, O-carboxy, thiohydroxy, thioalkoxy and thio-aryloxy, as these terms are defined hereinbelow, or absent.

Preferably, the negatively charged group is a phosphate group, such that in the formula above L is a phosphor atom, whereby each of Q, G and D is oxygen. Further preferably, E is hydroxy. Alternatively, the hydroxy group can also be ionized so as to have another negative electrostatic charge.

Alternatively, the negatively charged group can be a thiophosphate group, sulfate or sulfonate group, a borate or boronate group and the like, according to the formula above.

The negatively charged group is preferably attached to the spacer via an alkyl group, preferably an unsubstituted alkyl, and more preferably a methyl.

The attachment of the negatively charged group to the ring via an alkyl group renders the negatively charged group a free rotatable group as opposed to its restricted rotatability when attached directly to the spacer. The free rotatability of the negatively charged group is advantageous since it allows the negatively charged group to readily interact with the binding site of the enzyme.

The positively charged group is preferably derived from an amine moiety-containing group, which can be present in the compound in its ionized form (e.g., as an ammonium or guanidinium ion) or as a free amine (a pre-ionized form).

As used herein, the phrase "amino moiety-containing group" refers to a group which contains one or more amino moieties, as this term is defined herein or to an amine per se.

Representative examples of amino moiety-containing groups include, without limitation, an amine, an aminoalkyl, hydrazine, urea, thiourea, guanyl, amido, carbamyl, guanidino, guanidinoalkyl and guanylinoalkyl, as these terms are defined herein.

As is well known in the art, a free amine group is typically basic under neutral conditions and therefore, at a biological environment, it tends to be protonated so as to produce a positively charged $-NH_3^+$ group, for example. As is described hereinabove, a compound that has one or two of such positively charged groups flanking the negatively charged group in a suitable distance and orientation with respect to the binding sites of the enzyme is preferable.

Thus, the amino moiety is preferably present in this group as a readily-protonated moiety, that is, a moiety in which the amino nitrogen has a substantial partially negative charge.

Preferred examples of amino moiety-containing groups therefore include, without limitation, an amine, an aminoalkyl, guanyl, guanylinoalkyl, guanidino, guanidinoalkyl and guanylinoalkyl, as these terms are defined herein.

The amino moiety-containing groups can be present in the compounds described herein either as is or as positively charged groups, in which at least one of the amino moieties is ionized.

As is described above, positively charged groups according to the present invention comprise an ammonium ion, such that representative examples of positively charged groups include, without limitation, an ammonium ion per se (a protonated amino group) and any group that bears an ammonium ion, as is defined hereinabove, such as an alkyl, cycloalkyl or aryl substituted by an ammonium ion, guanidino, guanyl, hydrazine and the like.

Particularly preferred are positively charged groups that have a chemical structure derived from a side chain of a positively charged amino acid, e.g., lysine, arginine, histidine, proline and derivatives thereof, with the first two being the most preferred.

By "a chemical structure derived from a side chain of a positively charged amino acid" it is meant that the positively charged group has a similar or identical chemical structure as such a side chain.

Representative examples include guanidine and guanidinoalkyl (derived from arginine), amine and aminoalkyl (derived from lysine) and imidazole (derived from histidine), with the first being the presently most preferred.

Preferred compounds according to the present embodiments can be collectively represented by general Formula I:

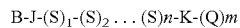   Formula I wherein:

n is an integer from 0 to 10;

m is an integer from 1 to 6;

B is a negatively charged group, as described hereinabove;

Q is one of the amino moiety-containing group(s) described hereinabove; and

J-(S)$_1$-(S)$_2$ ... (S)n-K is the spacer described hereinabove, whereas:

K is selected from the group consisting of aryl, heteroaryl, alicylic, or heteroalicyclic; and J and S$_1$-Sn are each independently selected from the group consisting of a substituted or unsubstituted aryl, a substituted or unsubstituted heteroaryl, a substituted or unsubstituted alicylic, a substituted or unsubstituted heteroalicyclic, a bond, a heteroatom, a substituted or unsubstituted hydrocarbon chain, a substituted or unsubstituted hydrocarbon chain interrupted by at least one heteroatom, as these terms are defined herein, or absent. When the aryl, heteroaryl, cycloalkyl, heteroalicyclic and the hydrocarbon chain are substituted, the substituents can be any of those described hereinbelow.

Thus, the spacer in these compounds is comprised of at least one cyclic moiety (K in Formula I above) to which 1-6 amino moiety-containing groups are attached. Preferably one or two amino moiety-containing groups are attached to the cyclic moiety K, such that m in Formula I above ranges from 1 to 2. Optionally, one of the amino moiety-containing groups, denoted as Q in Formula I, above forms a part of the cyclic moiety K, as is detailed hereinabove. In these cases, K is a heteroalicyclic or a heteroaryl, preferably heteroaryl.

As is well known in the art, a nitrogen atom within an aromatic ring is typically basic under neutral conditions and therefore, at a biological environment, it tends to be protonated so as to produce a positively charged =NH$^+$— group.

Additional amino moiety-containing groups can also be present within the compound. Thus, at least one of the J and S$_1$-Sn moieties can comprise one or more amino moiety-containing group(s). The amino moiety-containing group(s) can be attached to these moieties or form a part thereof, as described hereinabove.

The negatively charged group (B in Formula I above) can be attached to the cyclic moiety K directly (when n=0 and J is absent in Formula I above). Optionally and preferably, a longer spacer links the negatively charged group B and the amino moiety-containing group Q, such that at least one of J and S$_1$-Sn is present within the spacer.

As is discussed hereinabove, by selecting the number and structure of the components composing the spacer (J, S$_1$-Sn and K in Formula I above), the length, structure and flexibility of the spacer can be determined so as to allow the desired interactions described hereinabove.

Thus, for example, by selecting a spacer in which each of J, S$_1$-Sn and K is a cyclic moiety, a rigid structure of the spacer is obtained.

By selecting such a spacer in which the cyclic moieties are aromatic moieties, a more rigid structure is obtained. By selecting such a spacer in which two or more of cyclic moieties are fused, an even more rigid structure is obtained, and so on.

On the other hand, by selecting a spacer in which at least one of J and S$_1$-Sn is a heteroatom, a more flexible spacer is obtained. By selecting a spacer in which at least one of J and S$_1$-Sn is a hydrocarbon chain, an even more flexible spacer is obtained. By selecting a spacer in which each of J and S$_1$-Sn is a heteroatom or a hydrocarbon chain, an even more flexible spacer is obtained.

In another example, the number and size of the moieties composing the spacer determines the length of the spacer. In cases where a lengthy spacer is required in order to allow the desired interactions, n is greater than 5. In cases where a shorter spacer is required, n is lower than 5 and can also be 0.

As is described in the Examples section that follows, in molecular studies conducted based on the crystallographic data of GSK-3 reported by Ter Haar et al. (2001), which is incorporated by reference as if fully set forth herein, it was found that preferred substrate binding inhibitors of GSK-3 have a spacer in a length of about 7-8 angstroms.

Based on these findings and on additional results obtained for the activity of various compounds (see, Examples 3 and 6), it was deduced that preferred compounds comprise a spacer that have a length that ranges from 2 angstroms and 50 angstroms, preferably from 2 angstroms and 20 angstroms and more preferably from 2 angstroms and 10 angstroms.

Considering an average length of a cyclic moiety of 2-2.5 angstroms, preferred inhibitors are therefore comprised of 1-3 cyclic moieties.

Thus, in a preferred embodiment of the present invention, n is an integer from 0 to 2.

In another preferred embodiment, n is 2 and each of S$_1$, S$_2$ and K is independently selected from the group consisting of aryl and heteroaryl.

As is discussed hereinabove, the negatively charged group can be attached to the spacer either directly or indirectly, with the latter being preferred. Thus, J in Formula I above can be absent (when the negatively charged group is directly attached to the spacer) or a flexible group that would allow this group to readily interact with the first binding site described hereinabove.

Thus, preferably, J is a hydrocarbon chain such as alkyl. Preferably, J is a short alkyl (C$_1$-C$_6$ alkyl) and more preferably it is methyl.

Based on the above preferred features, a representative family of compounds having Formula I above has been designed and representative compounds of this family have been successfully prepared. As is demonstrated in the Examples section that follows (see, Example 6), these compounds, which are also referred to herein interchangeably as MP molecules or multi aryl/heteroaryl small molecules, were found highly active as substrate competitive inhibitors of GSK-3.

Hence, preferred compounds according to these embodiments of the present invention can be collectively represented by the general Formula III:

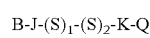
B-J-(S)$_1$-(S)$_2$-K-Q    Formula III wherein B and Q are as described hereinabove, J is alkyl and each of S$_1$, Sn and K is aryl or heteroaryl.

Exemplary compounds in this category are those having the general Formula above in which B is phosphate, J is alkyl (e.g., methyl), S$_1$ is aryl (e.g., phenyl), S$_2$ is heteroaryl (e.g., triazole) and K is aryl (e.g., phenyl).

Figure 18:
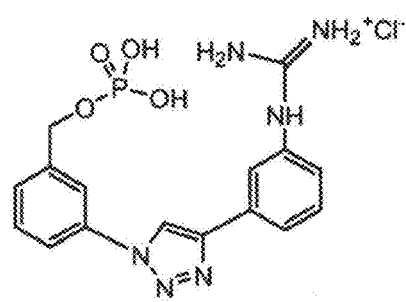
FIG. 18 presents the chemical structures of the newly designed GSK-3 inhibitors MP-1, MP-2, MP-3, MP-4, MP-5 and MP-6.
Figure 18:
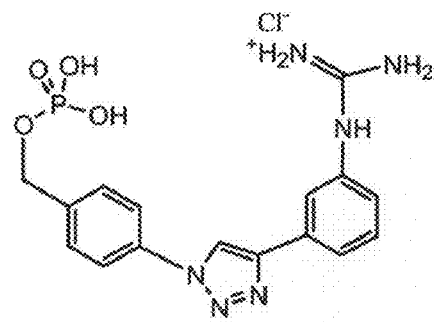
Figure 18:
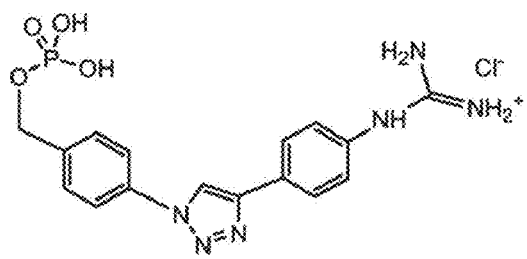
Figure 18:
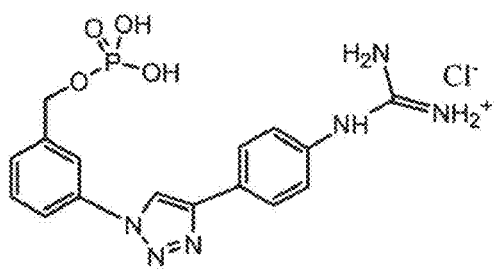
Figure 18:
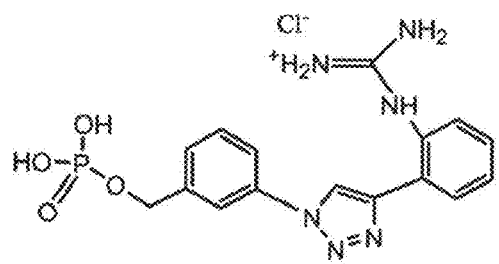
Figure 18:
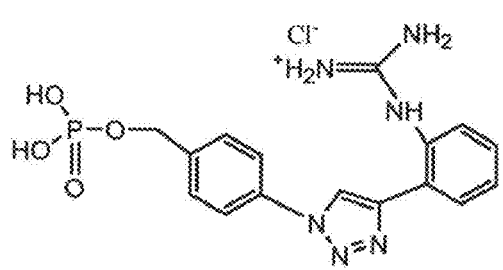

The chemical structures of representative examples of these compounds are presented in FIG. 18.

In another preferred embodiment of the present invention, the compounds described herein include one cyclic moiety such that J is a hydrocarbon chain or absent and n is 0.

Such compounds can be collectively represented by the general Formula II:

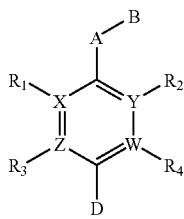

Formula II wherein:

X, Y, Z and W are each independently a carbon atom or a nitrogen atom;

A is a hydrocarbon chain or absent (corresponds to J above);

B is a negatively charged group as described hereinabove;

D is selected from the group consisting of hydrogen, alkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonamide, carbonyl, ketoester, thiocarbonyl, ester, ether, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanidino, guanidinoalkyl, amino, aminoalkyl and a hydrophobic moiety; and $R_1, R_2, R_3$ and $R_4$ are each independently selected from the group consisting of hydrogen, a lone pair of electrons, alkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonamide, carbonyl, ketoester, thiocarbonyl, ester, ether, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanylinoalkyl, guanidino, guanidinoalkyl, amino, aminoalkyl, hydrazine and an ammonium ion, or a pharmaceutically acceptable salt thereof.

It will be appreciated by one of skills in the art that the feasibility of each of the substituents (e.g., D, G, E, and $R_1-R_4$) to be located at the indicated positions depends on the valency and chemical compatibility of the substituent, the substituted position and other substituents. Hence, the present invention is aimed at encompassing all the feasible substituents for any position.

As noted hereinabove, the spacer in these family of compounds comprises a cyclic moiety and preferably an aromatic ring (aryl) or a heteroaromatic ring (heteroaryl).

In one embodiment, the spacer is a heteroaryl, such that in Formula III above, at least one of X, Y, Z and W is a nitrogen atom. As discussed hereinabove, a nitrogen atom within an aromatic ring is typically basic under neutral conditions and therefore, at a biological environment, it tends to be protonated so as to produce a positively charged =$NH^+$— group. Hence, in such a spacer, a positively charged amino moiety-containing group forms a part of the spacer. Since it was found that the amino moiety-containing group should preferably be in a certain distance from the negatively charged group, preferably, Z or W is a nitrogen atom.

In another embodiment, at least two of X, Y, Z and W are nitrogen atoms, more preferably either X and Y are nitrogen atoms or Z and W are nitrogen atoms, and even more preferably Z and W are nitrogen atoms.

As an alternative or in addition to the positively charged nitrogen atoms within the spacer, preferably at least one of $R_1, R_2, R_3$ and $R_4$ is an amino moiety-containing group, as described hereinabove.

Preferably either $R_1$ and $R_2$ or $R_3$ and $R_4$ are amino moiety-containing groups (e.g., positively charged groups).

Hence, preferred compounds according to the present invention are those having the following general Formulae IIA and IIB:

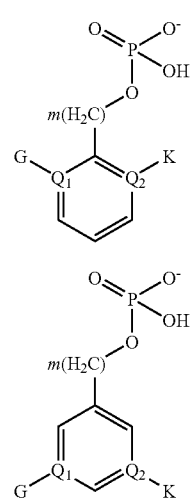

Formula IIA

Formula IIB wherein m is an integer from 1 to 6; each of $Q_1$ and $Q_2$ is independently a carbon atom or a nitrogen atom; and G and/or K are each an amino moiety-containing group (e.g., a positively charged group).

Figure 3B:
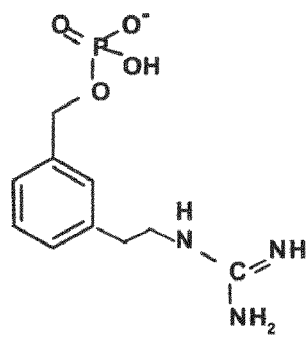
Figure 3B:
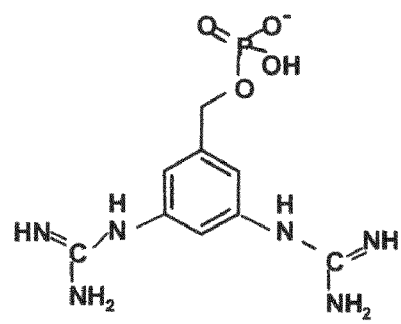
Figure 3B:
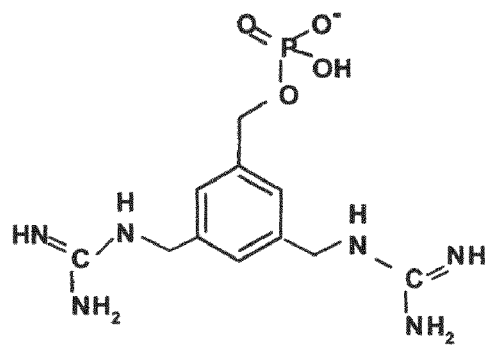
Figure 3B:
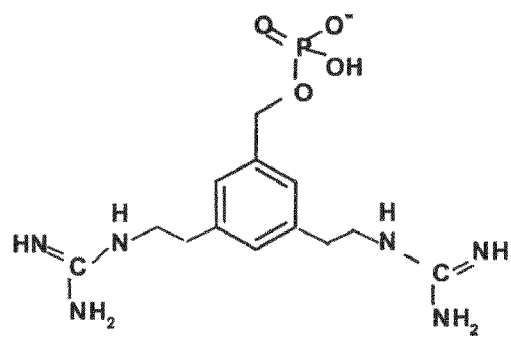

As is described above and is further demonstrated in the Examples section that follows, a number of compounds were designed according to the general formula described above, were successfully synthesized and were found to exert high inhibitory activity of the substrate binding to GSK-3. These compounds are also referred to herein, interchangeably, as GS molecules, GSC molecules or mono aryl/heteroaryl small molecules. The chemical structures of these compounds are presented in FIGS. 3a and 3b. The efficacy of these compounds as inhibitors of GSK-3 activity is presented, for example, in FIGS. 5-7, their specificity towards GSK-3 is demonstrated in Example 9, and their beneficial effect on glucose uptake in mice adipocytes is demonstrated in FIGS. 11a and 11b.

Figure 5:
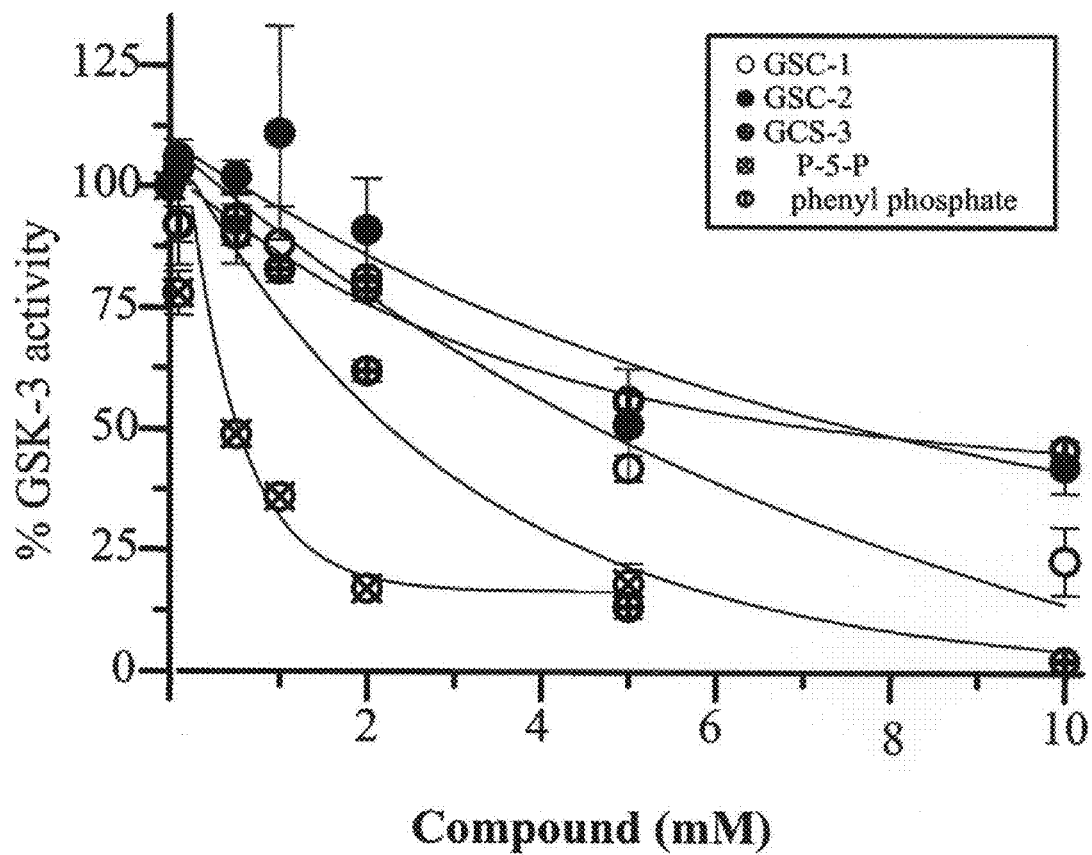
FIG. 5 presents comparative plots demonstrating the GSK-3 inhibition activity of phenyl phosphate, GSC-1, GSC-2, GSC-3 and pyridoxal phosphate (P-5-P) in in vitro inhibition assays with PGS-1 peptide substrate.
Figure 6:
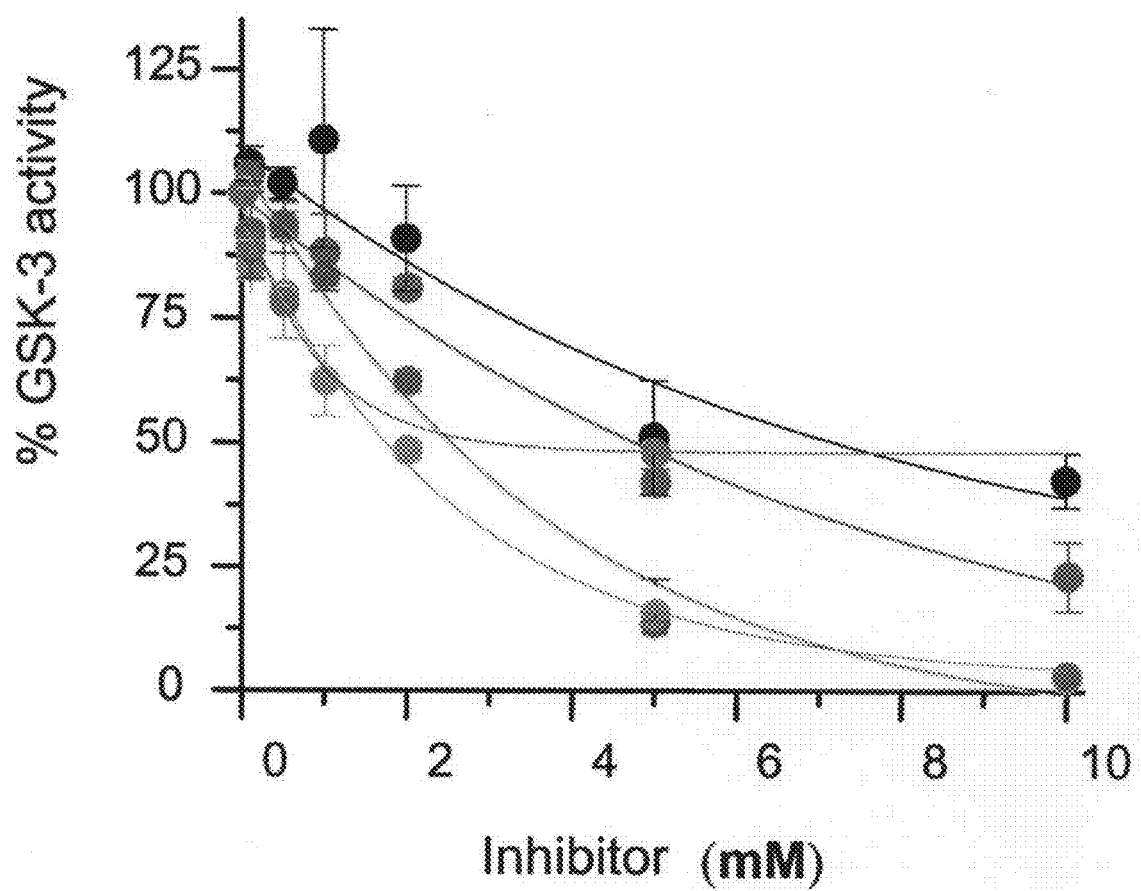
FIG. 6 presents comparative plots demonstrating the GSK-3 inhibition activity of GSC-1, GSC-2, GSC-3, GSC-4 and GS-21 in in vitro inhibition assays (Black circles denote GSC-2, red circles denote GSC-1, green circles denote GSC-3, blue circles denote GSC-4 and pink circles denote GSC-21)

As is shown in FIGS. 5-7 and in the Examples section that follows, some of the tested compounds do not have a positively charged group (e.g., GSC-1 and GSC-2, yet, these compounds exert inhibitory activity towards GSK-3. However, as is further shown in FIGS. 5-7, compounds that have a nitrogen atom within the base ring were found to be more active inhibitors, thus indicating a beneficial effect of such groups.

Hence, additional preferred compounds according to the present embodiments are compounds according to the general formula II described above, in which each of X, Y, Z and W is a carbon atom; and at least one of $R_3$ and $R_4$ is a group containing an amino moiety (e.g., a positively charged group); and D is hydrogen or alkyl. More preferred compounds are those where each of X, Y and Z is a carbon atom and W is a nitrogen atom.

It should be noted herein that although the direct or indirect attachment of a phosphate or any other negatively charged groups according to the present invention to an aromatic or heteroaromatic ring is effected via simple procedures and results in structurally simple compounds, only a limited number of such compounds have been synthesized hitherto. These include pyridoxal phosphate, benzyl phosphate, phenyl phosphate and a limited number of derivatives thereof (e.g., substituted pyridoxal phosphate, benzyl phosphate and phenyl phosphate). It is assumed that since heretofore no biological activity has been associated with such compounds, one ordinarily skilled in the art was not motivated to provide such compounds. However, the compounds according to this aspect of the invention exclude any of the presently known compounds that are embraced by the formula above.

Particularly, compounds having the following general formula A and B are excluded from the scope of this aspect of the present invention:

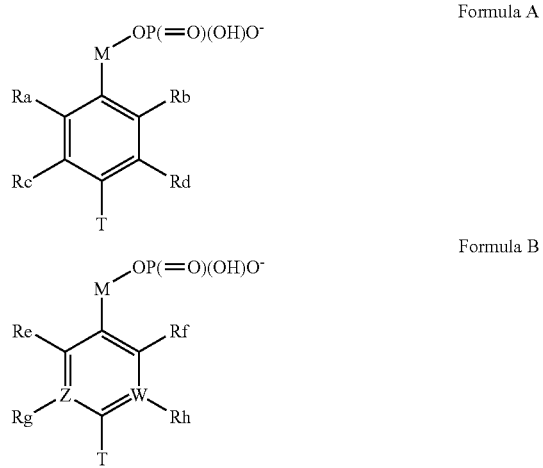

Formula A

Formula B wherein, for Formula A: M is methylene or absent; Ra, Rb and T are each hydrogen; and Rc and Rd are each independently selected from the group consisting of hydrogen, —CH=N—NH—C(=NH)—NH$_2$, —CH$_2$—N(NH$_2$)—CH$_3$ and —CH$_2$—NH—C(=NH)—OH, and for Formula B: M is methylene or absent; Z and W are each independently nitrogen or carbon, at least one of Z and W being nitrogen; and Re, Rf, Rg, Rh and T are each independently selected from the group consisting of hydrogen, nitro, alkyl, halo, hydroxy and methyl.

As is described in detail in WO 2004/052404 (PCT/IL03/10157), by one of the present inventors, it was found that attaching a hydrophobic moiety to the N-terminus of GSK-3 peptide inhibitors enhances the inhibitory activity of the peptides. Such an increased activity can be attributed to the presence of a hydrophobic patch in the enzyme, in accordance with the crystallography data reported by Dajani et al. (2001), and hence to the interaction with the peptide inhibitor with this hydrophobic patch and/or to enhancement of the membrane permeability of the peptide inhibitor due to the hydrophobic tail.

Since the phosphorylated residue in the peptide inhibitors is located at the C-terminus thereof, it is assumed that compounds according to the present invention, which include a hydrophobic moiety that is located at a distal position relative to the negatively charged group, as in the case of the peptide inhibitors, will exert enhanced inhibitory activity.

Thus, in a preferred embodiment of this aspect of the present invention, each of the compounds described herein has one or more hydrophobic moieties attached thereto. Preferably the hydrophobic moiety is attached to the spacer and further preferably, the hydrophobic moiety is attached to the spacer in such a position that would allow interaction between this moiety and a binding site of a GSK-3, as discussed hereinabove.

Thus, for example, according to this embodiment, in compounds having Formula I, at least one of J, (S)$_1$-(S)n and K comprises a hydrophobic moiety attached thereto. Preferably K has a hydrophobic moiety attached thereto. Alternatively or in addition, Sn has a hydrophobic moiety attached thereto.

In compounds having Formula II above, D is a hydrophobic moiety.

As used herein the phrase "hydrophobic moiety" refers to any substance or a residue thereof that is characterized by hydrophobicity.

As is well accepted in the art, the term "residue" describes a major portion of a substance that is covalently linked to another substance, herein the compound described hereinabove.

Hence, a hydrophobic moiety according to the present invention is preferably a residue of a hydrophobic substance, and is preferably covalently attached to the compound described hereinabove.

Representative examples of hydrophobic substances from which the hydrophobic moiety of the present invention can be derived include, without limitation, a saturated alkylene chain, an unsaturated alkylene chain, an aryl, a cycloalkyl and a hydrophobic peptide sequence, as these terms are defined herein.

As used herein, the phrase "alkylene chain" refers to a hydrocarbon linear chain, which can be saturated or unsaturated. The alkylene chain can be substituted or unsubstituted, as is described herein with respect to an alkyl group, and can be further interrupted by one or more heteroatoms such as nitrogen, oxygen, sulfur, phosphor and the like. The alkylene chain preferably includes at least 4 carbon atoms, more preferably at least 8 carbon atoms, more preferably at least 10 carbon atoms and may have up to 20, 25 and even 30 carbon atoms.

The hydrophobic moiety of the present invention can therefore comprise a residue of the hydrophobic substances described hereinabove.

A preferred example of an alkylene chain according to this aspect of the present invention is an alkylene chain that comprises a carboxy group, namely, a fatty acid residue(s).

Preferred fatty acids that are suitable for use in the context of the present invention include, without limitation, saturated or unsaturated fatty acids that have more than 10 carbon atoms, preferably between 12 and 24 carbon atoms, such as, but not limited to, myristic acid, lauric acid, palmitic acid, stearic acid, oleic acid, linoleic acid, linolenic acid, arachidonic acid and more.

Alternatively, the hydrophobic moiety, according to the present invention, can be a hydrophobic peptide sequence. The hydrophobic peptide sequence, according to the present invention, preferably includes between 2 and 15 amino acid residues, more preferably between 2 and 10 amino acid residues, more preferably between 2 and 5 amino acid residues, in which at least one amino acid residue is a hydrophobic amino acid residue.

Representative examples of hydrophobic amino acid residues include, without limitation, an alanine residue, a cysteine residue, a glycine residue, an isoleucine residue, a leucine residue, a valine residue, a phenylalanine residue, a tyrosine residue, a methionine residue, a proline residue and a tryptophan residue, or any modification thereof, as is described hereinabove.

Alternatively, the hydrophobic amino acid residue can include any other amino acid residue, which has been modified by incorporation of a hydrophobic moiety thereto.

Preferably, the hydrophobic amino acid sequence comprises at least two and more preferably at least 5 hydrophobic amino acid residues, which, further preferably, are attached to one another, so as to provide a consecutive sequence thereof within the hydrophobic amino acid sequence.

Examples of hydrophobic amino acid sequences, which are also referred to in the art interchangeably as "membrane permeable sequences" or "MPS", are found, for example, in Hagiwer (1999).

As used herein, the phrase "amino acid residue", which is also referred to herein, interchangeably, as "amino acid", describes an amino acid unit within a polypeptide chain. The amino acid residues within the hydrophobic peptide sequence can be either natural or modified amino acid residues, as these phrases are defined hereinafter.

As used herein, the phrase "natural amino acid residue" describes an amino acid residue, as this term is defined hereinabove, which includes one of the twenty amino acids found in nature.

As used herein, the phrase "modified amino acid residue" describes an amino acid residue, as this term is defined hereinabove, which includes a natural amino acid that was subjected to a modification at its side chain. Such modifications are well known in the art and include, for example, incorporation of a functionality group such as, but not limited to, a hydroxy group, an amino group, a carboxy group and a phosphate group within the side chain. This phrase therefore includes, unless otherwise specifically indicated, chemically modified amino acids, including amino acid analogs (such as penicillamine, 3-mercapto-D-valine), naturally-occurring non-proteogenic amino acids (such as norleucine), and chemically-synthesized compounds that have properties known in the art to be characteristic of an amino acid. The term "proteogenic" indicates that the amino acid can be incorporated into a protein in a cell through well-known metabolic pathways.

Accordingly, as used herein, the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids which are linked via a peptide bond or a peptide bond analog to at least one addition amino acid as this term is defined herein.

As the hydrophobic moiety provides for enhanced unpredictable activity, known compounds such as phenyl phosphate and pyridoxal phosphate and other known compounds described hereinabove, which are substituted by a hydrophobic moiety, are also included within the scope of this aspect the present invention.

Following are definitions of the various chemical moieties cited in this application.

As used herein, the term "bond" describes a single bond, a double bond or a triple bond.

As used herein, the phrase "hydrocarbon chain" and the term "hydrocarbon" describes a moiety that is mainly composed of carbon and hydrogen atoms. A hydrocarbon chain can therefore include one or more of alkyl, alkenyl, alkynyl, cycloalkyl and aryl, as these terms are defined herein, whereby each can be unsubstituted or substituted, as described herein. The hydrocarbon chain can further be interrupted by one or more heteroatoms, as defined herein.

As used herein, the term "heteroatom" describes any atom which is not carbon but which can form a covalent bond with one or more carbon atoms. Exemplary heteroatoms include, without limitation, nitrogen, oxygen, sulfur, phosphor, silicone, boron and the like.

As used herein, the term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. When substituted, the substituent group can be, for example, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonyl, sulfinyl, sulfonamide, ketoester, carbonyl, thiocarbonyl, ester, ether, thioether, thiocarbamate, urea, thiourea, O-carbamyl, N-carbamyl, O-thiocarbamyl, N-thiocarbamyl, C-amido, N-amido, C-carboxy, O-carboxy, trihalomethanesulfonamido, guanyl, guanylinoalkyl, guanidino, guanidinoalkyl, amino, aminoalkyl, hydrazine and an ammonium ion.

The term "cycloalkyl" or "alicyclic" describes an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonyl, sulfinyl, sulfonamide, ketoester, carbonyl, thiocarbonyl, ester, ether, carboxy, thiocarboxy, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanylinoalkyl, guanidino, guanidinoalkyl, amino, aminoalkyl, hydrazine and an ammonium ion.

The term "alkenyl" describes an alkyl group, as defined hereinabove, which consists of at least two carbon atoms and at least one carbon-carbon double bond.

The term "alkynyl" describes an alkyl group, as defined hereinabove, which consists of at least two carbon atoms and at least one carbon-carbon triple bond.

The term "aryl" describes an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonyl, sulfinyl, sulfonamide, ketoester, carbonyl, thiocarbonyl, ester, ether, carboxy, thiocarboxy, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanylinoalkyl, guanidino, guanidinoalkyl, amino, aminoalkyl, hydrazine and an ammonium ion.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonyl, sulfinyl, sulfonamide, ketoester, carbonyl, thiocarbonyl, ester, ether, carboxy, thiocarboxy, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanylinoalkyl, guanidino, guanidinoalkyl, amino, aminoalkyl, hydrazine and an ammonium ion.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, hydroxyalkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonyl, sulfinyl, sulfonamide, ketoester, carbonyl, thiocarbonyl, ester, ether, carboxy, thiocarboxy, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanylinoalkyl, guanidino, guanidinoalkyl, amino, aminoalkyl, hydrazine and an ammonium ion. Representative examples are piperidine, piperazine, tetrahydrofurane, tetrahydropyrane, morpholino and the like.

The term "lone pair of electrons" describes a pair of electrons that are not participating in a bond. The lone pair of electrons is present only when X, Y, Z or W is an unsubstituted nitrogen atom.

The term "hydroxy" describes an —OH group.

The term "azo" describes a —N=N group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" describes a —SH group.

The term "thioalkoxy" describes both an —S-alkyl group, and an —S-cycloalkyl group, as defined herein.

The term "thioaryloxy" describes both an —S-aryl and an —S-heteroaryl group, as defined herein.

The term "carbonyl" describes a —C(=O)—R' group, where R' is hydrogen, alkyl, alkenyl, cycloalkyl, aryl, heteroaryl (bonded through a ring carbon) or heteroalicyclic (bonded through a ring carbon) as defined herein.

The term "aldehyde" describes a carbonyl group, where R' is hydrogen.

The term "thiocarbonyl" describes a —C(=S)—R' group, where R' is as defined herein for R'.

The term "C-carboxy" describes a —C(=O)—O—R' groups, where R' is as defined herein.

The term "O-carboxy" describes an R'C(=O)—O— group, where R' is as defined herein.

The term "carboxylic acid" describes a C-carboxyl group in which R is hydrogen.

The term "halo" describes fluorine, chlorine, bromine or iodine.

The term "trihalomethyl" describes a —CX$_3$ group wherein X is a halo group as defined herein.

The term "trihalomethanesulfonyl" describes an X$_3$CS(=O)$_2$— group wherein X is a halo group as defined herein.

The term "sulfinyl" describes an —S(=O)—R' group, where R' is as defined herein.

The term "sulfonyl" describes an —S(=O)$_2$—R' group, where R' is as defined herein.

The term "S-sulfonamido" describes a —S(=O)$_2$—NR'R" group, with R' as defined herein and R" is as defined for R'.

The term "N-sulfonamido" describes an R'S(=O)$_2$—NR" group, where R' and R" are as defined herein.

The term "trihalomethanesulfonamido" describes an X$_3$CS(=O)$_2$NR'— group, where R' and X are as defined herein.

The term "O-carbamyl" describes an —OC(=O)—NR'R" group, where R' and R" are as defined herein.

The term "N-carbamyl" describes an R"OC(=O)—NR'— group, where R' and R" are as defined herein.

The term "O-thiocarbamyl" describes an —OC(=S)—NR'R" group, where R' and R" are as defined herein.

The term "N-thiocarbamyl" describes an R"OC(=S)NR'— group, where R' and R" are as defined herein.

The term "amino" describes an —NR'R" group where R' and R" are as defined herein.

The term "aminoalkyl" describes an alkyl, as defined hereinabove, substituted by an amino group. Preferably, the alkyl terminates by the amino group.

The term "C-amido" describes a —C(=O)—NR'R" group, where R' and R" are as defined herein.

The term "N-amido" describes an R'C(=O)—NR" group, where R' and R" are as defined herein.

The term "urea" describes an —NR'C(=O)—NR"R'" group, where R' and R" are as defined herein and R'" is defined as either R' or R".

The term "guanidino" describes an —R'NC(=NR"")—NR"R'" group, where R', R" and R'" are as defined herein and R"" is defined as either R', R" or R'".

The term "guanidinoalkyl" describes an alkyl group substituted by a guanidino group, as these terms are defined herein. Preferably, the alkyl group terminates by the guanidino group.

The term "guanyl" describes an R'R"NC(=NR"")— group, where R', R", R'" and R"" are as defined herein.

The term "guanyloalkyl" describes an alkyl group substituted by a guanyl group, as these terms are defined herein. Preferably, the alkyl group terminates by the guanyl group.

The term "nitro" describes a —NO$_2$ group.

The term "cyano" describes a —C≡N group.

The term "ketoester" describes a —C(=O)—C(=O)—O— group.

The term "thiourea" describes a —NR'—C(=S)—NR'— group, with R' and R" as defined hereinabove.

The term "hydrazine" describes a NR'—NR" group, with R' and R" as defined hereinabove.

The term "ammonium ion" describes a —(NR'R"R''')+, where R', R" and R''' as defined hereinabove.

The term "guanidinium ion" describes a —(R'NC(=NR'''')—NR"R'''R'''')+ group, where R', R", R''' and R'''' are as defined herein.

The present invention further encompasses pharmaceutically acceptable salts of the compounds described herein.

The phrase "pharmaceutically acceptable salt" refers to a charged species of the parent compound and its counter ion. An example, without limitation, of a pharmaceutically acceptable salt would be a compound that comprises an ammonium or guanidinium cation and an anion of an acid such as, for example, HCl, trifluoroacetic acid (TFA) and the like. As is discussed hereinabove and is further demonstrated in the Examples section that follows, each of the compounds described hereinabove is designed based on the three-dimensional structure of a GSK-3 substrate and is therefore potential substrate competitive inhibitor of GSK-3 activity.

Hence, according to still another aspect of the present invention, there is provided a method of inhibiting an activity of GSK-3, which is effected by contacting cells expressing GSK-3 with an inhibitory effective amount of any one of the compounds described hereinabove.

As used herein, the term "inhibitory effective amount" is the amount determined by such considerations as are known in the art, which is sufficient to inhibit the activity of GSK-3. The activity can be a phosphorylation and/or autophosphorylation activity of GSK-3.

The method according to this aspect of the present invention can be effected by contacting the cells with the compounds in vitro and/or in vivo. This method can be further effected by further contacting the cells with an additional active ingredient that is capable of altering an activity of GSK-3, as is detailed hereinbelow.

The inhibition of GSK-3 activity is a way to increase insulin activity in vivo. High activity of GSK-3 impairs insulin action in intact cells (Eldar-Finkelman et al, 1997). This impairment results from the phosphorylation of insulin receptor substrate-1 (IRS-1) serine residues by GSK-3. Studies performed in patients with type II diabetes (non-insulin dependent diabetes mellitus, NIDDM) show that glycogen synthase activity is markedly decreased in these patients, and that decreased activation of protein kinase B (PKB), an upstream regulator of GSK-3, by insulin is also detected (Shulman et al, (1990); Cross et al, (1995). Mice susceptible to high fat diet-induced diabetes and obesity have significantly increased GSK-3 activity in epididymal fat tissue (Eldar-Finkelman et al, 1999). Increased GSK-3 activity expressed in cells resulted in suppression of glycogen synthase activity (Eldar-Finkelman et al, 1996).

Inhibition of GSK-3 activity therefore provides a useful method for increasing insulin activity in insulin-dependent conditions. Thus, according to yet another aspect of the present invention there is provided a method of potentiating insulin signaling, which is effected by contacting insulin responsive cells with an effective amount, as is defined hereinabove, of any one of the compounds described hereinabove.

As used herein, the phrase "potentiating insulin signaling" includes an increase in the phosphorylation of insulin receptor downstream components and an increase in the rate of glucose uptake as compared with glucose uptake in untreated subjects or cells.

The method according to this aspect of the present invention can be effected by contacting the cells with the compound of the present embodiments, in vitro or in vivo, and can be also effected by further contacting the cells with insulin.

Potentiation of insulin signaling, in vivo, resulting from administration of the compounds described herein, can be monitored as a clinical endpoint. In principle, the easiest way to look at insulin potentiation in a patient is to perform the glucose tolerance test. After fasting, glucose is given to a patient and the rate of the disappearance of glucose from blood circulation (namely glucose uptake by cells) is measured by assays well known in the art. Slow rate (as compared to healthy subject) of glucose clearance will indicate insulin resistance. The administration of an inhibitor to an insulin-resistant patient increases the rate of glucose uptake as compared with a non-treated patient. The inhibitor may be administered to an insulin resistant patient for a longer period of time, and the levels of insulin, glucose, and leptin in blood circulation (which are usually high) may be determined. Decrease in glucose levels will indicate that the inhibitor potentiated insulin action. A decrease in insulin and leptin levels alone may not necessarily indicate potentiation of insulin action, but rather will indicate improvement of the disease condition by other mechanisms.

The compounds described hereinabove, can be effectively utilized for treating any biological condition that is associated with GSK-3.

Hence, according to an additional aspect of the present invention, there is provided a method of treating a biological condition associated with GSK-3 activity. The method, according to this aspect of the present invention, is effected by administering to a subject in need thereof a therapeutically effective amount of the any of the compounds described hereinabove.

The phrase "biological condition associated with GSK-3 activity" as used herein includes any biological or medical condition or disorder in which effective GSK-3 activity is identified, whether at normal or abnormal levels. The condition or disorder may be caused by the GSK-3 activity or may simply be characterized by GSK-3 activity. That the condition is associated with GSK-3 activity means that some aspect of the condition can be traced to the GSK-3 activity.

Herein, the term "treating" includes abrogating, substantially inhibiting, slowing or reversing the progression of a condition or disorder, substantially ameliorating clinical symptoms of a condition or disorder or substantially preventing the appearance of clinical symptoms of a condition or disorder. These effects may be manifested, for example, by a decrease in the rate of glucose uptake with respect to type II diabetes or by halting neuronal cell death with respect to neurodegenerative disorders, as is detailed hereinbelow.

The term "administering" as used herein describes a method for bringing the compound of the present invention and cells affected by the condition or disorder together in such a manner that the compound can affect the GSK-3 activity in these cells. The compounds of the present invention can be administered via any route that is medically acceptable. The route of administration can depend on the disease, condition or injury being treated. Possible administration routes include injections, by parenteral routes, such as intravascular, intravenous, intra-arterial, subcutaneous, intramuscular, intratumor, intraperitoneal, intraventricular, intraepidural, intracerebrovascular or others, as well as oral, nasal, ophthalmic, rectal, topical, or by inhalation. Sustained release administration is also specifically included in the invention, by such means as depot injections or erodible implants. Administration can also be intra-articularly, intrarectally, intraperitoneally, intramuscularly, subcutaneously, or by aerosol inhalant. Where treatment is systemic, the compound can be administered orally or parenterally, such as intravenously, intramuscularly, subcutaneously, intraorbitally, intracapsularly, intraperitoneally or intracisternally, as long as provided in a composition suitable for effecting the introduction of the compound into target cells, as is detailed hereinbelow.

The phrase "therapeutically effective amount", as used herein, describes an amount administered to an individual, which is sufficient to abrogate, substantially inhibit, slow or reverse the progression of a condition associated with GSK-3 activity, to substantially ameliorate clinical symptoms of a such a condition or substantially prevent the appearance of clinical symptoms of such a condition. The GSK-3 activity can be a GSK-3 kinase activity. The inhibitory amount may be determined directly by measuring the inhibition of a GSK-3 activity, or, for example, where the desired effect is an effect on an activity downstream of GSK-3 activity in a pathway that includes GSK-3, the inhibition may be measured by measuring a downstream effect. Thus, for example where inhibition of GSK-3 results in the arrest of phosphorylation of glycogen synthase, the effects of the compound may include effects on an insulin-dependent or insulin-related pathway, and the compound may be administered to the point where glucose uptake is increased to optimal levels. Also, where the inhibition of GSK-3 results in the absence of phosphorylation of a protein that is required for further biological activity, for example, the tau protein, then the compound may be administered until polymerization of phosphorylated tau protein is substantially arrested. Therefore, the inhibition of GSK-3 activity will depend in part on the nature of the inhibited pathway or process that involves GSK-3 activity, and on the effects that inhibition of GSK-3 activity has in a given biological context.

The amount of the compound that will constitute an inhibitory amount will vary depending on such parameters as the compound and its potency, the half-life of the compound in the body, the rate of progression of the disease or biological condition being treated, the responsiveness of the condition to the dose of treatment or pattern of administration, the formulation, the attending physician's assessment of the medical situation, and other relevant factors, and in general the health of the patient, and other considerations such as prior administration of other therapeutics, or co-administration of any therapeutic that will have an effect on the inhibitory activity of the compound or that will have an effect on GSK-3 activity, or a pathway mediated by GSK-3 activity. It is expected that the inhibitory amount will fall in a relatively broad range that can be determined through routine trials.

As is discussed in detail hereinabove, GSK-3 is involved in various biological pathways and hence, the method according to this aspect of the present invention can be used in the treatment of a variety of biological conditions, as is detailed hereinunder.

GSK-3 is involved in the insulin signaling pathway and therefore, in one example, the method according this aspect of the present invention can be used to treat any insulin-dependent condition.

As GSK-3 inhibitors are known to inhibit differentiation of pre-adipocytes into adipocytes, and therefore, in another example, the method of this aspect of the present invention can be used to treat obesity.

In yet another example, the method according to this aspect of the present invention can be used to treat diabetes and particularly, non-insulin dependent diabetes mellitus.

Diabetes mellitus is a heterogeneous primary disorder of carbohydrate metabolism with multiple etiologic factors that generally involve insulin deficiency or insulin resistance or both. Type I, juvenile onset, insulin-dependent diabetes mellitus, is present in patients with little or no endogenous insulin secretory capacity. These patients develop extreme hyperglycemia and are entirely dependent on exogenous insulin therapy for immediate survival. Type II, or adult onset, or non-insulin-dependent diabetes mellitus, occurs in patients who retain some endogenous insulin secretory capacity, but the great majority of them are both insulin deficient and insulin resistant. Approximately 95% of all diabetic patients in the United States have non-insulin dependent, Type II diabetes mellitus (NIDDM), and, therefore, this is the form of diabetes that accounts for the great majority of medical problems. Insulin resistance is an underlying characteristic feature of NIDDM and this metabolic defect leads to the diabetic syndrome. Insulin resistance can be due to insufficient insulin receptor expression, reduced insulin-binding affinity, or any abnormality at any step along the insulin signaling pathway (see U.S. Pat. No. 5,861,266).

The compounds of the present invention can be used to treat type II diabetes in a patient with type II diabetes as follows: a therapeutically effective amount of the compound is administered to the patient, and clinical markers, e.g., blood sugar level, are monitored. The compounds of the present invention can further be used to prevent type II diabetes in a subject as follows: a prophylactically effective amount of the compound is administered to the patient, and a clinical marker, for example IRS-1 phosphorylation, is monitored.

Treatment of diabetes is determined by standard medical methods. A goal of diabetes treatment is to bring sugar levels down to as close to normal as is safely possible. Commonly set goals are 80-120 milligrams per deciliter (mg/dl) before meals and 100-140 mg/dl at bedtime. A particular physician may set different targets for the patent, depending on other factors, such as how often the patient has low blood sugar reactions. Useful medical tests include tests on the patient's blood and urine to determine blood sugar level, tests for glycated hemoglobin level (HbA$_{1c}$; a measure of average blood glucose levels over the past 2-3 months, normal range being 4-6%), tests for cholesterol and fat levels, and tests for urine protein level. Such tests are standard tests known to those of skill in the art (see, for example, American Diabetes Association, 1998). A successful treatment program can also be determined by having fewer patients in the program with diabetic eye disease, kidney disease, or nerve disease.

Hence, in one particular embodiment of the method according to this aspect of the present invention, there is provided a method of treating non-insulin dependent diabetes mellitus: a patient is diagnosed in the early stages of non-insulin dependent diabetes mellitus. A compound of the present invention is formulated in an enteric capsule. The patient is directed to take one tablet after each meal for the purpose of stimulating the insulin signaling pathway, and thereby controlling glucose metabolism to levels that obviate the need for administration of exogenous insulin As is further discussed hereinabove, and has been demonstrated in WO 2004/052404, GSK-3 inhibition is associated with affective disorders. Therefore, in another example, the method according to this aspect of the present invention can be used to treat affective disorders such as unipolar disorders (e.g., depression) and bipolar disorders (e.g., manic depression).

As GSK-3 is also considered to be an important player in the pathogenesis of neurodegenerative disorders and diseases, the method according to this aspect of the present invention can be further used to treat a variety of such disorders and diseases.

In one example, since inhibition of GSK-3 results in halting neuronal cell death, the method according to this aspect of the present invention can be used to treat a neurodegenerative disorder that results from an event that cause neuronal cell death. Such an event can be, for example, cerebral ischemia, stroke, traumatic brain injury or bacterial infection.

In another example, since GSK-3 activity is implicated in various central nervous system disorders and neurodegenerative diseases, the method according to this aspect of the present invention can be used to treat various chronic neurodegenerative diseases such as, but not limited to, Alzheimer's disease, Huntington's disease, Parkinson's disease, AIDS associated dementia, amyotrophic lateral sclerosis (AML) and multiple sclerosis.

As is discussed hereinabove, GSK-3 activity has particularly been implicated in the pathogenesis of Alzheimer's disease. Hence, in one representative embodiment of the method according to this aspect of the present invention, there is provided a method of treating a patient with Alzheimer's disease: A patient diagnosed with Alzheimer's disease is administered with a compound of the present invention, which inhibits GSK-3-mediated tau hyperphosphorylation, prepared in a formulation that crosses the blood brain barrier (BBB). The patient is monitored for tau phosphorylated polymers by periodic analysis of proteins isolated from the patient's brain cells for the presence of phosphorylated forms of tau on an SDS-PAGE gel known to characterize the presence of and progression of the disease. The dosage of the compound is adjusted as necessary to reduce the presence of the phosphorylated forms of tau protein.

GSK-3 has also been implicated with respect to psychotic disorders such as schizophrenia, and therefore the method according to this aspect of the present invention can be further used to treat psychotic diseases or disorders, such as schizophrenia.

The method according to this aspect of the present invention can be further effected by co-administering to the subject one or more additional active ingredient(s) which is capable of modulating an activity of GSK-3.

As used herein, "co-administering" describes administration of a compound according to the present invention in combination with the additional active ingredient(s) (also referred to herein as active or therapeutic agent). The additional active agent can be any therapeutic agent useful for treatment of the patient's condition. The co-administration may be simultaneous, for example, by administering a mixture of the compound and the therapeutic agents, or may be accomplished by administration of the compound and the active agents separately, such as within a short time period. Co-administration also includes successive administration of the compound and one or more of another therapeutic agent. The additional therapeutic agent or agents may be administered before or after the compound. Dosage treatment may be a single dose schedule or a multiple dose schedule.

The additional active ingredient can be insulin.

Preferably, the additional active ingredient is capable of inhibiting an activity of GSK-3, such that the additional active ingredient according to the present invention can be any GSK-3 inhibitor other than the compounds of the present invention, e.g., a short peptide GSK-3 inhibitor as described in WO 01/49709, WO 2004/052404 and U.S. Pat. No. 6,780,625. Alternatively, the GSK-3 inhibitor can be, for example, lithium, valproic acid and/or lithium ion.

Alternatively, the additional active ingredient can be an active ingredient that is capable of downregulating an expression of GSK-3.

An agent that downregulates GSK-3 expression refers to any agent which affects GSK-3 synthesis (decelerates) or degradation (accelerates) either at the level of the mRNA or at the level of the protein. For example, a small interfering polynucleotide molecule which is designed to down regulate the expression of GSK-3 can be used as an additional active ingredient according to this embodiment of the present invention.

An example for a small interfering polynucleotide molecule which can down-regulate the expression of GSK-3 is a small interfering RNA or siRNA, such as, for example, the morpholino antisense oligonucleotides described by in Munshi et al. (Munshi C B, Graeff R, Lee H C, *J Biol Chem* 2002 Dec. 20; 277(51):49453-8), which includes duplex oligonucleotides which direct sequence specific degradation of mRNA through the previously described mechanism of RNA interference (RNAi) (Hutvagner and Zamore (2002) Curr. Opin. Genetics and Development 12:225-232).

As used herein, the phrase "duplex oligonucleotide" refers to an oligonucleotide structure or mimetics thereof, which is formed by either a single self-complementary nucleic acid strand or by at least two complementary nucleic acid strands. The "duplex oligonucleotide" of the present invention can be composed of double-stranded RNA (dsRNA), a DNA-RNA hybrid, single-stranded RNA (ssRNA), isolated RNA (i.e., partially purified RNA, essentially pure RNA), synthetic RNA and recombinantly produced RNA.

Preferably, the specific small interfering duplex oligonucleotide of the present invention is an oligoribonucleotide composed mainly of ribonucleic acids.

Instructions for generation of duplex oligonucleotides capable of mediating RNA interference are provided in www.ambion.com.

Hence, the small interfering polynucleotide molecule according to the present invention can be an RNAi molecule (RNA interference molecule).

Alternatively, a small interfering polynucleotide molecule can be an oligonucleotide such as a GSK-3-specific antisense molecule or a rybozyme molecule, further described hereinunder.

Antisense molecules are oligonucleotides, which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target polynucleotide. An additional region of the oligonucleotide may serve as a substrate for enzymes capable of cleaving RNA:DNA or RNA:RNA hybrids. An example for such includes RNase H, which is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

The antisense molecules of the present invention may be formed as composite structures of two or more oligonucleotides, modified oligonucleotides, as described above. Representative U.S. patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein fully incorporated by reference.

Rybozyme molecules are being increasingly used for the sequence-specific inhibition of gene expression by the cleavage of mRNAs. Several rybozyme sequences can be fused to the oligonucleotides of the present invention. These sequences include but are not limited ANGIOZYME specifically inhibiting formation of the VEGF-R (Vascular Endothelial Growth Factor receptor), a key component in the angiogenesis pathway, and HEPTAZYME, a rybozyme designed to selectively destroy Hepatitis C Virus (HCV) RNA, (Rybozyme Pharmaceuticals, Incorporated—WEB home page).

Further alternatively, a small interfering polynucleotide molecule, according to the present invention can be a DNAzyme.

DNAzymes are single-stranded catalytic nucleic acid molecules. A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, L M Curr Opin Mol Ther 2002; 4: 119-21).

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al., 20002, Abstract 409, Ann Meeting Am Soc Gen Ther www.asgt.org). In another application, DNAzymes complementary to bcr-abl oncogenes were successful in inhibiting the oncogenes expression in leukemia cells, and lessening relapse rates in autologous bone marrow transplant in cases of CML and ALL.

Oligonucleotides designed according to the teachings of the present invention can be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art.

While being potent therapeutic agents, and since therapeutic applications often require administration of effective amounts of an active ingredient to a treated individual, the compounds described herein are preferably included, as active ingredients, in a pharmaceutical composition which further comprises a pharmaceutically acceptable carrier for facilitating administration of a compound to the treated individual and possibly to facilitate entry of the active ingredient into the targeted tissues or cells.

Hence, according to still an additional aspect of the present invention there is provided a pharmaceutical composition which comprises, as an active ingredient, any of the compounds described herein and a pharmaceutically acceptable carrier.

Hereinafter, the phrases "pharmaceutically acceptable carrier" and "physiologically acceptable carrier" refer to a carrier or a diluent that does not cause significant irritation to a subject and does not abrogate the biological activity and properties of the administered compound. Examples, without limitations, of carriers are propylene glycol, saline, emulsions and mixtures of organic solvents with water.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

The pharmaceutical acceptable carrier can further include other agents such as, but not limited to, absorption delaying agents, antibacterial agents, antifungal agents, antioxidant agents, binding agents, buffering agents, bulking agents, cationic lipid agents, coloring agents, diluents, disintegrants, dispersion agents, emulsifying agents, excipients, flavoring agents, glidants, isotonic agents, liposomes, microcapsules, solvents, sweetening agents, viscosity modifying agents, wetting agents, and skin penetration enhancers.

Techniques for formulation and administration of drugs may be found in "Remington's Pharmaceutical Sciences," Mack Publishing Co., Easton, Pa., latest edition, which is incorporated herein by reference. Suitable routes of administration may, for example, include oral, rectal, transmucosal, transdermal, intestinal or parenteral delivery, including intramuscular, subcutaneous and intramedullary injections as well as intrathecal, direct intraventricular, intravenous, intraperitoneal, intranasal, or intraocular injections.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the compound into preparations which can be used pharmaceutically. The composition can be formulated in a delivery form such as an aerosol delivery form, aqueous solution, bolus, capsule, colloid, delayed release, depot, dissolvable powder, drops, emulsion, erodible implant, gel, gel capsule, granules, injectable solution, ingestible solution, inhalable solution, lotion, oil solution, pill, suppository, salve, suspension, sustained release, syrup, tablet, tincture, topical cream, transdermal delivery form. Proper formulation is dependent upon the route of administration chosen.

For injection, the compound of the invention may be formulated in aqueous solutions, preferably in physiologically compatible buffers such as Hank's solution, Ringer's solution, or physiological saline buffer with or without organic solvents such as propylene glycol, polyethylene glycol. For transmucosal administration, penetrants are used in the formulation. Such penetrants are generally known in the art.

For oral administration, the compound can be formulated readily by combining the compound with pharmaceutically acceptable carriers well known in the art. Such carriers enable the compound of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active ingredient doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the compound according to the present invention is conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the ingredient and a suitable powder base such as lactose or starch.

The compound described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the compound in water-soluble form. Additionally, suspensions of the compound may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredient to allow for the preparation of highly concentrated solutions.

Alternatively, the compound may be in powder form for constitution with a suitable vehicle, e.g., sterile, pyrogen-free water, before use.

The compound of the present invention may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include compositions wherein the compound is contained in an amount effective to achieve the intended purpose. More specifically, a therapeutically effective amount means an amount of a compound effective to affect symptoms of a condition or prolong the survival of the subject being treated.

Determination of a therapeutically effective amount is well within the capability of those skilled in the art, especially in light of the detailed disclosure provided herein.

For any active ingredient used in the methods of the invention, the therapeutically effective amount or dose can be estimated initially from activity assays in cell cultures and/or animals. Such information can be used to more accurately determine useful doses in humans.

The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Compositions of the present invention may, if desired, be presented in a pack or dispenser device, such as a FDA approved kit, which may contain one or more unit dosage forms containing the compound. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include, for example, any of the biological conditions associated with GSK-3 activity listed hereinabove.

Hence, the pharmaceutical composition of the present invention can be packaged in a packaging material and identified in print, on or in the packaging material, for use in the treatment or prevention of a biological condition associated with GSK-3.

The pharmaceutical composition of the present invention can further comprises an additional active ingredient that is capable of modulating an activity of GSK-3, as is described hereinabove.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above description, illustrate the invention in a non-limiting fashion.

Materials

Peptides were synthesized by Genemed Synthesis Inc. (San Francisco, Calif.).

Radioactive materials were purchased from Amersham Ltd.

Phenyl phosphate and pyridoxal phosphate (also referred to herein as P-5-P) were obtained from Sigma (Israel).

All other reagents and solvents were obtained from commercial sources (e.g., Sigma, Acros, Aldrich) and were used as supplied, unless otherwise indicated.

GSC-1, GSC-2 and GSC-3 were synthesized according to procedures known in the art, as is detailed hereinunder.

Syntheses of the novel compounds GSC-4, GSC-5, GSC-6, GSC-7 and GSC-21 were designed and practiced as described hereinbelow.

Syntheses of the novel compounds MP1-MP6 were designed and practiced as described hereinbelow.

Example 1

Determination of a 3D Structure of a GSK-3 Substrate by NMR Spectroscopy and Structure Calculations Based Thereon Tested Peptides:

A small phosphorylated peptide patterned after the known GSK-3 substrate CREB, denoted p9CREB, and two additional peptides, a non-phosphorylated peptide, 9CREB, and a variant where $S^1$ was replaced with glutamic acid (which is thought to mimic a charged group), 9ECREB, were used in these studies and are listed in Table 1 below.

TABLE 1

| Peptide | Sequence | SEQ ID NO: |
|---------|----------|------------|
| p9CREB  | ILSRRPS(p)YR | 2 |
| 9CREB   | ILSRRPSYR | 3 |
| 9ECREB  | ILSRRPEYR | 4 |

Time course analyses of peptide phosphorylation by GSK-3 confirmed that only the phosphorylated peptide, p9CREB, was a substrate for GSK-3, while 9CREB and 9ECREB completely failed to be phosphorylated by GSK-3, thus indicating again that phosphorylated serine is an absolute requirement for GSK-3.

Determination of the 3D Structures of the Tested Peptides:

Determination of the 3D structures of p9CREB (FIG. 1a), 9CREB (FIG. 1b) and 9ECREB (not shown) by 2D $^1$H NMR spectroscopy was performed using the following procedures:

A solution of each peptide was prepared by dissolving lyophilized powder in water containing 10% $D_2O$. 2D-NMR spectra were acquired at the $^1$H proton frequency of 600.13 MHz on a Bruker Advance DMX spectrometer. The carrier frequency was set on the water signal and it was suppressed by applying either a WATERGATE method or by low-power irradiation during the relaxation period. The experimental temperature (280° K) was optimized in order to reduce population averaging due to the fast exchange at more ambient temperatures, while preserving the best possible spectral resolution. All experiments were carried out in the phase sensitive mode (TPPI or States-TPPI) and recorded with a spectral width of 12 ppm, with 4K real $t_2$ data points and 512 $t_1$-increments. Two-dimensional homonuclear data collected included TOCSY using a MLEV pulse sequence with a mixing time of 150 msec, and NOESY experiments with mixing times ranging between 100 and 750 msecs. Typically, the relaxation delays were 1.5 and 2.0 sec in TOCSY and NOESY experiments, respectively. In the ROESY measurements, the duration of the spin-lock was set to 400 msec with a power of 3.4 KHz. All spectra were calibrated versus tetramethylsilane.

The data was processed using Bruker XWINNMR software (Bruker Analytische Messtechnik, GmbH, version 2.7). All data processing, calculations and analysis were done on Silicon Graphics workstations (INDY R4000 and INDIGO2 R10000). Zero filling of the indirect dimension and apodization of the free induction decay by a shifted squared-sine window function on both dimensions were applied prior to Fourier transformation to enhance spectral resolution. The spectra were further phase-corrected by applying an automatic polynomial baseline correction developed by Bruker.

Resonance assignment was based on the TOCSY and NOESY spectra measured at the same experimental conditions, according to the sequential assignment methodology developed by Wüthrich using the Bruker software program AURELIA (Bruker Analytic GmbH, version 2.7).

The NOE distance restraints were derived from NOESY spectra recorded at 450 msec. This optimal mixing time was determined for the p9CREB peptide sample by comparing the NOE signal intensities in a series of experiments with mixing times varying from 100 msec to 750 msec. The chosen mixing time gave maximal NOE buildup with no significant contribution from spin diffusion. This value was used for the non-phosphorylated analog experiment in order to maintain identical experimental conditions. Integrated peak volumes were converted into distance restraints using a $r^{-6}$ dependency and the known distance of 2.47 Å between the two adjacent protons of the tyrosine aromatic ring was used for calibration. The restraints were classified into strong (1.8-2.5 Å), medium (1.8-3.5 Å) and weak (1.8-5.0 Å). An empirical correction of 0.5 Å was added to the upper bound for restraints involving methyl groups.

The structures were calculated by hybrid distance geometry—dynamical simulated annealing using XPLOR (version 3.856). The NOE energy was introduced as a square-well potential with a constant force constant of 50 Kcal/mol·Å$^2$. Simulated annealing consisted of 1500 3 fsec steps at 1000 K and 3000 1 fsec steps during cooling to 300 K. Finally, the structures were minimized using conjugate gradient energy minimization for 4000 iterations. INSIGHTII (Molecular Modeling System version 97.0, Molecular Simulations, Inc.) was used for visualization and analysis of the NMR-derived structures. Their quality was assessed using PROCHECK.

Results:

Tables 2 and 3 below present the structural coordinate data that was used for inputting into structure analysis software for visualization of the 3D structures.

From the obtained 3D structures, presented in FIGS. 1a and 1b, it was observed that only the phosphorylated peptide has a defined structural conformation. As is shown in FIG. 1a, for p9CREB, the phosphorylation imposed a significant "turn" of the peptide backbone, bringing Tyr 8 and Arg 4 closer, and forming a 'loop structure' whereby the phosphorylated residue is pointing out of the loop. This conformation minimizes on the one hand interference of positively charged residues (Arg 4 and Arg 5) with the catalytic binding pocket of the enzyme, and on the other hand, renders the phosphorylated serine readily accessible to the enzyme. This structure analysis provides an explanation for the unique substrate recognition of GSK-3. The design of small molecules that mimic the structure presented here thus provides a method for obtaining selective inhibitors for GSK-3.

Example 2

Chemical Syntheses of Mono Aryl/Heteroaryl GSK-3 Inhibitors (GSC Small Molecules)

Instrumental Data:

Proton, carbon, fluorine and phosphorus nuclear magnetic resonance spectra were obtained on either a Bruker AMX 500 spectrometer or a Brucker AV 300 spectrometer and are reported in ppm (δ). Tetramethylsilane (TMS) was used as an internal standard for proton spectra, phosphoric acid was used as an internal standard for phosphorus spectra and the solvent peak was used as the reference peak for carbon and fluorine spectra.

Mass spectra were obtained on a Finnigan LCQ Duo LC-MS ion trap electrospray ionization (ESI) mass spectrometer.

Thin-layer chromatography (TLC) was performed using Analtech silica gel plates and visualized by ultraviolet (UV) light, or by staining the plates in 0.2 wt % ninhydrine in butanol.

Elemental analysis was performed by Quantitative Technologies, Inc. (Whitehouse, N.J.).

HPLC analyses were obtained using a Hypersil BDS C18 Column, 4.6×150 mm, 5 μm, at ambient column temperature and with a detector operating at 220 nm, using, as a mobile phase, a standard solvent gradient program, as follows:

| Time (Minutes) | Flow (ml/min) | % A | % B |
|---|---|---|---|
| 0.0 | 1.0 | 100 | 0.0 |
| 4.0 | 1.0 | 100 | 0.0 |
| 20.0 | 1.0 | 92.0 | 8.0 |
| 21.0 | 1.0 | 100 | 0.0 |
| 22.0 | 1.0 | 100 | 0.0 |

A = 0.1% TFA in water
B = 0.1% TFA in acetonitrile

Preparation of GSK-3 Inhibitors:

Based on the 3D structure determination described hereinabove, a series of small molecules that serve as potential selective inhibitors of GSK-3 has been designed and successfully prepared, as follows.

A. Synthesis of p-methyl benzyl phosphate (GSC-2)

The general pathway of the synthesis of GSC-2 is depicted in Scheme 1 below.

Scheme 1

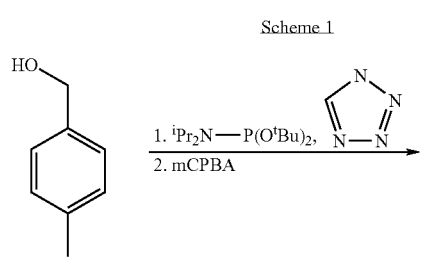

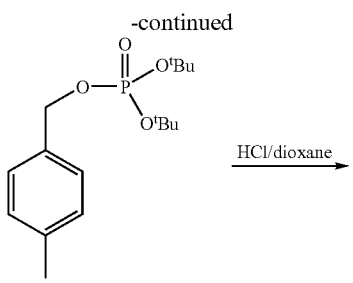

Preparation of di-tert-butyl, p-methyl benzyl phosphate: 1H-Tetrazole solution (0.45 M in acetonitrile, 20 ml, 9 mmol, 3 equivalents) was added in one portion to a stirred solution of 4-methylbenzyl alcohol (0.4 gram, 3.3 mmol, 1.1 equivalent) and di-tert-butyl diisopropyl phosphoramidite (0.95 ml, 0.83 gram, 3 mmol, 1 equivalent) in dry THF (3 ml). The mixture was stirred for 15 minutes at 20° C. The mixture was cooled to −40° C. (by means of dry ice/acetonitrile), and a solution of 85% m-chloroperbenzoic acid (mCPBA) (0.81 gram in 1 ml dichloromethane, 4 mmol, 1.3 equivalents) in dichloromethane (4 ml) was rapidly added while the reaction temperature was kept below 0° C. The solution was allowed to warm up to room temperature and after stirring for 5 minutes at 20° C., 10% aqueous NaHSO$_3$ (10 ml) was added and the mixture was stirred for a further 10 minutes. The mixture was then extracted with ether (70 ml) and the aqueous phase discarded. The ethereal phase was washed with 10% aqueous NaHSO$_3$ (2×20 ml), 5% saturated aqueous NaHCO$_3$ (2×20 ml), dried on sodium sulfate and filtered. The organic filtrate was evaporated and the residue was purified by chromatography on a silica gel column, using a mixture of EtOAc/hexanes 1:15 as eluent, to give a mixture of the product (di-tert-butyl, p-methyl benzyl phosphate) and the starting material, which was used without further separation.

$^1$H NMR (200 MHz, CDCl$_3$): δ=7.22 (m, 4H, Ar), 4.93 (d, J=7.22 Hz, 2H, CH$_2$O), 2.33 (s, 3H, CH$_3$), 1.46 (s, 18H, OtBu).

$^{13}$C NMR (50.4 MHz, CDCl$_3$): δ=137.7 (Ar), 137.0 (Ar), 129.0 (Ar), 127.7 (Ar), 82.3 (c), 68.3 (CH$_2$O), 29.8 (OtBu), 21.1 (CH$_3$).

$^{31}$P NMR (81.3 MHz, CDCl$_3$): δ=−9.4 ppm.

Preparation of p-methyl benzyl phosphate: A solution of HCl (4M in dioxane, 2 ml, 8 mmol, 2.6 equivalents) and dioxane (6 ml) was added to the obtained di-tert-butyl, p-methyl benzyl phosphate at 20° C. and the reaction was monitored by TLC. Once the hydrolysis was completed, the dioxane was evaporated under reduced pressure, and the residue was dissolved in water (15 ml) and washed with ether (2×15 ml) to remove excess of the benzyl alcohol starting material. The solvent was then evaporated under reduced pressure and the resultant clear oil slowly changed into a colorless solid upon a prolonged high vacuum drying, to give 0.18 gram (30%) of the final product.

$^1$H NMR (200 MHz, D$_2$O): δ=7.27 (d, J=8.1 Hz, 2H, Ar), 7.19 (d, J=8.1 Hz, 2H, Ar), 4.82 (d, J=7.0 Hz, 2H, CH$_2$O), 2.26 (s, 3H, CH$_3$).

$^{13}$C NMR (50.4 MHz, D$_2$O): δ=138.7 (Ar), 134.0 (Ar), 129.2 (Ar), 128.0 (Ar), 68.0 (CH$_2$O), 20.1 (CH$_3$).

$^{31}$P NMR (81.3 MHz, D$_2$O): δ=0.6 ppm.

B. Synthesis of benzyl phosphate (GSC-1)

The general pathway of the synthesis of GSC-1 is depicted in Scheme 2 below.

The general synthesis of benzyl phosphate is depicted in Scheme 2 hereinbelow:

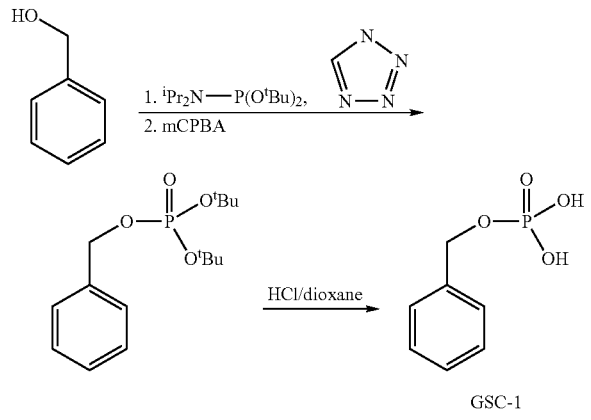

Preparation of di-tert-butyl, benzyl phosphate: 1H-Tetrazole solution (0.45 M in acetonitrile 20 ml, 9 mmol, 3 equivalents) was added in one portion to a stirred solution of the benzyl alcohol (0.34 ml, 3.3 mmol, 1.1 equivalent) and di-tert-butyl diisopropyl phosphoramidite (0.95 ml, 0.83 gram, 3 mmol, 1 equivalent) in dry THF (3 ml). The mixture was stirred for 15 minutes at 20° C. and was thereafter cooled to −40° C. (by means of dry ice/acetonitrile). A solution of 85% mCPBA (0.81 gram in 1 ml dichloromethane, 4 mmol, 1.3 equivalents) in dichloromethane (DCM) (4 ml) was rapidly added while the reaction temperature was kept below 0° C. The solution was allowed to warm up to room temperature and after stirring for 5 minutes at 20° C., 10% aqueous NaHSO$_3$ (10 ml) was added and the mixture stirred for additional 10 minutes. The mixture was then extracted with ether (70 ml) and the aqueous phase discarded. The ethereal phase was washed with 10% aqueous NaHSO$_3$ (2×20 ml), 5% saturated aqueous NaHCO$_3$ (2×20 ml), dried over sodium sulfate and filtered. The organic layer was evaporated and the residue was purified by chromatography on a silica gel column using a mixture of EtOAc/hexanes 1:15 as eluent, to give a mixture of the product (di-tert-butyl, benzyl phosphate) and the starting material, which was used without further purification.

$^1$H NMR (200 MHz, CDCl$_3$): δ=7.36 (m, 5H, Ar), 4.99 (d, J=7.33 Hz, 2H, CH$_2$O), 1.46 (s, 18H, OtBu).

$^{31}$P NMR (81.3 MHz, CDCl$_3$): δ=−9.3 ppm.

Preparation of benzyl phosphate: A solution of HCl (4M in dioxane, 2 ml, 8 mmol, 2.6 equivalents) and dioxane (6 ml) was added to obtained di-tert-butyl, benzyl phosphate at 20° C. and the reaction was monitored by TLC. Once the hydrolysis was completed, the dioxane was evaporated under reduced pressure, and the residue was dissolved in water (15 ml) and washed with ether (2×15 ml) to remove excess of the benzyl alcohol starting material. The solvent was then evaporated under reduced pressure and the resultant clear oil slowly changed into a colorless solid upon a prolonged high vacuum drying, to give 0.17 gram (30%) of the final product.

$^1$H NMR (200 MHz, D$_2$O): δ=7.34 (m, 5H, Ar), 4.82 (d, J=7.09 Hz, 2H, CH$_2$O).

$^{31}$P NMR (81.3 MHz, D$_2$O): δ=0.7 ppm.

C. Synthesis of 3-pyridylmethyl phosphate (GSC-3)

The general pathway for the synthesis of 3-pyridylmethyl phosphate is depicted in Scheme 3 below:

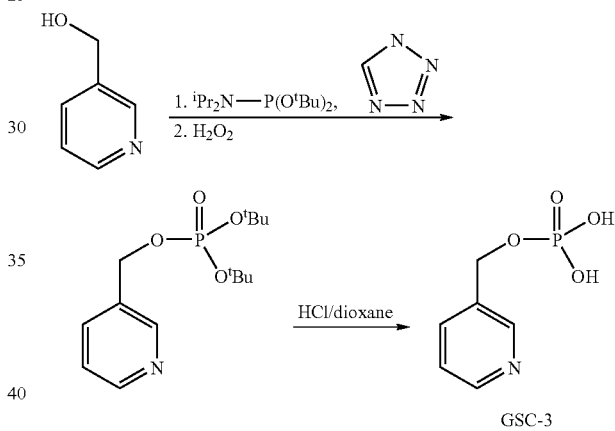

Preparation of di-tert-butyl, 3-Pyridylmethyl phosphate: 1H-Tetrazole solution (0.45 M in acetonitrile, 20 ml, 9 mmol, 3 equivalents) was added in one portion to a stirred solution of 3-pyridylmethanol (0.31 ml, 3.3 mmol, 1.1 equivalent) and di-tert-butyl diisopropyl phosphoramidite (0.95 ml, 0.83 gram, 3 mmol, 1 equivalent) in dry THF (3 ml). The mixture was stirred for 15 minutes at 20° C. and was thereafter cooled to −40° C. (by means of dry ice/acetonitrile). A solution of 85% mCPBA (0.81 gram in 1 ml DCM, 4 mmol, 1.3 equivalents) in DCM (4 ml) was then rapidly added while the reaction temperature was kept below 0° C. The solution was allowed to warm up to room temperature and after stirring for 5 minutes at 20° C., 10% aqueous NaHSO$_3$ (10 ml) was added and the mixture was stirred for additional 10 minutes. The mixture was then extracted with ether (70 ml) and the aqueous phase discarded. The ethereal phase was washed with 10% aqueous NaHSO$_3$ (2×20 ml), 5% saturated aqueous NaHCO$_3$ (2×20 ml), dried over sodium sulfate and filtered. The organic filtrate was evaporated and the residue was purified by chromatography on a silica gel column using a mixture of CHCl$_3$/hexanes 1:1 as eluent, to give a mixture of di-tert-butyl, 3-Pyridylmethyl phosphate and the starting material, which was used without further purification.

$^1$H NMR (200 MHz, CDCl$_3$): δ=8.52 (d, J=1.56 Hz, 1H, Ar), 8.51 (dd, J=4.83 Hz, J=1.53 Hz, 1H, Ar), 7.80 (m, 1H, Ar), 7.33 (dd, J=7.44 Hz, J=4.62 Hz, 1H, Ar), 4.94 (d, J=6.83 Hz, 2H, CH$_2$O), 1.46 (s, 18H, OtBu).
$^{31}$P NMR (81.3 MHz, CDCl$_3$): δ=−9.4 ppm.

Preparation of 3-pyridylmethyl phosphate: A solution of HCl (4M in dioxane, 2 ml, 8 mmol, 2.6 equivalents) and dioxane (6 ml) was added to the obtained di-tert-butyl, 3-Pyridylmethyl phosphate at 20° C. and the reaction was monitored by TLC. Once the hydrolysis was completed, the dioxane was evaporated under reduced pressure, and the residue was dissolved in water (15 ml) and washed with ether (2×15 ml). The solvent was then evaporated under reduced pressure to give 0.19 gram (30%) of the final product.
$^1$H NMR (400 MHz, D$_2$O): δ=8.72 (t, J=0.81 Hz, 1H, Ar), 8.62 (d, J=5.71 Hz, 1H, Ar), 8.51 (d, J=8.27 Hz, 1H, Ar), 7.96 (dd, J=8.15 Hz, J=5.94 Hz, Ar), 5.04 (d, J=8.23 Hz, 2H, CH$_2$O).
$^{31}$P NMR (162 MHz, D$_2$O): δ=0.76 ppm.

D. Synthesis of 3,5-bis(2-aminoethyl)benzyl phosphate (GSC-21)

A general strategy for synthesizing GSC-21, depicted in Scheme 4 below, as well as a purification protocol of the final product, were designed and practiced. 3,5-Bis(2-aminoethyl) benzyl phosphate (GSC-21) was obtained in 5% overall yield by an eight-step synthesis. The corresponding trifluoroacetic acid salt was also prepared.

Scheme 4

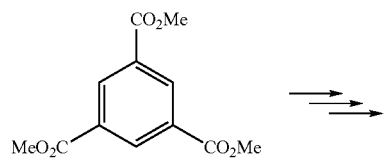

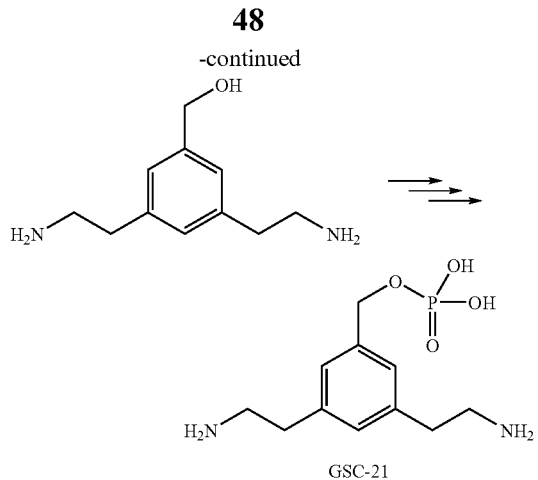

The benzyl alcohol intermediate (see, Scheme 4) was identified as a key intermediate obtainable in four steps from the inexpensive starting material trimethyl 1,3,5-benzenetricarboxylate, as is detailed hereinbelow and is depicted in Scheme 5.

Scheme 5

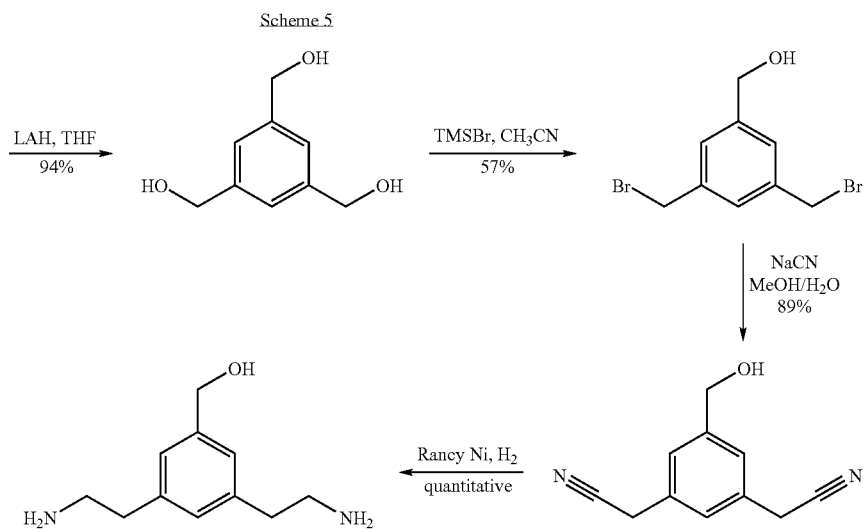

The phosphate moiety was then introduced by reaction of the alcohol with di-tert-butyl diisopropyl phosphoramidite, in the presence of tetrazole, according to the method of Johns (*Tetrahedron Lett.* 1988, 29, 2369-2372). Immediate oxidation without isolation of the resulting phosphite by m-chloroperbenzoic acid (mCPBA) yielded the corresponding phosphate ester. Global deprotection of the amines and the phosphate was achieved by the use of trifluoroacetic acid under controlled conditions. The material was then obtained as its trifluoroacetate salt. The latter was recrystallized prior to treatment with an ion-exchange resin to afford the desired product with adequate purity typically approximately 90% (AUC by HPLC), as depicted in Scheme 6 below.

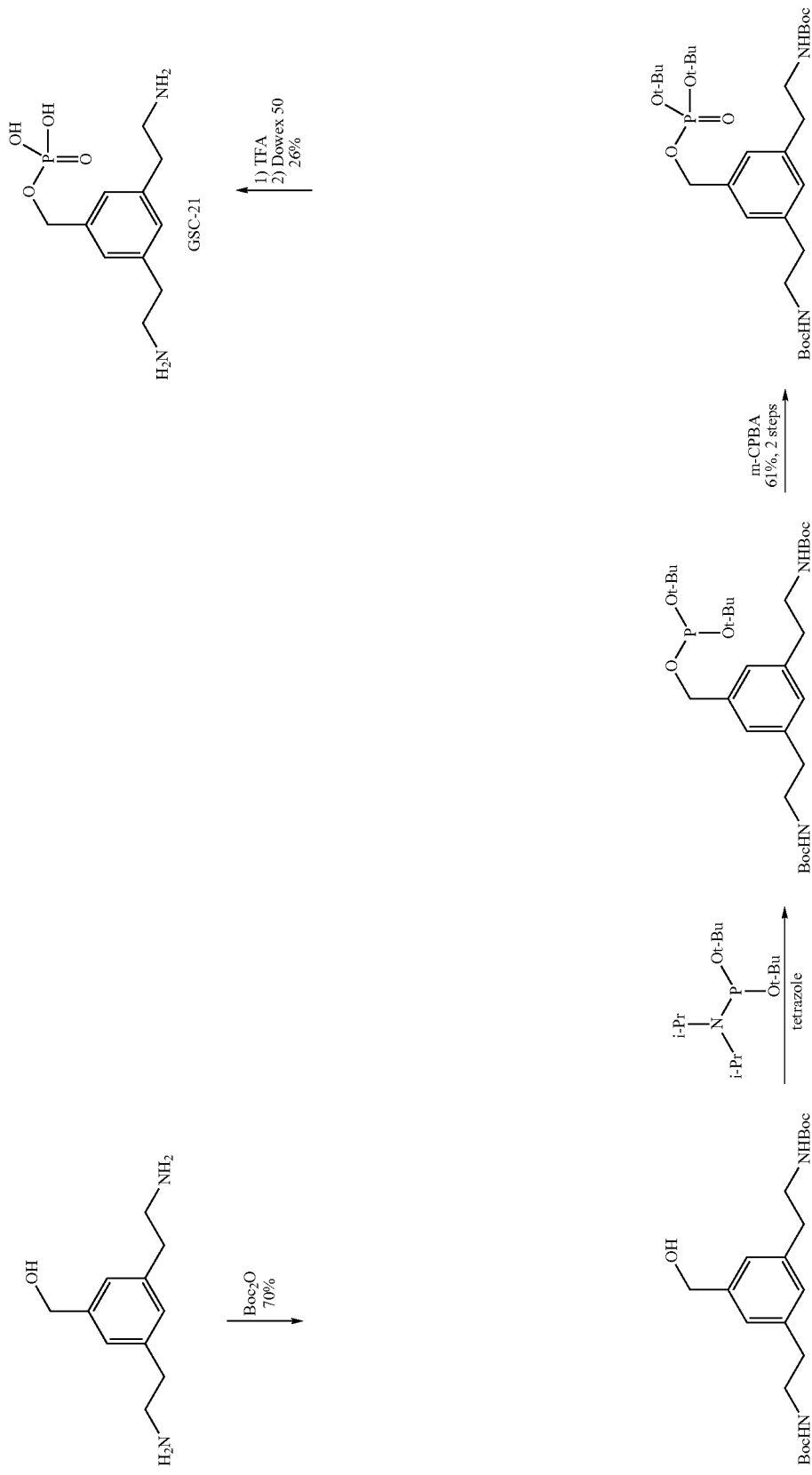
Scheme 6

Following is a detailed description of the synthesis:

Preparation of 1,3,5-Tris(hydroxylmethyl)benzene: A 3-liter, round-bottom flask equipped with an overhead stirrer, an addition funnel and a reflux condenser was charged with lithium aluminum hydride (49.7 grams, 1.31 mol) and anhydrous THF (500 ml) under nitrogen atmosphere. The resulting suspension was slowly heated to reflux and a solution of trimethyl-1,3,5-benzenetricarboxylate (100.0 grams, 0.40 mol) in anhydrous THF (1.0 liter) was added dropwise thereto while maintaining a gentle reflux (3 hours). The resulting gray suspension was stirred under reflux for additional 7 hours and then cooled in an external ice-water bath. The excess lithium aluminum hydride was hydrolyzed by dropwise addition of water (50 ml, 45 minutes), then 15% NaOH (50 ml, slow stream), and finally more water (150 ml, slow stream). The resulting suspension was stirred at ambient temperature for 14 hours. The solids were filtered off and the filtrate was concentrated under high vacuum to obtain a colorless oil which slowly solidified to afford 1,3,5-tris(hydroxylmethyl)benzene (62.3 grams, 94%) as a white solid. The $^1$H NMR and $^{13}$C NMR spectra were consistent with the assigned structure.

$^1$H NMR (500 MHz, d$^6$-DMSO): δ=4.48 (d, J=5.5 Hz, 6H), 5.14 (t, J=6 Hz, 3H), 7.14 (s, 3H).

$^{13}$C NMR (500 MHz, d$^6$-DMSO): δ=62.97 (CH$_2$O), 122.92 (Ar), 141.96 (Ar).

Preparation of 3,5-Bis(bromomethyl)benzyl Alcohol: A 2-liter, round-bottom flask equipped with a magnetic stir bar and an addition funnel was charged with 1,3,5-tris(hydroxylmethyl)benzene [33.7 grams, 0.20 mol) and anhydrous acetonitrile (750 ml). To the resulting suspension was added, with stirring, bromotrimethylsilane (TMSBr) 979.0 ml, 0.60 mol) as a slow stream. The white slurry turned brown and viscous. The reaction mixture was then heated to 40° C. for 25 minutes and resulted in a clear solution. The reaction was judged to be complete by TLC analysis (90:10 methylene chloride/methanol, visualization by UV, starting material R$_f$ 0.07, product R$_f$ 0.77). The solvent was removed under reduced pressure to obtain a brown paste. The crude material was purified by column chromatography (silica gel, 0-5% MeOH/CH$_2$Cl$_2$). 3,5-Bis(bromomethyl)benzyl alcohol (33.5 grams, 57%) was obtained as a white solid. The $^1$H NMR and $^{13}$C NMR spectra, were consistent with the assigned structure.

$^1$H NMR (500 MHz, d$^6$-DMSO): δ=4.49 (s, 2H, CH$_2$O), 4.69 (s, 4H, CH$_2$Br), 7.34 (s, 2H, Ar), 7.38 (s, 1H, Ar).

$^{13}$C NMR (500 MHz, d$^6$-DMSO): δ=62.19 (CH$_2$O), 127.06 (CH$_2$Br), 128.18 (CH$_2$Br), 138.14 (Ar), 143.63 (Ar).

Preparation of 3,5-Bis(cyanomethyl)benzyl Alcohol: A 1-liter, round-bottom flask equipped with an overhead stirrer, an addition funnel and a reflux condenser was charged with 3,5-Bis(bromomethyl)benzyl alcohol (33.1 grams, 0.11 mol) and methanol (400 ml). The resulting clear solution was heated to reflux. A solution of sodium cyanide (16.2 grams, 0.33 mol) in water (25 ml) was added slowly. Heating was continued under reflux for 6 hours before the reaction was judged to be complete by TLC analysis (95:5 methylene chloride/methanol, visualization by UV, starting material R$_f$ 0.62, product R$_f$ 0.38). The reaction mixture was cooled to ambient temperature and solvent was removed under reduced pressure to obtain a brown paste. The latter was triturated with MTBE (6×100 ml). The MTBE extracts were combined and the solvent removed under reduced pressure. The yellow oil thus obtained was then purified by column chromatography (silica gel, 0-5% MeOH/CH$_2$Cl$_2$). 3,5-Bis(cyanomethyl)benzyl alcohol (18.7 grams, 89%) was obtained as a light brown oil, which slowly turned into a waxy white solid. A 1-gram sample was removed and purified via column chromatography to give a purified sample. The $^1$H NMR and $^{13}$C NMR spectra were consistent with the assigned structure.

$^1$H NMR (500 MHz, d$^6$-DMSO): δ=4.06 (s, 4H, CH$_2$CN), 4.52 (s, 2H, CH$_2$O), 7.20 (s, 1H, Ar), 7.27 (s, 2H, Ar).

$^{13}$C NMR (500 MHz, d$^6$-DMSO): δ=62.20 (CH$_2$O), 127.06 (CH$_2$CN), 125.14 (CH$_2$CN) 125.86 (CH$_2$CN), 131.79 (Ar), 144.24 (Ar).

Preparation of 3,5-Bis(aminoethyl)benzyl Alcohol: A sample of 3,5-Bis(cyanomethyl)benzyl alcohol (8.0 grams, 0.04 mol) was divided in three parts and each 2.5- to 3.0-grams portion was charged into separate 500-ml Parr bottles, followed by ethanol (100 ml), and aqueous NaOH (1.2 grams in 5 ml of water). To the resulting solution was added Raney Ni (50% suspension in water, 1.2 grams). The mixture was hydrogenated at 30 psi on a Parr shaker. The reaction was monitored by $^1$H NMR and judged complete after 3 hours. The catalyst was filtered on a pad of diatomaceous earth and the diatomaceous earth pads washed with ethanol (200 ml). The filtrates from all three reactions were combined and solvent removed under reduced pressure to obtain 3,5-bis(aminoethyl)benzyl alcohol as a brown paste of (14.16 grams). $^1$H NMR spectrum of the product showed presence of 25% (w/w) of ethanol. No noticeable change in ethanol content was observed when the sample was dried under high vacuum for an extended period of time. This material was used in the next step of the synthesis without any further purification.

Preparation of 3,5-Bis(tert-butoxycarbonylaminoethyl)benzyl Alcohol: A three-neck, 3-liter, round-bottom flask equipped with a magnetic stir bar, thermometer and gas inlet adapter was charged with 3,5-bis(aminoethyl)-1-hydroxymethylbenzyl alcohol (29.4 grams) dissolved in THF (590 ml) and 2 N aqueous NaOH (590 ml). To the stirred mixture was added di-tert-butyl dicarbonate (59.4 grams, 272 mmol) in one portion. The mixture was heated to 45° C. for 4 hours. The resulting solution was cooled to ambient temperature and the volatile organics were removed by vacuum. To the resulting water mixture was added methanol (600 ml). The stirred solution was heated to 45° C. for 2 days in order to selectively hydrolyze the tert-butoxycarbonate moiety while preserving the carbamates. After cooling to ambient temperature the solution had volatiles removed and the aqueous mixture was extracted with chloroform (3×600 ml). The organic layers were combined, washed with brine (600 ml) and concentrated. After drying under high vacuum, crude 3,5-bis(tert-butoxycarbonylaminoethyl)benzyl alcohol (24.88 grams) was obtained in 67% yield as an off-white solid. The $^1$H NMR spectrum was consistent with the assigned structure. The crude material was used without further purification.

Preparation of protected 3,5-Bis(2-aminoethyl)benzyl Phosphate: A 500-ml, round-bottom flask equipped with a magnetic stir bar and an addition funnel was charged with 3,5-bis(tert-butoxycarbonylaminoethyl)benzyl alcohol (2.3 grams, 0.0058 mol) and anhydrous methylene chloride (45 ml). The resulting solution was cooled to approximately 5° C. in an ice-water bath. A solution of di-tert-butyl diisopropylphosphoramidite (4.5 ml, 0.0144 mol) in anhydrous acetonitrile (45 ml) was added as a slow stream from the addition funnel. A solution of tetrazole (1.0 grams, 0.0144 mol) in a 1:1 mixture of anhydrous acetonitrile/anhydrous methylene chloride (90 ml) was then added slowly (15 minutes). The resulting white suspension was stirred at approximately 5° C. for 1 hour and the reaction was judged complete by TLC analysis (95:5 chloroform/isopropyl alcohol, visualization by staining in ninhydrin, starting material R$_f$ 0.23, product R$_f$ 0.30). The solvent was removed under reduced pressure to obtain a paste, which was dissolved in anhydrous methylene chloride (75 ml) and cooled in a dry ice/acetonitrile bath. A solution of mCPBA (1.3 grams, 0.0144 mol) in anhydrous methylene chloride (50 ml) was added all at once. The resulting mixture was stirred for 1 hour, allowed to warm up to ambient temperature (1 hour) and stirred for another 30 minutes. The reaction mixture then was washed successively with 1.0 M aqueous solution of sodium thiosulfate (100 ml) and saturated sodium bicarbonate (2×100 ml). The organic extract was dried over anhydrous sodium sulfate and filtered. The solvent was removed under reduced pressure to obtain the crude phosphate as a yellow oil, which was then purified by column chromatography (silica gel, 0-5% MeOH/$CH_2Cl_2$). The protected 3,5-Bis(2-aminoethyl)benzyl phosphate (2.1 grams, 61%) was obtained as a viscous, colorless oil. The $^1$H NMR, $^{13}$C NMR and $^{31}$P NMR spectra of the product were consistent with the assigned structure.

$^1$H NMR (500 MHz, $CDCl_3$): δ=1.43 (s, 18H, NH-t-Boc), 1.48 (s, 18H, OP(=O)O-t-Boc), 2.77 (t, 4H, Ar—$CH_2CH_2$), 3.36 (m, 4H, $CH_2$NH), 4.59 (s, 2H, $CH_2$O), 4.95 (d, 2H, NH), 7.20 (s, 1H, Ar), 7.04 (d, 1H, Ar), 7.27 (s, 2H, Ar).

$^{31}$P NMR (500 MHz, $CDCl_3$): δ=−9.69 ppm.

Preparation of 3,5-Bis(2-aminoethyl)benzyl Phosphate TFA Salt: A 250-ml, round-bottom flask was equipped with a magnetic stir bar was charged with the protected phosphate (2.9 grams, 0.0049 mol), anhydrous dichloromethane (30 ml) and trifluoroacetic acid (30 ml). The resulting clear solution was stirred at ambient temperature for 3 hours. The reaction was judged complete by $^1$H NMR and $^{31}$P NMR analysis. Removal of the solvent under reduced pressure afforded a viscous orange oil, which was dissolved in methanol (7.5 ml) and added with stirring to diethyl ether (500 ml), resulting in precipitation of the product. The resulting slurry was stirred for 1 hour at ambient temperature and then solids allowed to settle. The clear solution was decanted off from the top and the product triturated with ether (2×100 ml). Each time the solids were allowed to settle and the clear solution was decanted off. The product was finally dried in a vacuum oven for 108 hours at 55° C. and then for an additional 192 hours at 65° C. to afford 3,5-bis(2-aminoethyl)benzyl phosphate TFA salt (1.78 grams, 71%) as a white solid. The $^1$H NMR, $^{13}$C NMR and $^{31}$P NMR spectra were consistent with the assigned structure. The $^1$H NMR spectrum showed the presence of 8.5% (w/w) of ether in the product. This ether proved very difficult to remove and the material was characterized as hygroscopic.

$^{31}$P NMR (500 MHz, $CDCl_3$): δ=1.14 ppm.

MS: m/z (%)=275.22 (100, $[C_{11}H_{19}N_2O_4P+H]^+$), 549.43 (80), 276.23 (60), 408.24 (40).

Preparation of 3,5-Bis(2-aminoethyl)benzyl Phosphate (GSC-21): A three-neck, 5-liter, round-bottom flask equipped with an overhead mechanical stirrer, thermometer, 1-liter pressure-equalizing addition funnel and gas inlet adapter was charged with a solution of 3,5-bis(tert-butoxycarbonylaminoethyl)benzyl alcohol (24.88 grams, 63.15 mmol) in anhydrous dichloromethane (1) under nitrogen atmosphere. The reaction mixture was cooled with an ice/brine bath. Di-tert-butyl diisopropylphosphoramidite (49.8 ml, 157.9 mmol) in anhydrous acetonitrile (1 liter) was added via the pressure-equalizing addition funnel at such a rate that the reaction temperature was maintained <6° C. Tetrazole (351 ml of a 0.45 M solution in acetonitrile, 157.9 mmol) was diluted with anhydrous acetonitrile (150 ml) and anhydrous dichloromethane (500 ml) and added via the pressure-equalizing addition funnel at such a rate that the temperature was maintained below 6° C. After the addition was completed, the flask was left in the cold bath and the reaction mixture stirred for 1 hour. The flask was then cooled to −35° C. by means of dry ice/acetonitrile bath. A solution of 3-chloroperoxy-benzoic acid (18.4 grams, 82.1 mmol) in anhydrous dichloromethane (500 ml) was added in one portion. The mixture was allowed to warm to ambient temperature and thereafter stirred for 2 hours. The solution was poured into a solution of $Na_2S_2O_3$ (20 grams) and $K_2CO_3$ (50 grams) in water (1.5 liters). The resulting biphasic mixture had a pH of 11. After stirring for 15 minutes the volatile organics were removed in vacuum and the water layer was extracted with chloroform (4×750 ml). The combined organic layers were dried over magnesium sulfate, filtered and concentrated to a yellow oil (69 grams). The crude material was purified by column chromatography (silica gel, MTBE/heptane, 6:4). Mixed fractions containing the product were combined and concentrated to a light yellow oil (32.6 grams). A 28.6-grams portion of the oil was dissolved into dichloromethane (287 ml, 10 volumes). and charged into a 1-liter, round-bottom flask equipped with a 500-ml pressure-equalizing addition funnel and magnetic stir bar. Trifluoroacetic acid (287 ml, 10 volumes) was added rapidly via the pressure-equalizing addition funnel. The resulting solution was stirred for 5 hours. After concentrating and drying overnight under high vacuum, a thick orange oil (37.88 grams) was obtained. The residue was dissolved in water (57 ml, 1.5 volumes) and added dropwise into stirred methanol (90 volumes) yielding a precipitate. After stirring for 30 minutes, the solids were allowed to settle for 1 hour and the liquid was decanted off. The remaining liquid was removed in vacuum giving 13.72 grams of solid. The material was dissolved in water (68 ml, 5 volumes) and loaded onto Dowex 50WX8-200 ion-exchange resin (137 grams). The column was washed with water (550 ml, 40 volumes). The product was eluted with 3:1 MeOH/aqueous $NH_4OH$ (2 liters, 145 volumes). The methanol fractions were concentrated under reduced pressure to yield an off-white solid. The solid was dissolved in a minimum amount of water and added into stirred methanol (40 volumes). The precipitate was collected via filtration and dried overnight under vacuum. The resulting powder was triturated with water (7 volumes). After filtration and drying under high vacuum, the final product (2.0 grams) was obtained as a white powder. The filtrate was concentrated and the residue triturated with water (5 volumes). After filtration and drying under high vacuum, a second crop of product [0.9 grams) was obtained. The two lots were combined and blended for 10 minutes. 3,5-Bis(2-aminoethyl)benzyl phosphate (GSC-21) was obtained as a white powder. The $^1$H NMR, $^{31}$P NMR, and $^{13}$C NMR spectra of the product were consistent with the assigned structure.

$^1$H NMR (500 MHz, $D_2O$): δ=2.93 (t, J=7 Hz, Ar—$CH_2CH_2$), 3.28 (m, $CH_2$NH), 4.66 (s, $CH_2$O), 4.75 (t, J=8.5 Hz, NH), 7.09 (s, 1H, Ar), 7.24 (s, 2H, Ar).

$^{13}$C NMR (500 MHz, $D_2O$): δ=32.56, 40.43, 65.6, 126.74, 128.47, 137.48, 140.54.

$^{31}$P-NMR (500 MHz, $D_2O$): δ=3.97 ppm.

Figure 4A:
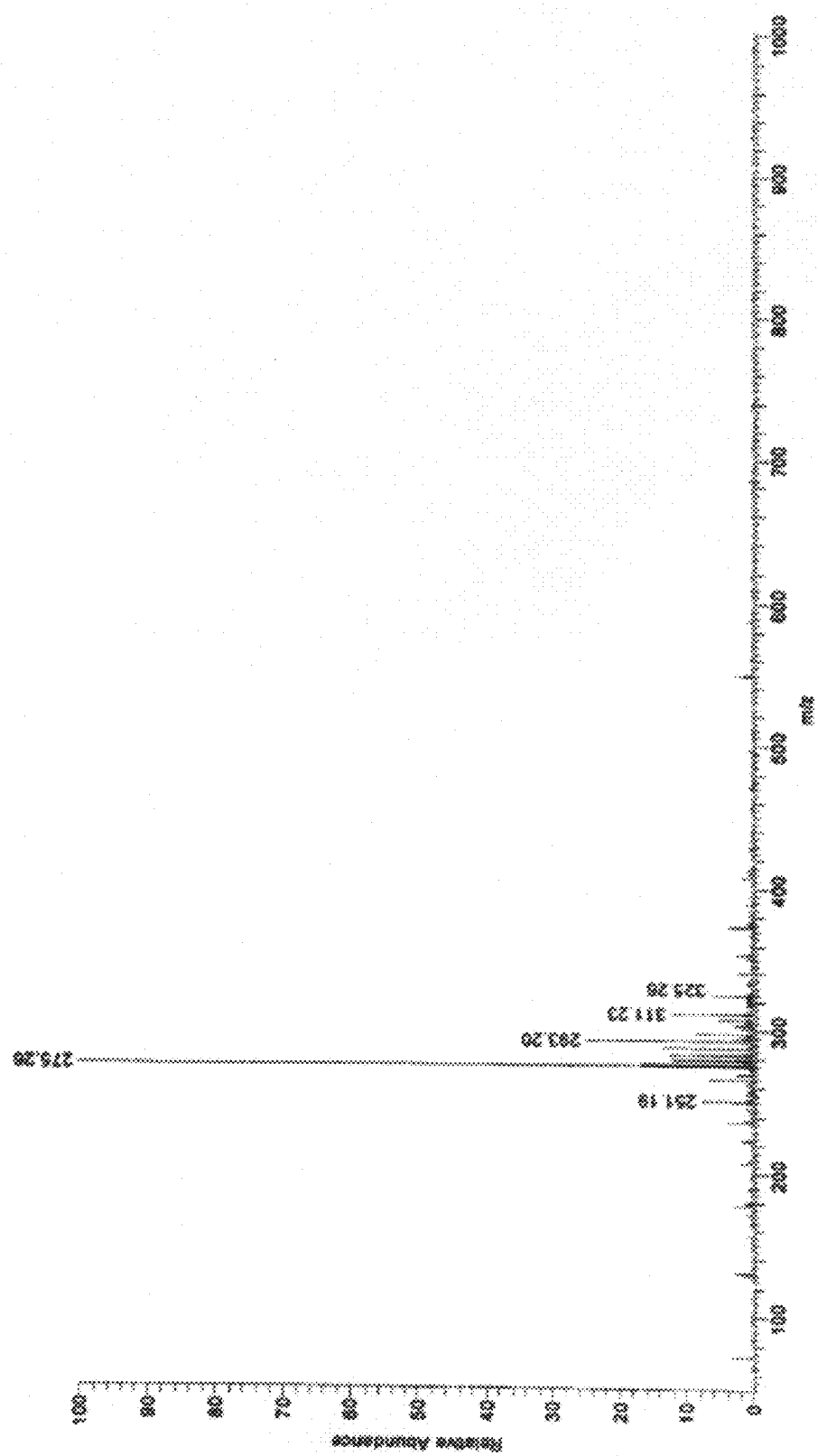

The mass spectrum of the final product, presented in FIG. 4a, indicated a molecular peak at m/z of 275 $[C_{11}H_{19}N_2O_4P+H]^+$. The HPLC chromatogram (obtained using method A described above), presented in FIG. 4b, showed a 96.7% purity of the product. The final product was characterized as non-hygroscopic.

Using the same strategy, the novel compounds GSC-4 and GSC-5 were synthesized as follows:

E. Synthesis of 3-(guanidinomethy)benzyl phosphate (GSC-5)

The general synthesis of GSC-5, as its trifluoroacetic acid salt, is depicted in Scheme 7 below:

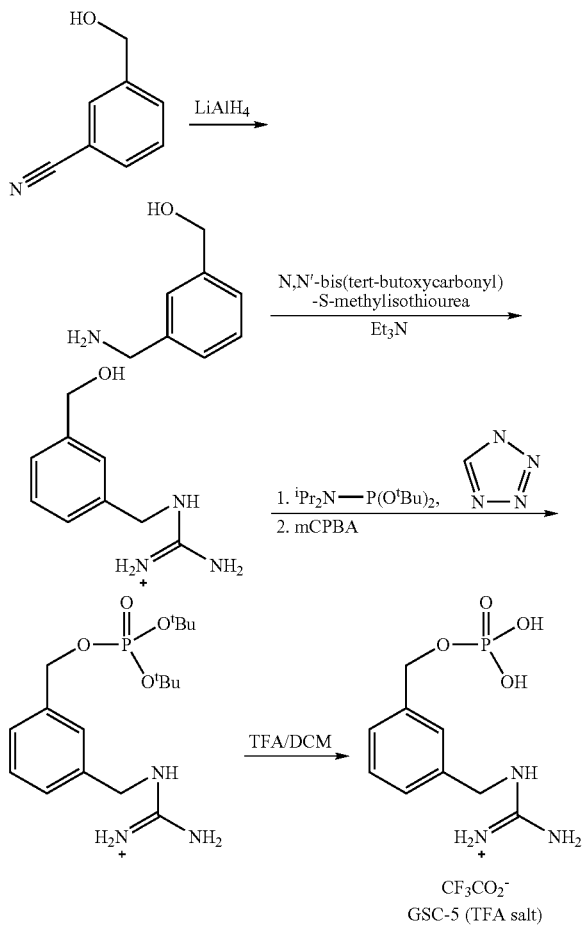

Scheme 7

Preparation of 3-(aminomethyl)benzyl alcohol: A solution of 3-(hydroxymethyl)benzonitrile in THF was slowly added to a refluxing solution of LiAlH$_4$ in THF with vigorous stirring, maintained under nitrogen atmosphere. The solution was heated at reflux overnight and water was thereafter slowly added dropwise to quench the reaction (until no further evolution of H$_2$ was apparent). The THF was evaporated under reduced pressure and ether/acidified water was added. The ether phase was discarded. The aqueous phase was washed with ether and the organic phase was discarded. NaOH was added until the pH of the aqueous phase reached pH 7. The solution was extracted with THF three times, dried over MgSO$_4$ and evaporated under reduced pressure to furnish a slightly yellow residue which was purified by chromatography on a silica gel column using a gradient eluent starting from ethyl acetate and ending with a mixture of 1:1 ethyl acetate:MeOH), to give the intermediate in a 40% yield.

$^1$H NMR (200 MHz, d$^6$-DMSO): δ=7.16-7.27 (m, 4H, Ar), 4.47 (s, 2H, CH$_2$O), 3.94 (bs, 2H, NH$_2$), 3.72 (s, 2H, CH$_2$NH$_2$).

$^{13}$C NMR (50.4 MHz, CDCl$_3$) δ=143.1, 142.8, 128.2, 125.9, 125.7, 124.9, 63.3, 45.6.

Preparation of 3-(N,N'-bis-BOC-guanidinomethyl)benzyl alcohol: A solution of 3-(aminomethyl)benzylalcohol, 3-(N, N'-bis(tert-butoxycarbonyl)-S-methylisothiourea and triethyl amine in dry DMF was stirred at room temperature overnight. An ether/water mixture was then added and the organic layer separated, while the aqueous layer was extracted with ether. The combined organic extract was washed with water, dried over MgSO$_4$ and evaporated under reduced pressure. The crude product was purified by flash chromatography using a gradient eluent starting from hexanes and ending with a mixture of 1:5 ethyl acetate:hexanes), in 85% yield.

$^1$H NMR (200 MHz, CDCl$_3$): δ=11.51 (bs, 1H), 8.56 (bs, 1H), 7.22-7.38 (m, 4H), 4.70 (s, 2H), 4.65 (d, J=5.1 Hz, 2H), 1.52 (s, 9H), 1.48 (s, 9H).

$^{13}$C NMR (50 MHz, CDCl$_3$): δ=155.9, 153.1, 141.5, 137.7, 128.9, 127.0, 126.4, 126.2, 65.0, 45.0, 28.2, 27.9.

Preparation of Di-tert-butyl, 3-(N,N'-bis-BOC-guanidinomethy) benzyl phosphate: 1H-Tetrazole solution (0.45 M in acetonitrile, 20 ml, 9 mmol, 3 equivalents) was added in one portion to a stirred solution of 3-(N,N'-bis-BOC-guanidinomethyl)benzyl alcohol (1 equivalent) and di-tert-butyl diisopropyl phosphoramidite (1.42 ml, 1.24 grams, 4.5 mmol, 1.5 equivalents) in dry THF (3 ml). The mixture was stirred for 30 minutes at 20° C. and was then cooled to −40° C. (by means of dry ice/acetonitrile). A solution of 85% mCPBA (1.25 grams in 1.5 ml DCM, 6.15 mmol, 2.0 equivalents) in DCM (4 ml) was rapidly added while keeping the reaction temperature below 0° C. The solution was allowed to warm up to room temperature and, after stirring for 20 minutes, 10% aqueous NaHSO$_3$ (10 ml) was added and the mixture was stirred for additional 5 minutes. The mixture was extracted with ether (70 ml) and the aqueous phase discarded. The ethereal phase was washed with 10% aqueous NaHSO$_3$ (2×20 ml) and saturated aqueous NaHCO$_3$ (2×20 ml), dried over sodium sulfate and filtered. The organic filtrate was evaporated and the residue was purified by chromatography on a silica gel column using a gradient eluent of ethyl acetate/hexanes 1:9 to 1:5), to give a mixture of the phosphate ester product and the benzyl alcohol starting material, which was further purified by chromatography on a silica gel column, using a gradient eluent of CHCl$_3$:MeOH 30:1 to 20:1), to give pure di-tert-butyl, 3-(N,N'-bis-BOC-guanidinomethy) benzyl phosphate in 70% yield.

$^1$H NMR (200 MHz, CDCl$_3$): δ=11.52 (bs, 1H), 8.53 (bs, 1H), 7.25-7.35 (m, 4H), 4.99 (d, J=7.2 Hz, 2H), 4.63 (d, J=5.1 Hz, 2H), 1.51 (s, 9H), 1.47 (s, 27).

$^{31}$P NMR (162 MHz, CDCl$_3$): δ=−9.3.

Preparation of 3-(guanidinomethy) benzyl phosphate, trifluoroacetic acid salt: A solution of 25% trifluoroacetic acid (TFA) in DCM was added to di-tert-butyl, 3-(N,N'-bis-BOC-guanidinomethy) benzyl phosphate at 20° C. and the reaction mixture was stirred for 18 hours. The solvent and TFA were thereafter evaporated under reduced pressure, and the residue was dissolved in water and washed with ether. The solvent was then evaporated under reduced pressure, to give the pure product in 60% yield.

$^1$H NMR (200 MHz, D$_2$O): δ=7.25-7.35 (m, 4H), 4.84 (d, J=7.2 Hz, 2H), 4.37 (s, 1H).

$^{31}$P NMR (162 MHz, CDCl$_3$): δ=0.85.

$^{19}$F NMR: δ=−76.6.

The trifluoroacetic acid can be removed or replace by, for example, HCl, using procedures well known in the art, to give the free guanidine or, for example, a hydrochloride salt of the compound.

F. Synthesis of 3-guanidinobenzyl phosphate (GSC-4)

The general synthesis of GSC-4, as its trifluoroacetic acid salt, is depicted in Scheme 8 below:

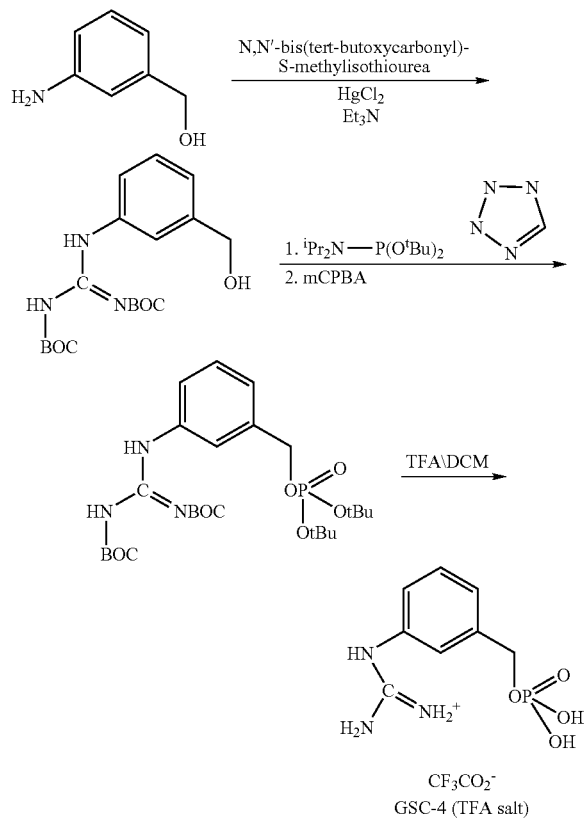

Scheme 8

GSC-4 (TFA salt)

Preparation of 3-(N,N'-bis-BOC-guanidino)benzyl alcohol: A solution of N,N'-bis(tert-butoxycarbonyl)-S-methylisothiourea (1.32 gram, 4.4 mmol, 1.1 equivalents), mercury chloride (1.22 gram, 4.4 mmol, 1.1 equivalents) and triethylamine (1.72 ml, 12 mmol, 3 equivalents) was added to 3-aminobenzyl alcohol (0.5 gram, 4 mmol, 1.0 equivalent) in dry dimethylformamide (DMF) and the reaction mixture was stirred at room temperature for 5 hours. The mixture was thereafter extracted with ether/water and the organic layer was washed with saturated aqueous $NH_4Cl$ and brine. The aqueous layer was extracted with ether. The combined ether solution was dried over $MgSO_4$ and evaporated under reduced pressure. The crude product was purified by flash chromatography on silica gel using a gradient eluent of hexanes to 40:60 ethyl acetate:hexanes), to give the intermediate in 60% yield.

$^1$H NMR (200 MHz, $CDCl_3$): δ=11.60 (brs, 1H), 10.30 (brs, 1H), 7.11-7.55 (m, 4H), 4.65 (s, 2H), 1.49 (s, 9H), 1.48 (s, 9H).

$^{13}$C NMR (400 MHz, $CDCl_3$): δ=171.4, 163.4, 153.7, 142.0, 136.7, 129.0, 123.4, 121.4, 120.8, 65.8, 64.7, 28.1, 27.9.

Preparation of di-tert-butyl, 3-(N,N'-bis-BOC-guanidino) benzyl phosphate: 1-H-tetrazole solution (0.45 M in acetonitrile, 18.4 ml, 8.3 mmol, 3 equivalents) was added in one portion to a stirred solution of 3-(N,N'-bis-BOC guanidino) benzyl alcohol (1 gram, 2.8 mmol, 1 equivalent) and di-tert-butyl diisopropyl phosphoramidite (1.13 ml, 3.6 mmol, 1.3 equivalents) in dry THF (3 ml). The mixture was stirred for 30 minutes at 20° C. and thereafter cooled to −40° C. (by means of dry ice/acetonitrile). A solution of 85% mCPBA (0.85 gram in 1.5 ml DCM, 4.20 mmol, 1.5 equivalents) in DCM (4 ml) was rapidly added while keeping the reaction temperature below 0° C. The reaction was allowed to reach room temperature and after stirring for 20 minutes, 10% aqueous $NaHSO_3$ (10 ml) was added and the mixture stirred for additional 10 minutes. The mixture was extracted with ether (50 ml) and the aqueous phase discarded. The ethereal phase was washed with 10% aqueous $NaHSO_3$ (2×20 ml) and saturated aqueous $NaHCO_3$ (2×20 ml), dried over $MgSO_4$ and filtered. The solvent was evaporated and the residue was purified by chromatography on a silica gel column using a gradient eluent of ethyl acetate/hexanes 10:90 to 30:70), to give the protected product in 60% yield.

$^1$H NMR (200 MHz, $CDCl_3$): δ=11.65 (brs, 1H), 10.40 (brs, 1H), 7.10-7.64 (m, 4H), 4.97 (d, J=7.0 Hz, 2H), 1.49 (s, 18H), 1.45 (s, 18H).

$^{13}$C NMR (400 MHz, $CDCl_3$): δ=153.3, 136.6, 129.2, 124.3, 122.1, 121.3, 67.9, 6 29.8, 28.0.

$^{31}$P NMR (200 MHz, $CDCl_3$): δ=−9.3.

Preparation of 3-guanidinobenzyl phosphate, trifluoroacetic acid salt: A solution of 25% TFA (1.5 ml) in DCM (4.5 ml) was added to di-tert-butyl-3-(N,N'-bis-BOC guanidino)benzyl phosphate (0.3 gram, 0.54 mmol, 1 equivalent) at 20° C. and the reaction mixture was stirred for 18 hours. The solvent and TFA were thereafter evaporated under reduce pressure and the residue was dissolved in water and washed with ether. The solvent was evaporated under reduced pressure (lyophilizer), to give the pure product in 40% yield ($C_{10}H_{13}F_3N_3O_6P$; Mw=359.2 grams/mol).

$^1$H NMR (200 MHz, $CDCl_3$): δ=7.13-7.38 (m, 4H), 4.83 (d, J=7.6 Hz, 2H)

$^{13}$C NMR (400 MHz, $CDCl_3$): δ=156.3, 139.5, 134.3, 130.1, 126.8, 125.3, 124.6, 66.4.

$^{31}$P NMR (200 MHz, $CDCl_3$): δ=0.8.

The trifluoroacetic acid can be removed or replace by, for example, HCl, using procedures well known in the art, to give the free guanidine or, for example, a hydrochloride salt of the compound.

G. Synthesis of 3-(guanidinoethy)benzyl phosphate (GSC-6)

The general synthesis of GSC-6, as its trifluoroacetic acid salt, is depicted in Scheme 9 below:

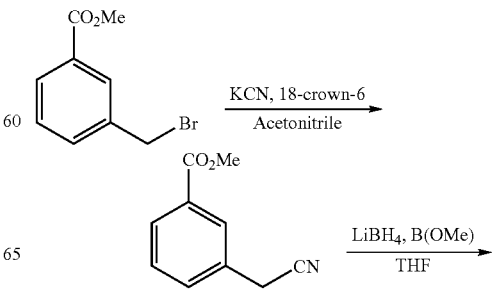

Scheme 9

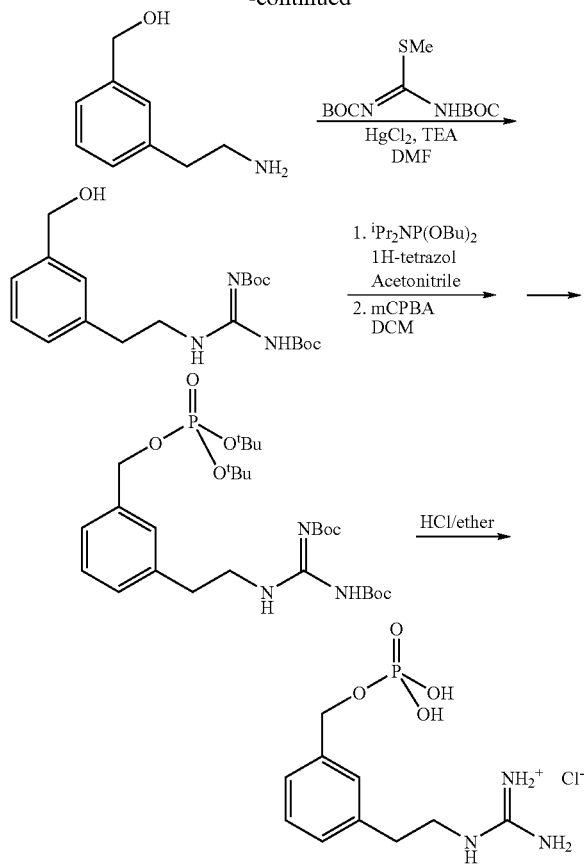

Preparation of Methyl 3-(cyanomethyl)benzoate: A mixture of methyl 3-(bromomethyl)benzoate (0.6 gram, 2.6 mmol), potassium cyanide (0.35 gram, 5.2 mmol) and 60 mg of 18-crown-6 in 6 ml acetonitrile was vigorously stirred at room temperature for 24 hours. The mixture was filtered, the filtrate concentrated to half volume, water was added to the remaining mixture and extraction was performed with dichloromethane. The organic phase was dried over $MgSO_4$ and the solvent was evaporated, to give the product as a yellow liquid, which was used without purification.

TLC (30% EtOAc/Hexanes); $R_f$=0.45.

$^1$H NMR (200 MHz, DMSO-$d_6$): δ=7.96 (m, 1H), 7.93 (m, 1H), 7.62 (m, 1H), 7.55 (m, 1H), 3.88 (s, 3H), 3.82 (s, 2H);

$^{13}$C NMR (50 MHz, DMSO-$d_6$): δ=166.4, 133.5, 132.8, 130.8, 130.1, 129.2, 129.0, 119.6, 52.8, 22.7.

Preparation of 3-(2-Aminoethyl)benzyl alcohol: To a solution of methyl-3-(cyanomethyl)benzoate (4 grams, 0.023 mol, 1 molequivalent) in 5 ml dry THF, 2M $LiBH_4$ in THF (60 ml, 5 molequivalents) and $(MeO)_3B$ (3 ml, 1 molequivalent) were added under nitrogen atmosphere. The reaction mixture was stirred and heated at 70-75° C. for 16-18 hours. After cooling, THF was evaporated, and $2NH_2SO_4$ was added to the residue (to acidify the solution to pH of 1-2). The resulting solution was washed with ether and powdered $K_2CO_3$ was added to the aqueous phase until the pH reached 7. NaCl was then added and the solution was extracted with THF. The organic phase was dried over $MgSO_4$ and the solvent was evaporated, to give a 2.3 grams (67%) of a pure product, which was used without purification.

$^1$H NMR (200 MHz, Methanol-$d_4$): δ=7.46-7.32 (m, 4H), 4.60 (s, 2H), 3.18-3.07 (m, 2H), 2.98-2.90 (m, 2H);

$^{13}$C NMR (50 MHz, Methanol-$d_4$): δ=141.9, 136.8, 128.2, 127.2, 126.8, 125.3, 63.5, 40.7, 33.7.

Preparation of 3-(N,N'-bis-Boc-guanidinomethyl)benzyl alcohol: A mixture of 3-(aminoethyl)benzyl alcohol (2.3 grams, 0.015 mol, 1 molequivalent), N,N'-bis(tert-butoxycarbonyl)-S-methylisothiourea (4.8 grams, 0.016 mol, 1.1 molequivalent), mercury chloride (4.5 grams, 0.016 mol, 1.1 molequivalent), and triethylamine (7 ml, 0.048 mol, 3 molequivalent) in dry DMF (25 ml) was stirred at room temperature overnight under nitrogen atmosphere. Ethyl acetate (100 ml) was then added and the suspension was filtered over Celite. The filtrate was washed with water, saturated aqueous $NH_4Cl$, and brine, dried over $MgSO_4$ and the solvent was evaporated under reduced pressure. The crude product was purified by flash chromatography (using a gradient eluent of a 10:90 to 30:70 mixture of EtOAc:hexanes), to give 1.9 grams (32%) of the pure product.

$^1$H NMR (200 MHz, $CDCl_3$): δ=11.4 (bs, 1H), 8.28 (bs, 1H), 7.23-7.09 (m, 4H), 4.59 (s, 2H), 3.61 (q, J=6.9 Hz, 2H), 2.80 (t, J=6.9 Hz, 2H), 1.45 (s, 9H), 1.37 (s, 9H).

Preparation of Di-tert-butyl 3-(N,N'-bis-Boc-guanidinoethyl)benzyl phosphate: 1H-Tetrazol solution (0.45 M in acetonitrile, 30 ml, 14 mmol, 3 molequivalent) was added in one portion to a stirred solution of 3-(N,N'-bis-Boc-guanidinoethyl)benzyl alcohol (1.8 gram, 4.6 mmol, 1 molequivalent) and di-tert-butyl diisopropyl phosphoramidite (1.9 gram, 2.2 ml, 7 mmol, 1.5 molequivalent) in 8 ml dry THF under nitrogen atmosphere. The mixture was stirred for 50 minutes at room temperature, then cooled to −40° C. and a solution of 77% m-CPBA (1.8 gram, 9.2 mol, 2 molequivalents) in 10 ml dry dichloromethane was rapidly added while keeping the reaction temperature below 0° C. The solution was allowed to warm up to room temperature and, after stirring for 30 minutes, 20 ml of 10% aqueous $NaHSO_3$ was added and the mixture was stirred for 10-15 minutes. The mixture was thereafter washed with 10% $NaHSO_3$, 5% $NaHCO_3$, and brine and dried over $MgSO_4$. The organic layer was evaporated and the residue was purified by flash chromatography (using a gradient eluent of a 10:90 to 30:70 mixture of EtOAc:hexanes), to give an impure product. Additional purification by chromatography, using isocratic $CHCl_3$, gave the pure product in 35% yield.

$^1$H NMR (200 MHz, $CDCl_3$): δ=11.36 (bs, 1H), 8.29 (bs, 1H), 7.19-7.06 (m, 4H, Ar), 4.89 (d, J=7.1 Hz, 2H), 3.56 (q, J=7.0 Hz, 2H), 2.78 (t, J=7.1 Hz, 2H), 1.40 (s, 9H), 1.32 (s, 27H);

$^{13}$C NMR (100 MHz, $CDCl_3$): δ=163.5, 156.05, 153.1, 138.6, 137.4, 128.6, 128.4, 127.9, 125.8, 82.9, 82.3, 79.2, 68.2, 42.1, 35.1, 29.8, 28.3;

$^{31}$P NMR (81 MHz, $CDCl_3$): δ=−9.2.

Preparation of 3-(guanidinoethyl)benzyl phosphate, hydrochloric salt: Di-tert-butyl 3-(N,N'-bis-Boc-guanidinoethyl)benzyl phosphate (100 mg) was dissolved in a 1M solution of HCl in ether (5 ml), and the solution was stirred at room temperature for 5-6 hours. The ether was then evaporated, water was added to the residue and the resulting solution was washed with ether. The aqueous solution was then lyophilized to give 40 mg (72%) of the product.

$^1$H NMR (400 MHz, $D_2O$): δ=7.12-7.02 (m, 4H), 4.67 (d, J=6.5 Hz, 2H), 3.21 (t, J=6.0 Hz, 2H), 2.66 (t, J=6.0 Hz, 2H);

$^{13}$C NMR (100 MHz, $D_2O$): δ=156.6, 138.7, 137.4, 129.0, 128.6, 128.1, 125.9, 67.3, 42.1, 34.1;

$^{31}$P NMR (00 MHz, $D_2O$): δ=0.7.

H. Synthesis of 3,5-bisguanidino benzyl phosphate (GSC-7)

GSC-7 was prepared as follows:

Preparation of 3,5-Bis(N,N'-bis-Boc-guanidino) benzyl alcohol: To a solution of 3,5-diaminobenzyl alcohol dihydrochloride (2.2 grams, 0.01 mol, 1.0 molequivalent) in dry DMF (30 ml), N,N'-bis(tert-butoxycarbonyl)-S-methylisothiourea (6.6 grams, 0.023 mol, 2.3 molequivalents), mercury chloride (6.2 grams, 0.023 mol, 2.3 molequivalents) and triethyl amine (10 ml, 0.07 mol, 3 molequivalents) were added and the reaction mixture was stirred at room temperature overnight (about 18 hours). Ethyl acetate was thereafter added and the resulting suspension was filtered through Celite. The organic layer was washed with $H_2O$, saturated $NH_4Cl$, and brine, dried over $MgSO_4$ and the solvent was evaporated under reduced pressure. The crude product was purified by flash chromatography on silica gel (using a gradient eluent of a 20% mixture of EtOAc/hexanes to a 30% mixture of EtOAc/hexanes), to give 6.0 grams (96%) of the product.

$^1$H NMR (200 MHz, CDCl$_3$): δ=11.50 (bs, 2H), 10.36 (bs, 2H), 7.70 (t, J=3.0 Hz, 1H), 7.42 (d, J=3.0 Hz, 2H), 4.59 (s, 2H), 1.42 (s, 18H), 1.36 (s, 18H);

$^{13}$C NMR (50 MHz, CDCl$_3$): δ=163.2, 153.4, 153.1, 142.7, 137.3, 116.8, 114.6, 83.6, 79.6, 64.7, 28.1, 28.0.

Preparation of Di-tert-butyl-3,5-Bis(N,N'-bis-Boc-guanidino) benzyl phosphate: A 1-H-tetrazole solution (0.45 M in acetonitrile, 20 ml, 0.009 mol, 3 molequivalents) was added in one portion to a stirred solution of 3,5-Bis(N,N'-bis-Boc-guanidino)benzyl alcohol (2 grams, 0.003 mol, 1 molequivalent) and di-tert-butyl diisopropyl phosphorimidate (1.15 ml, 0.0036 mol, 1.2 molequivalent) in 5 ml dry THF, under nitrogen atmosphere. The resulting mixture was stirred for 50-60 minutes at room temperature, then cooled to −40° C. (by means of dry ice/acetonitrile) and a solution of 77% m-CPBA (0.8 grams, 0.0045 mol, 1.5 molequivalent) in 5 ml dichloromethane was rapidly added while maintaining the reaction temperature below 0° C. The reaction mixture was thereafter allowed to warm to room temperature and was stirred for 30 minutes. 10% aqueous NaHSO$_3$ (10 ml) was then added and the mixture stirred for additional 10-15 minutes. The mixture was extracted with ether (20-80 ml) and the ethereal phase was washed with 10% aqueous NaHCO$_3$, and brine, dried over MgSO$_4$ and filtered. The solvent was evaporated and the residue was chromatographed on a silica gel column (using a gradient eluent of a 10:90 to 30:70 mixture of EtOAc:hexanes) to give to give an impure product. Additional purification by chromatography, using isocratic CHCl$_3$, gave the pure product in 40% yield.

$^1$H NMR (200 MHz, CDCl$_3$): δ=11.5 (bs, 2H), 10.40 (bs, 2H), 7.81 (s, 1H), 7.38 (s, 2H), 4.91 (d, J=7.0 Hz, 2H), 1.41 (s, 18H), 1.40 (s, 18H);

$^{13}$C NMR (50 MHz, CDCl$_3$): δ=163.1, 153.2, 153.1, 138.1 (d, J=8.3 Hz), 137.3, 83.6, 82.2 (d, J=6.8 Hz), 79.4, 67.8 (d, J=4.9 Hz), 29.7, 27.9;

$^{31}$P NMR (81 MHz, CDCl$_3$): δ=−9.4.

Preparation of 3,5-Bisguanidinobenzyl phosphoric acid dihydrochloride: 1 M solution of HCl in ether (35 ml) was added to di-tert-butyl-3,5-Bis(N,N'-bis-Boc-guanidino)benzyl phosphate (0.45 gram, 0.57 mmol) and the resulting mixture was stirred at room temperature for 22-24 hours, during which a white precipitate was formed. The ether was thereafter decanted and the precipitate was washed 3-4 times with dry ether, evaporated and the residue was dried under high vacuum to give 0.13 grams (65%) of the final product.

$^1$H NMR (400 MHz, D$_2$O): δ=7.16 (s, 2H), 7.11 (s, 1H), 4.8 (d, J=8.2 Hz, 2H);

$^{13}$C NMR (100 MHz, D$_2$O): δ=156.10, 141.2, 135.8, 123.3, 121.9, 66.0;

$^{31}$P NMR (162 MHz, D$_2$O): δ=0.7.

Example 3

Activity Assays

Methods:

In vitro inhibition assays: Purified recombinant rabbit GSK-3β (Eldar-Finkelman et al., 1996) was incubated with peptide substrate PGS-1 (YRRAAVPPSPSLSRHSSPSQS(p)EDEEE) (SEQ ID NO:1) or peptide substrate p9CREB (SEQ ID NO:2) and with phenyl phosphate, pyridoxal phosphate (P-5-P), GSC-1, GSC-2, GSC-3, GSC-4, GSC-5, GSC-6, GSC-7 or GSC-21 (structural formulas are depicted in FIG. 3), at indicated concentrations. The reaction mixture included Tris 50 mM (pH=7.3), 10 mM MgAc, $^{32}$P[γ-ATP] (100 μM), 0.01% β-mercaptoethanol, and was incubated for 10 minutes at 30° C. Reactions were spotted on phosphocellulose paper (p81), washed with 100 mM phosphoric acid, and counted for radioactivity (as described in Eldar-Finkelman et al., 1996).

The effect of GSC-4, GSC-5 and GSC-7 (100 and 200 μM) on other protein kinases was tested by incubating CDK-2 (1 unit) with a reaction mixture similar to that described hereinabove and containing histone H1 substrate (5 μg). The reactions were boiled with SDS sample buffer, separated on gel electrophoresis and autoradiographed.

Activation of glycogen synthase by GSK-3 inhibitors: Activation of glycogen synthase can serve as a good marker for inhibition of GSK-3. Our previous data indicated that GSK-3 peptide inhibitors activated glycogen synthase. Thus, activation of glycogen synthase by GSC-5 and GSC-7 was tested in C2C12 myotubes. C2C12 cells were treated with GSC-5 and GSC-7 for 2.5 hours at indicated concentrations and lysate supernatants were thereafter assayed for glycogen synthase activity. The activity of glycogen synthase in cells treated with vehicle DMSO (0.1% DMSO) was normalized to 1 unit and the values for glycogen synthase activity observed in cells treated with GSK-3 inhibitors are presented as fold stimulation over the cells treated with vehicle 0.1% HCL.

Glucose uptake in isolated adipocytes: Mice adipocytes were isolated from epididymal fat pad by digestion with 0.8 mg/ml collagenase (Worthington Biochemical) as described previously (Lawrence et al., 1977). Digested fat pads were passed through nylon mesh and cells were washed 3 times with Krebs-bicarbonate buffer (pH=7.4) containing 1% bovine serum albumin (Fraction V, Boehringer Mannheim, Germany), 10 mM HEPES (pH=7.3), 5 mM glucose and 200 nM adenosine. Cells were incubated with GSC-4 and GSC-21 at indicated concentrations for 2.5 hours, followed by addition of 2-deoxy [$^3$H] glucose (0.5 μci/vial) for 10 minutes. The assay was terminated by centrifugation of cells through dinonylphthalate (ICN, USA). $^3$H was thereafter quantitated by liquid scintillation analyzer (Packard). Nonspecific uptake of 2-deoxy-[$^3$H] glucose was determined by the addition of cytochalasin B (50 μM) 30 minutes prior to the addition of radioactive material.

Results:

In vitro inhibition assays: In a preliminary inhibition assay, the GSK-3 inhibition activity of the known compounds phenyl phosphate, pyridoxal phosphate, GSC-1, GSC-2 and GSC-3 was tested as described hereinabove. The results, presented in FIG. 5 indicate that all the tested compounds exerted an inhibition activity toward GSK-3, with the phosphate derivatives of pyridine, namely, pyridoxal phosphate and GSC-3, being more active than the phosphate derivatives of phenyl (phenyl phosphate, GSC-1 and GSC-2).

In an additional inhibition assay, the GSK-3 inhibition activity of GSC-1, GSC-2, GSC-3, GSC-4, and GSC-21 was tested. The ability of GSK-3 to phosphorylate PGS-1 peptide substrate was measured in the presence of indicated concentrations of these compounds. The results, presented in FIG. 6, represent the percentage of GSK-3 activity as compared with a control incubation without inhibitors and are mean of 2 independent experiments±SEM, where each point was assayed in triplicate.

As is shown in FIG. 6, all the tested compounds were found highly active in inhibiting GSK-3 activity (IC50 values of 1-5 mM), with GSC-3 and GSC-4 being the most active compounds. These results may suggest that the presence of one or more nitrogen atoms in the ring or at an adjacent position thereto (e.g., directly attached to a ring atom) is a feature that may affect (enhance) the GSK-3 inhibition activity of newly designed small molecules.

In still an additional assay, the GSK-3 inhibition activity of GSC-1, GSC-2, GSC-3, GSC-4, GSC-5, GSC-6, and GSC-7 was tested. The ability of GSK-3 to phosphorylate p9CREB peptide substrate was measured in the presence of indicated concentrations of these compounds. The results, presented in FIGS. 7a and 7b, represent the percentage of GSK-3 activity as compared with a control incubation without inhibitors and are mean of 2 independent experiments±SEM, where each point was assayed in triplicate.

As is shown in FIGS. 7a-b, all the tested compounds were found highly active in inhibiting GSK-3 activity (IC50 values of 1-5 mM), with GSC-4 and GSC-7 being the most active compounds (IC50=0.5 Mm). These results further support the suggestion that one or more nitrogen atoms in the ring or at an adjacent position thereto (e.g., directly attached to a ring atom) is a feature that may affect (enhance) the GSK-3 inhibition activity of newly designed small molecules. These results further support the suggestion that the presence of a guanidine moiety is a feature that may affect (enhance) the GSK-3 inhibition activity of newly designed small molecules.

Figure 8:
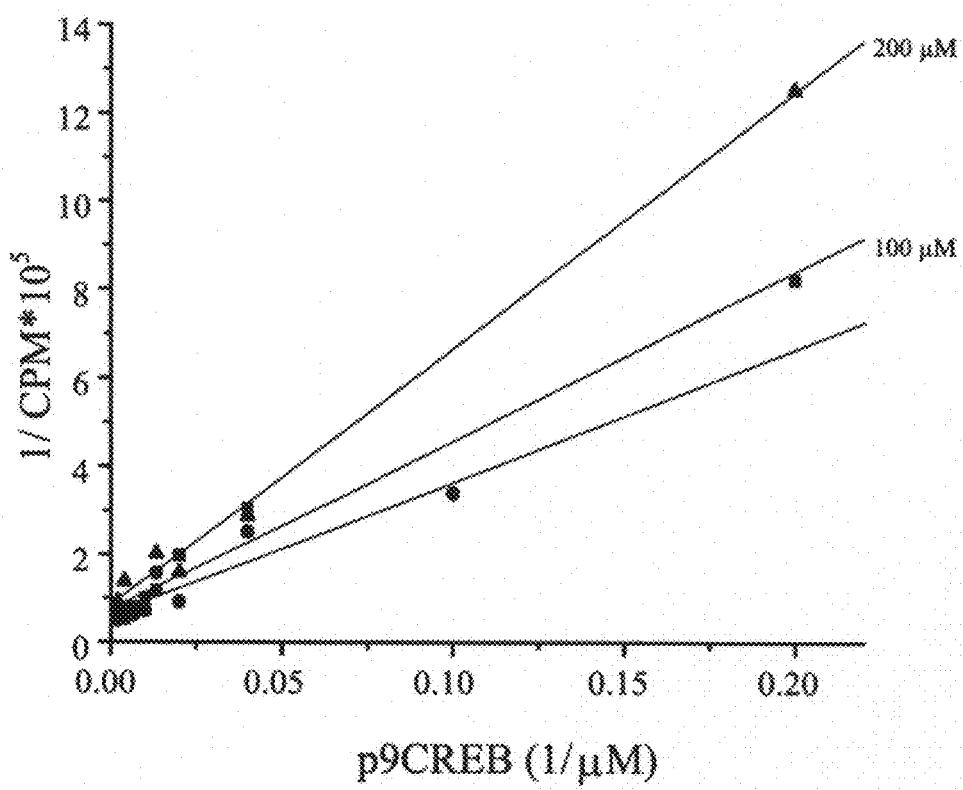
FIG. 8 presents a Lineweaver-Burk plot showing the inhibition of GSK-3 by GSC-7 at indicated concentrations, represented by phosphate incorporation into the p9CREB peptide substrate (CPM) and demonstrating that GSC-7 is a competitive specific inhibitor (Results show one representative experiment out of 3; each point is a mean of duplicate samples)

The kinetic nature of the inhibitors was studied by measuring the initial velocity as a function of the substrate concentration at several inhibitor concentrations. Lineweaver-Burk plots of the GSK-3 inhibition by these inhibitors confirmed the assumption that these are substrate-competitive inhibitors (data not shown). FIG. 8 presents the Lineweaver-Burk plot of the GSK-3 inhibition by gsc-7, as an exemplary inhibitor, represented by phosphate incorporation into p9CREB peptide substrate (CPM). Results show one representative experiment out of 3. Each point is a mean of duplicated sample.

Figure 9:
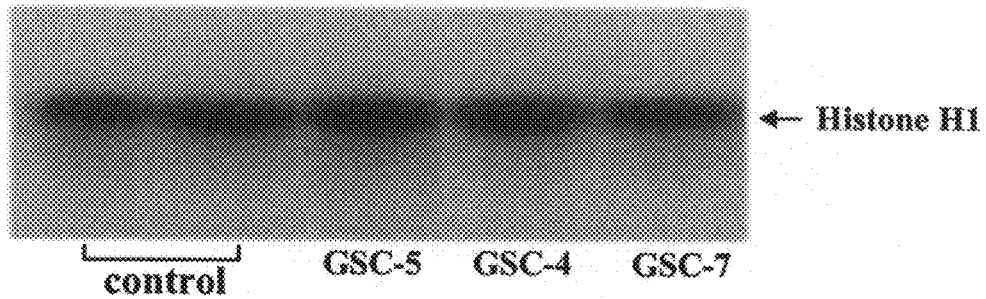
FIG. 9 is an image of a gel electrophoresis assay for CDK-2 kinase activity assayed in the presence of $^{32}$P[γ-ATP] and histone H1 as a substrate, and demonstrating the absence of inhibitory activity of GSC-4, GSC-5 and GSC-7.

The selectivity of the novel compounds towards GSK-3 was measured by evaluating the inhibition of CDK-2, a kinase closely related to GSK-3. Thus, CDK-2 activity was assayed in the presence of $^{32}P[\gamma\text{-ATP}]$ and histone H1 as a substrate. GSC-4, GSC-5 and GSC-7 were added at a final concentration of 2 mM. The results are presented in FIG. 9 and clearly show that no inhibition of histone H1 phosphorylation was observed, thus indicating high selectivity of the compounds towards GSK-3.

Activation of glycogen synthase by GSK-3 inhibitors: Activation of glycogen synthase activity in C2C12 cells treated with GSC-5 and GSC-7 was assayed as described hereinabove. The activity of glycogen synthase in cells treated with vehicle DMSO (0.1% DMSO) was normalized to 1 unit and the values for glycogen synthase activity observed in cells treated with GSK-3 (GS4 (hollow circles) GS6 (filled circles) are presented as fold stimulation over the cells treated with vehicle 0.1% HCL.

Figure 10:
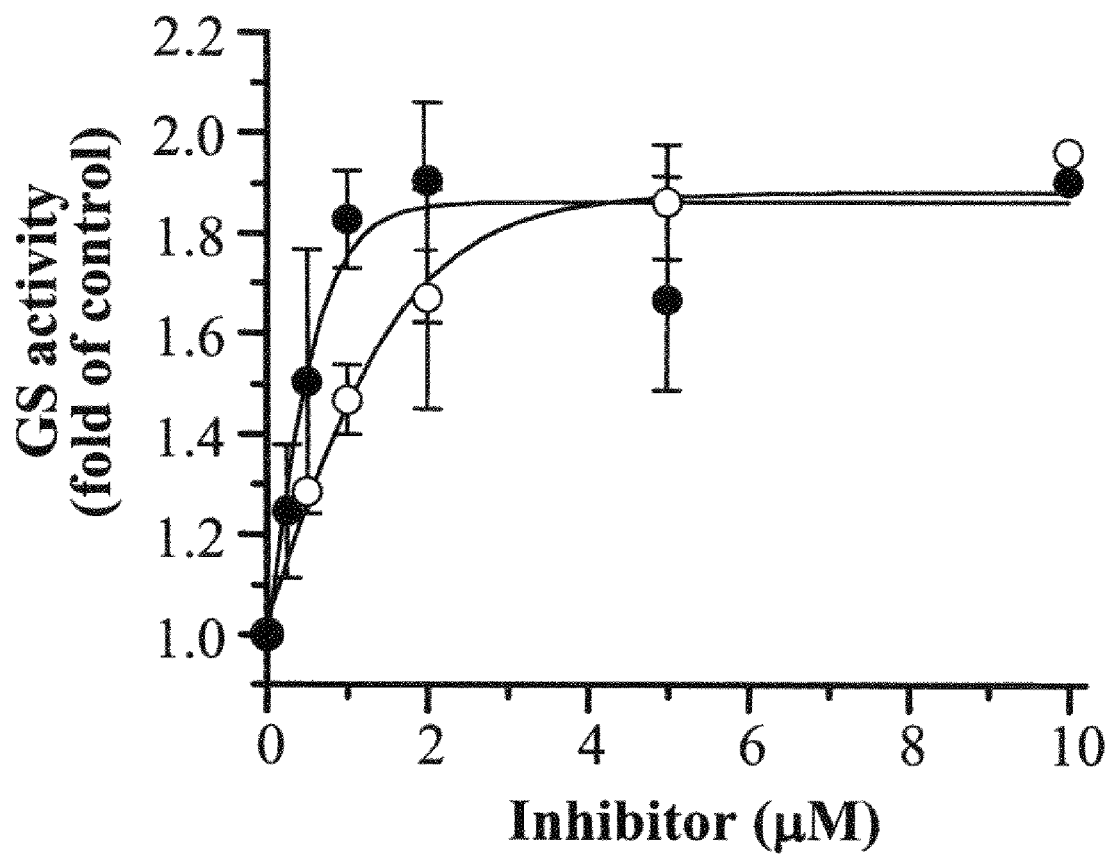
FIG. 10 presents plots demonstrating the effect of GSC-5 (hollowed circles) and GSC-7 (filled circles) on glycogen synthase activity in C2C12 cells, shown as fold stimulation over the cells treated with vehicle 0.1% HCL.

The results are presented in FIG. 10 and clearly show that both GSC-5 (hollow circles) and GSC-7 (filled circles) activated glycogen synthase by 1.5 and 1.8 fold, respectively.

Glucose Uptake: The ability of the newly designed compounds GSC-4 and GSC-21 to promote glucose uptake was tested in mouse primary adipocytes as described hereinabove. The relative [$^3$H] 2-deoxy glucose incorporation observed in non-treated adipocytes was normalized to 1 unit and the values obtained for [$^3$H] 2-deoxy glucose in adipocytes treated with GSC-4 or GSC-21 are presented as fold activation over cells treated with the peptide control, and are the mean of 6 independent experiments±SEM, where each point was assayed in triplicate.

Figure 11A:
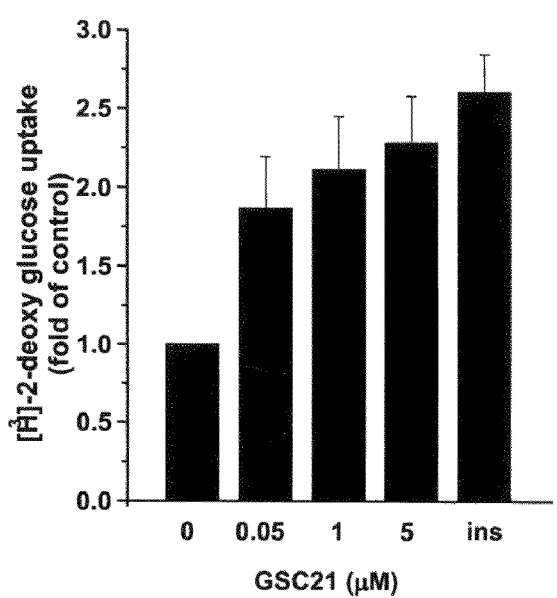
FIGS. 11a-b are bar graphs demonstrating the effect of GSC-21 (FIG. 11b) and GSC-4 (FIG. 11a) on glucose uptake in mouse adipocytes, represented by the [$^3$H] 2-deoxy glucose incorporation in cells treated with GSC-4 and GSC-21 as fold activation over cells treated with a peptide control (normalized to 1 unit)
Figure 11B:
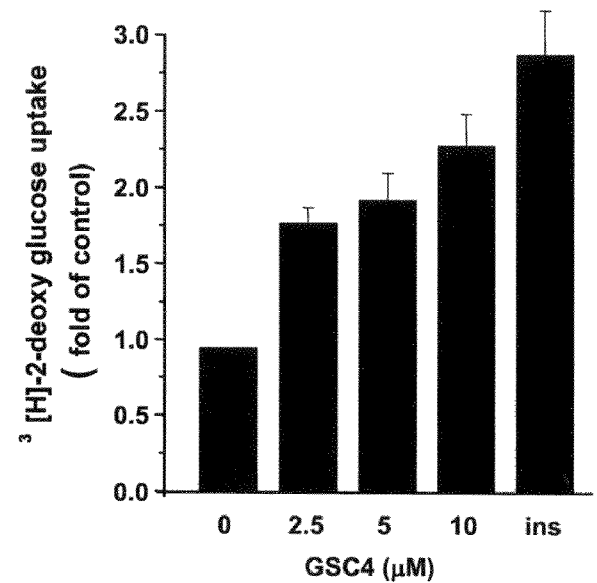

The results, presented in FIG. 11a (GSC-4) and FIG. 11b (GSC-21) show that GSC-21, at concentrations of 5 µM and 0.5 µM increased glucose uptake by 2.5-fold and 1.7 fold, respectively. A somewhat reduced effect was observed in the presence of GSC-4, which enhanced glucose uptake approximately by 2-fold at a concentration of 10 µM. As is further shown in FIGS. 11a and 11b, the activation of glucose uptake achieved by GSC-4 and GSC-21 was comparable to that achieved in the presence of 100 nM insulin. These results further demonstrate the ability of these newly designed compounds to act as insulin mimetics in potentiating insulin signaling and treating GSK-3 mediated disorders such as diabetes.

Example 4

Stimulation of the Interactions GSC Inhibitors with the GSK-3 Catalytic Domain

Simulated annealing is a molecular modeling method that is used to find stable conformations of proteins. The study examined the interaction of the newly designed GSK-3 inhibitors described above (also referred to herein as GSC molecules) with GSK-3 catalytic domain and was based on protein crystallography data of GSK-3, as taught by Ter Haar et al. (2001).

Simulated annealing uses a repetitive heating and cooling of the system to find the best energetic minima of the system. In this study, an additional parameter, the "Protein—Ligand Binding Energy" was added to the consideration of electing a new starting point in each interval of heating.

Experimental Method:

Preparation of the Complexes: the Structure of GSK Sub-unit B, as Described in Ter Haar et al. (2001) served as a starting model for the calculations. Hydrogen atoms were added to the structure and non-complete residues were fixed. Since according to the structure described in Ter Haar (supra), the phosphate is positioned between Arg96 and Arg180, the phosphates of the tested small (GSC) molecules were manually inserted to its position between Arg96 and Arg180. Four conformers with different orientations of each small molecule were generated manually as starting points while keeping the phosphate position as a common basis. The calculations were performed independently from each other. Relaxation of the system by minimization was thereafter effected, in which the ligands, hydrogen atoms, side chains and water molecules in a 15 Å radius from the phosphate atom were freed.

Simulated annealing: Stimulated annealing included the following steps:

Equilibration of 1000 steps to 1000° K;

Simulation of 7500 steps in 1000° K, whereby every 500 steps the coordinate were collected for structural diversity, total fifteen times;

Energy minimization of the fifteen structures above;

Calculation of the interaction between minimized enzyme and ligand structures above;

Selection of the best interacting structure from the fifteen minimized structures for repeating the dynamic simulation above; and Repeating the dynamic stimulation, minimization, calculation and selection fifteen times During the minimization and dynamics the hydrogen atoms, the substrate analogue and the side chains and water molecules that are in a 15 Å radius from the phosphate atom were set free.

Distant parts of the enzyme (greater than 15 Å) and the protein-backbone were fixed.

Cut off: 9.5 A distance dependent; each step was 1 fs.

The calculations were done by the program discover3/InsightII of Accelrys inc.

For the minimization and dynamics the program Discover3 was used. The force field used to calculate the energy of the system was CVFF.

Three parallel ways to produce good repertoire of interactions between GSK-3 and its ligands were chosen. Multiple starting point conformations, and molecular simulation in high temperature are well known methods that were used; in addition simulated annealing process that emphasizes the enzyme-ligand binding energy during the simulation was used.

The combined approach produced many conformations. For each starting point, the conformation with lowest binding energy in the last (15th) simulation cycle was evaluated. The binding energy was compared and the best one was chosen. In some cases more then one conformation for each ligand was analyzed.

During the simulations, the ligands were free to move. In all the simulations, the phosphate interaction with arginine residues 180 and 96 did not brake. In most of the simulations, lysine 205 did not maintain the interaction with the phosphate and created a salt bridge with glutamic acid 211.

Results:

The data obtained in this study is illustrated in FIGS. 12-17, which show the interactions between the best conformation of the analyzed compound (inhibitor) and the amino acids in the catalytic domain of GSK-3, as determined by the stimulated annealing described above. The predominant interactions between the analyzed compounds and the catalytic domain include electrostatic and/or hydrogen bonding interactions between the amine or guanidine moiety of the inhibitor and an acidic moiety at a side chain of an amino acid (e.g., of glutamic acid and aspartic acid) or the hydroxyl group of tyrosine, as well as aromatic and/or hydrophobic interactions between an aromatic moiety of the inhibitor and an aromatic or hydrocarbon side chain of an amino acid (e.g., phenylalanine, tyrosine and isoleucine). Considering the insertion of the phosphate moiety between Arg96 and Arg180, most of these interactions were found to be with Ile217, Tyr215, Phe67, Asp181, Glu97, Asp90, Asp181, and Glu200. Phe67 is an important binding moiety in the binding site of the enzyme and, moreover, it is like a door closing on the binding site.

Table 4 hereinunder presents the distances between various atoms of the analyzed inhibitor and the various amino acid residues of the enzyme which interact with these atoms. The number (presented in A) is the shorter distance between the inhibitor and the residue.

Figure 12:
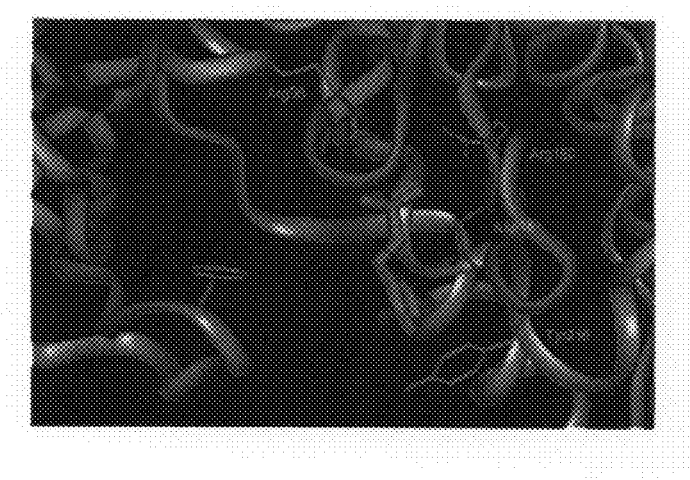
FIG. 12 presents a computed simulation of the interaction of GSC-4 with GSK-3.

Interaction of GSC-4 with GSK-3: As shown in FIG. 12, the best conformation of GSC-4 (3-guanidinyl benzylphosphate) showed hydrophobic interactions with Ile217 and Tyr216 and electrostatic interactions with Asp181 and optionally hydrogen bonding with the hydroxyl group of Tyr215.

Figure 13:
FIG. 13 presents a computed simulation of the interaction of GSC-5 with GSK-3.

Interaction of GSC-5 with GSK-3: As shown in FIG. 13, the best conformations of this compound had low interaction with the acidic groups Glu97 Asp90 or Asp181. Considerable interactions were observed with Phe67.

Figure 14:
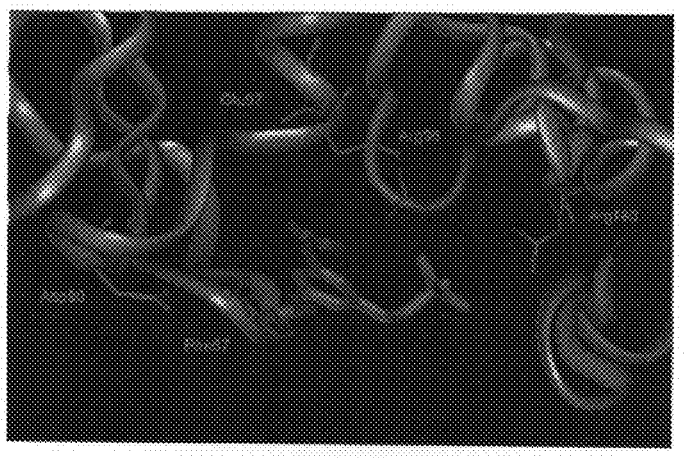
FIG. 14 presents a computed simulation of the interaction of GSC-7 with GSK-3.

Interaction of GSC-7 with GSK-3: As shown in FIG. 14, because the arms of the guanido groups that are attached to the aromatic core are too short, most of the interactions of this compound were aromatic, with Phe67, whereby the interaction with the acidic groups (e.g., Asp90 and Glu97 was weak, especially in the conformation with the lowest binding energy (3.48 Å to Asp90 and 4.92 Å from Glu97).

Figure 15:
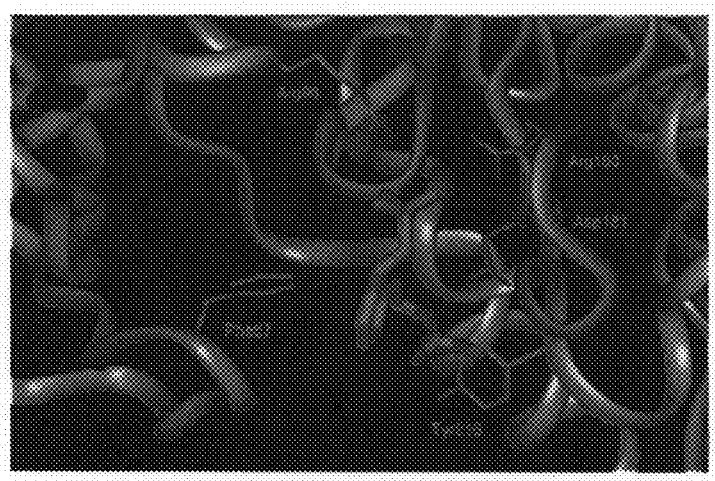
FIG. 15 presents a computed simulation of the interaction of GSC-6 with GSK-3.

Interaction of GSC-6 with GSK-3: As shown in FIG. 15, in comparison to GSC-4, in which a guanidine group is attached directly to the aromatic ring, the interaction of the guanidine group in GSC-6, in which the guanidine group is attached to the ring via an ethylene spacer, with the acid groups (e.g., Asp181) is tight. Aromatic interactions with Phe67 and Tyr216 are also observed.

Figure 16:
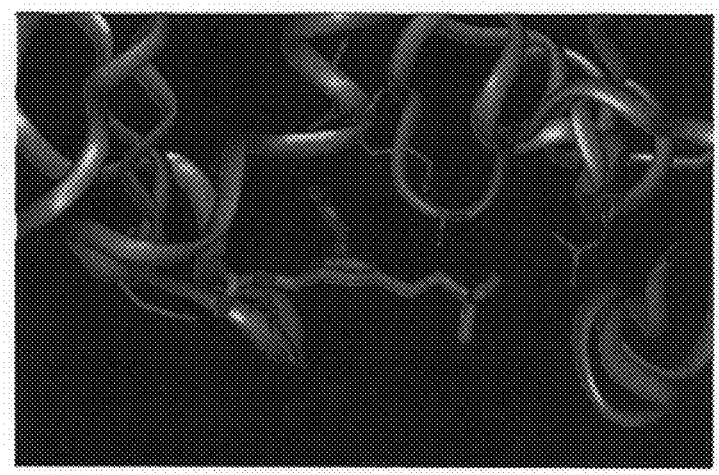
FIG. 16 presents a computed simulation of the interaction of GSC-8 with GSK-3.

Interaction of GSC-8 with GSK-3: As shown in FIG. 16, GSC-8 perfectly fits the binding site. The best conformation includes one guanido arm that points to Asp90 (1.71 Å) and the other to Glu97 (1.88 Å), and additional interactions with Phe67 (3.6), Arg96 (2.06 Å) and Arg180 (2.63 Å). The complex interaction has a good binding energy. Since the two sided guanidino groups are attached to the aromatic ring via a methylene spacer, these groups can interact simultaneously with Asp90 and Glu97. Notably, GSC-8 has a better interaction than GSC-7, in which the guanidine groups are attached directly to the ring.

Figure 17:
FIG. 17 presents a computed simulation of the interaction of GSC-9 with GSK-3.

Interaction of GSC-9 with GSK-3: As shown in FIG. 17, GSC-9 perfectly fits the binding site, with increased number of interactions. The best conformation includes one guanido arm that points to Asp90 (3.43 Å) and the other to Glu97 (2.38 Å). Although this interaction is not tight, the guanido groups interact with additional residues such as Glu200, Gln89 and the backbone o Leu88, such that the binding is strengthened. Phe67, though not strongly interacting, seems to close on the binding site.

It should be noted that other conformation of this type (Asp90 Glu97) has good energy and even tighter interaction with the carboxylic groups.

Other interactions with GSK-3 binding site: In addition to the interactions of the designed GSC molecules with the catalytic binding site of GSK-3, this study served to determine which interactions are required for optimally binding to this site. Altogether, it was found that the optimal inhibitor will interact with Phe67, Glu97, Gln89 and Asp95. These findings further support the unique features of GSK-3. While Glu97 is conserved among protein kinases and is important in catalytic activity, the roles of Phe67, Gln89 and Asp95 are novel and unique to GSK-3.

Additional studies have therefore conducted in order to design novel compounds that would interact with these residues and thus may yield specific inhibition of GSK-3.

Example 5

Chemical Syntheses of Multi Aryl/Heteroaryl GSK-3 Inhibitors (MP Small Molecules)

Based on the molecular modeling studies described hereinabove, the present inventors have now designed and successfully prepared a novel family of GSK-3 inhibitors, in which a multi aryl and/or heteroaryl-containing skeleton serves as a spacer between the phosphate moiety and the amine-containing moiety (e.g., guanidine).

The general procedures and data for each step in the synthetic pathway of representative compounds of this family are set forth below. The chemical structures of the compounds are presented in FIG. 18.

Experimental Data:

Proton, carbon, and phosphorus nuclear magnetic resonance spectra were obtained on a Bruker AVANCE 200 or 400 MHz spectrometer and are reported in ppm (δ). Tetramethylsilane (TMS) was used as an internal standard for proton spectra, unless otherwise indicated; phosphoric acid was used as an internal standard for phosphorus spectra; and the solvent peak was used as the reference peak for carbon and fluorine spectra.

Mass spectra were obtained on a Micromass VG autospec M250

Preparation of N-(iodophenyl),N',N"-bis(tert-butoxycarbonyl)guanidines

The general procedure for the preparation of N-(iodophenyl),N',N"-bis(tert-butoxycarbonyl) guanidines is depicted in Scheme 10 below.

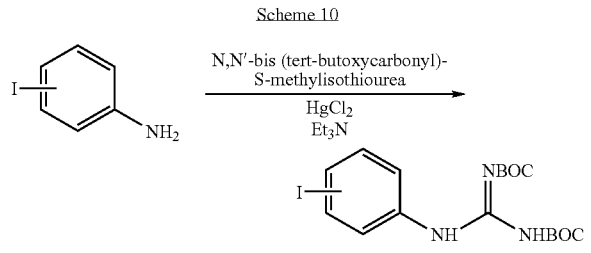

A solution of N,N'-bis(tert-butoxycarbonyl)-S-methylisothiourea (1.32 gram, 4.4 mmol, 1.1 molequivalents), mercury chloride (1.22 gram, 4.4 mmol, 1.1 molequivalents) and triethyl amine (1.72 ml, 12.0 mmol, 3.0 molequivalents) was added to iodoaniline (0.88 gram, 4.0 mmol, 1.0 molequivalent) in dry DMF (15 ml) and the resulting mixture was stirred at room temperature for 5 hours. The mixture was then poured to ethyl acetate (60 ml) and filtered through celite. The organic layer was washed with water (50 ml), saturated aqueous NH$_4$Cl (50 ml) and brine and was dried with MgSO$_4$. The solvent was evaporated under reduced pressure. The crude compound was sufficiently pure and was used without further purification.

Using this general procedure, the following compounds have been prepared:

N-(3-iodophenyl),N',N"-bis(tert-butoxycarbonyl) guanidine

Yield: 85%
$^1$H NMR (200 MHz, CDCl$_3$): δ=11.60 (s, 1H), 10.33 (s, 1H), 7.89 (s, 1H), 7.71 (d, J=8.3 Hz, 1H), 7.45 (d, J=7.8 Hz, 1H), 7.05 (t, J=8.1 Hz, 1H), 1.53 (bs, 18H).
$^{13}$C NMR (100 MHz, CDCl$_3$): δ=162.5, 153.2, 137.7, 133.9, 130.6, 130.4, 121.5, 93.7, 84.3, 80.5, 27.9, 27.3.

N-(2-iodophenyl),N'N"-bis(tert-butoxycarbonyl) guanidine

This compound was obtained as described above, only stirring the reaction mixture continued four days.

Yield: 85%.
$^1$H NMR (200 MHz, CDCl$_3$): δ=11.64 (s, 1H), 10.17 (s, 1H), 7.91 (d, J=8.1 Hz), 7.64 (d, J=7.9 Hz, 1H), 7.18 (t, J=7.7 Hz, 1H), 6.70 (t, J=7.6 Hz, 1H), 1.42 (bs, 9H), 1.36 (bs, 9H).
$^{13}$C NMR (50 MHz, CDCl$_3$): δ=163.2, 153.8, 152.8, 138.8, 137.9, 128.4, 126.6, 125.9, 92.4, 83.4, 79.3, 27.9

N-(4-iodophenyl),N',N"-bis(tert-butoxycarbonyl) guanidine

Yield: 85%
$^1$H NMR (200 MHz, CDCl$_3$): δ=11.63 (s, 1H), 10.44 (s, 1H), 7.62 (d, J=8.7 Hz, 2H), 7.38 (d, J=8.7 Hz, 2H), 1.52 (bs, 9H), 1.50 (bs, 9H).
$^{13}$C NMR (50 MHz, CDCl$_3$): δ=163.1, 153.2, 137.7, 136.6, 123.9, 88.2, 83.3, 79.8, 28.0

Preparation of N-(TMS-ethynylphenyl),N',N'-bis(tert-butoxycarbonyl) guanidines

The general procedure for the preparation of N-(TMS-ethynylphenyl),N',N"-bis(tert-butoxycarbonyl)guanidines is depicted in Scheme 11 below.

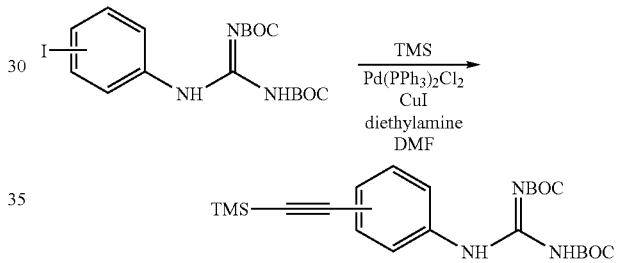

A solution of Pd(PPh$_3$)$_2$Cl$_2$ (16 mg, 0.02 mmol, 0.02 molequivalent), CuI (8 mg, 0.05 mmol, 0.04 molequivalent), trimethylsilylacetylene (0.20 ml, 1.2 mmol, 1.1 molequivalent) in diethylamine (1.8 ml, 14.8 mmol, 16 equiv) and dimethylforamide (0.6 ml) was added to N-(iodophenyl),N', N"-bis(tert-butoxycarbonyl) guanidine (0.50 gram, 1.1 mmol, 1 molequivalent) and the resulting mixture was stirred overnight under nitrogen atmosphere at room temperature. The reaction mixture was thereafter poured into water (8 ml) and extracted three times with diethylether (3×8 ml). The combined organic layers were washed with water and brine (8 ml), the aqueous phase was re-extracted two times with diethylether (2×8 ml), and the combined organic layers were dried with MgSO$_4$ and concentrated under reduced pressure. The residue was purified by flash chromatography on silica gel (using a gradient eluent of hexanes and a 20:80 ethyl acetate: hexanes mixture).

Using this general procedure, the following compounds were prepared:

N-(3-TMS-ethynylphenyl),N N'-bis(tert-butoxycarbonyl) guanidine

Yield: 80%
$^1$H NMR (200 MHz, CDCl$_3$): δ=11.61 (s, 1H), 10.36 (s, 1H), 7.77 (d, J=8.0 Hz, 1H), 7.58 (bs, 1H), 7.26 (t, J=7.7 Hz, 1H), 7.19 (d, J=7.7 Hz, 1H), 1.51 (bs, 9H), 1.45 (bs, 9H), 0.24 (s, 9H).

$^{13}$C NMR (100 MHz, CDCl$_3$): δ=163.1, 154.4, 137.9, 129.9, 126.1, 124.7, 123.4, 105.7, 95.4, 85.1, 81.0, 29.1, 0.9

N-(2-TMS-ethynylphenyl),N N'-bis(tert-butoxycarbonyl) guanidine

This compound was obtained as described hereinabove, only stirring was continued for seven days.

Yield: 80%.

$^1$H NMR (200 MHz, CDCl$_3$): δ=11.69 (s, 1H), 10.80 (s, 1H), 8.53 (d, J=8.4 Hz, 1H), 7.41 (dt, J=9.1 Hz, 1.4 Hz, 1H), 7.32 (dd, J=8.3, 1.2 Hz, 1H), 7.02 (dt, J=7.6 Hz, 1.0 Hz, 1H), 1.53 (bs, 18H), 0.28 (s, 9H).

$^{13}$CNMR (100 MHz, CDCl$_3$): δ=164.5, 154.5, 153.5, 140.1, 133.3, 130.4, 124.7, 123.4, 115.1, 102.9, 101.1, 84.3, 80.7, 29.2, 0.9.

N-(4-TMS-ethynylphenyl),N',N'-bis(tert-butoxycarbonyl) guanidine

Yield: 80%

$^1$H NMR (200 MHz, CDCl$_3$): δ=11.61 (s, 1H), 10.42 (s, 1H), 7.58 (d, J=8.7 Hz, 2H), 7.41 (d, J=8.7 Hz, 2H), 1.51 (bs, 9H), 1.49 (bs, 9H), 0.24 (s, 9H).

$^{13}$C NMR (100 MHz, CDCl$_3$): δ=164.7, 164.4, 154.3, 137.8, 134.2, 133.2, 122.6, 120.4, 118.6, 84.9, 83.8, 80.7, 80.1, 29.3, 0.9

Preparation of N-(ethynylphenyl),N',N'-bis(tert-butoxycarbonyl) guanidines

The general procedure for the preparation of N-(ethynylphenyl),N',N"-bis(tert-butoxycarbonyl)guanidines is depicted in Scheme 12 below.

Scheme 12

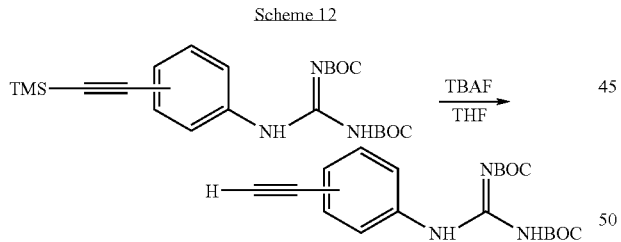

A solution of N-(TMS-ethynylphenyl),N',N'-bis(tert-butoxycarbonyl) guanidine (97 mg, 0.24 mmol, 1 molequivalent) in THF (3 ml) was stirred at −5° C. (using an ice:salt bath) under nitrogen atmosphere. TBAF (1.0 M in THF, 0.4 ml, 0.4 mmol, 1.6 molequivalent) was added dropwise over several minutes and the mixture was allowed to warm to room temperature and stirred for 3 hours. The solvent was thereafter evaporated under reduced pressure and the product extracted with ethyl acetate (6 ml). The organic phase was washed three times with water (3×15 ml) and brine, dried with MgSO$_4$ and evaporated under reduced pressure. The crude compound was sufficiently pure and was used without further purification.

Using this general procedure, the following compounds were prepared:

N-(3-ethynylphenyl),N',N'-bis(tert-butoxycarbonyl) guanidine

Yield: 85%

$^1$H NMR (200 MHz, CDCl$_3$): δ=11.62 (s, 1H), 10.36 (s, 1H), 7.75 (d. J=7.4 Hz, 1H), 7.63 (bs, 1H), 7.21-7.33 (m, 2H), 3.07 (s, 1H), 1.52 (bs, 18H).

$^{13}$C NMR (100 MHz, CDCl$_3$): δ=162.1, 153.4, 136.8, 128.9, 128.4, 125.3, 125.2, 122.5, 83.8, 83.1, 79.8, 28.0.

N-(2-ethynylphenyl),N',N'-bis(tert-butoxycarbonyl) guanidine

Yield: 85%

$^1$H NMR (200 MHz, CDCl$_3$): δ=11.64 (s, 1H), 10.88 (s, 1H), 8.49 (d, J=8.4 Hz, 1H), 7.33-7.47 (m, 2H), 7.05 (dt, J=7.7 Hz, 2.1 Hz, 1H), 2.97 (s, 1H), 1.53 (bs, 18H).

$^{13}$C NMR (50 MHz, CDCl$_3$): δ=163.3, 153.4, 152.6, 139.4, 132.1, 129.7, 123.6, 122.4, 113.2, 84.4, 83.4, 79.7, 79.1, 28.0.

N-(4-ethynylphenyl),N',N'-bis(tert-butoxycarbonyl) guanidine

Yield: 85%

$^1$H NMR (200 MHz, CDCl$_3$): δ=11.61 (s, 1H), 10.44 (s, 1H), 7.62 (d, J=10.8 Hz, 2H), 7.45 (d, J=8.7 Hz, 2H), 3.07 (s, 1H), 1.53 (bs, 18H).

$^{13}$C NMR (100 MHz, CDCl$_3$): δ=164.4, 154.3, 138.4, 133.8, 122.6, 119.0, 85.0, 84.5, 80.9, 29.2.

Preparation of Azidobenzylalcohols

The general procedure for the preparation of azidobenzylalcohols is depicted in Scheme 13 below.

Scheme 13

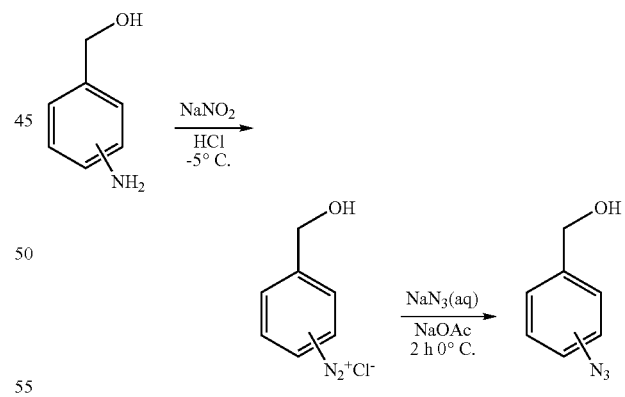

A 50 ml round bottomed flask was charged with a stirring bar, 25 ml 2N HCl, and aminobenzylalcohol (2.15 grams, 17.5 mmol, 1 molequivalent). The solution was cooled to −5° C. in a salt-ice bath. An ice-cold solution of sodium nitrite (1.45 gram, 21 mmol, 1.2 molequivalent) in 5 ml water was slowly added over five minutes such that the temperature of the reaction did not rise above −3° C. After five minutes, 125 mg urea was added to destroy the excess nitrous acid. The solution of the resulting diazonium salt was then added during five minutes to a stirred ice-cold solution of sodium azide (2.28 grams, 35 mmol, 2 molequivalent) and sodium acetate (4.20 grams, 51 mmol, 3 molequivalent) in 25 ml water. The mixture was stirred for 2 hours at 0° C., and the dark oily product was extracted with diethyl ether (2×50 ml). The ethereal solution was washed with 1N NaOH (2×50 ml) and water (2×50 ml), dried over MgSO$_4$, and evaporated to dryness. The obtained compound was sufficiently pure and was used without further purification.

Using this general procedure, the following compounds were prepared:

3-azidobenzylalcohol

Yield: 83%
$^1$H NMR (200 MHz, CDCl$_3$): δ=7.29 (t, J=7.6 Hz, 1H), 7.04 (bd, J=7.8 Hz, 1H), 6.95 (s, 1H), 6.91 (d, J=8 Hz, 1H), 4.55 (s, 2H).
$^{13}$C NMR (100 MHz, CDCl$_3$): δ=142.8, 140.1, 129.8, 122.5, 118.0, 117.1, 64.4.

4-azidobenzylalcohol

Yield: 90%
$^1$H NMR (200 MHz, CDCl$_3$): δ=7.28 (d, J=8.4 Hz, 2H), 6.97 (d, J=8.4 Hz, 2H), 4.55 (s, 2H), 3.00 (s, 1H).
$^{13}$C NMR (100 MHz, CDCl$_3$): δ=139.1, 137.5, 128.4, 118.9, 64.2

Preparation of di-tert-butyl, azidobenzyl phosphates

The general procedure for the preparation of di-tert-butyl, azidobenzyl phosphates is depicted in Scheme 14 below.

Scheme 14

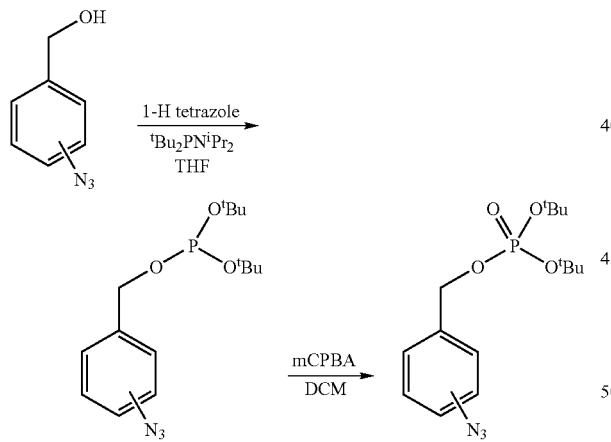

1-H-tetrazole solution (0.45 M in acetonitrile, 44.7 ml, 20.2 mmol, 3 molequivalents) was added in one portion to a stirred solution of azidobenzylalcohol (1.0 gram, 6.7 mmol, 1 molequivalent) and di-tert-butyl diisopropyl phosphoramidite (3.17 ml, 10.1 mmol, 1.3 molequivalent) in dry THF (7 ml). The resulting mixture was stirred for 30 minutes at 20° C. was thereafter cooled to −40° C. (using a dry ice/acetonitrile bath). A solution of 85% mCPBA (1.35 gram in 2.4 ml DCM, 10.05 mmol, 1.5 molequivalent) in DCM (9 ml) was then rapidly added while keeping the reaction temperature below 0° C. The reaction mixture was allowed to reach room temperature and after stirring for 20 minutes 10% aqueous NaHSO$_3$ (24 ml) was added and the mixture was stirred for additional 10 minutes. The mixture was then extracted with ether (120 ml) and the aqueous phase was discarded. The ethereal phase was washed with 10% aqueous NaHSO$_3$ (2×48 ml) and saturated aqueous NaHCO$_3$ (2×48 ml), dried on MgSO$_4$ and filtered. The solvent was evaporated and the residue was chromatographed on silica gel column (using a gradient eluent of hexanes to a 40:60 mixture of ethyl acetate/hexanes) to give the product.

Using this general procedure, the following compounds were prepared:

Di-tert-butyl, 3-azidobenzyl phosphate

Yield: 10%
$^1$H NMR (200 MHz, CDCl$_3$): δ=7.32 (t, J=7.7 Hz, 1H), 7.12 (d, J=7.6 Hz, 1H), 7.05 (bs, 1H), 6.95 (d, J=6.6 Hz, 1H), 4.97 (d, J=7.4 Hz, 2H), 1.47 (bs, 18H).
$^{13}$C NMR (100 MHz, CDCl$_3$): δ=140.1, 138.6, 129.6, 123.6, 118.4, 117.7, 82.5, 67.4, 29.7. $^{31}$P NMR (81 MHz, CDCl$_3$): δ=−9.3

Di-tert-butyl, 4-azidobenzyl phosphate

Yield: 12%
$^1$H NMR (200 MHz, CDCl$_3$): δ=7.33 (d, J=8.4 Hz, 2H), 6.98 (d, J=8.4 Hz, 2H), 4.93 (d, J=7.8 Hz, 2H), 1.40 (bs, 18H).
$^{13}$C NMR (100 MHz, CDCl$_3$): δ=139.7, 133.4, 129.2, 118.9, 82.5, 67.6, 29.8. $^{31}$P NMR (81 MHz, CDCl$_3$): δ=−9.3

Dipolar Cycloaddition of azidobenzyl phosphates and N-(ethynylphenyl),N',N"-bis(tert-butoxycarbonyl)guanidines The general procedure for the dipolar cycloaddition of the azides and the acetylenes described hereinabove is depicted in Scheme 15 below.

Scheme 15

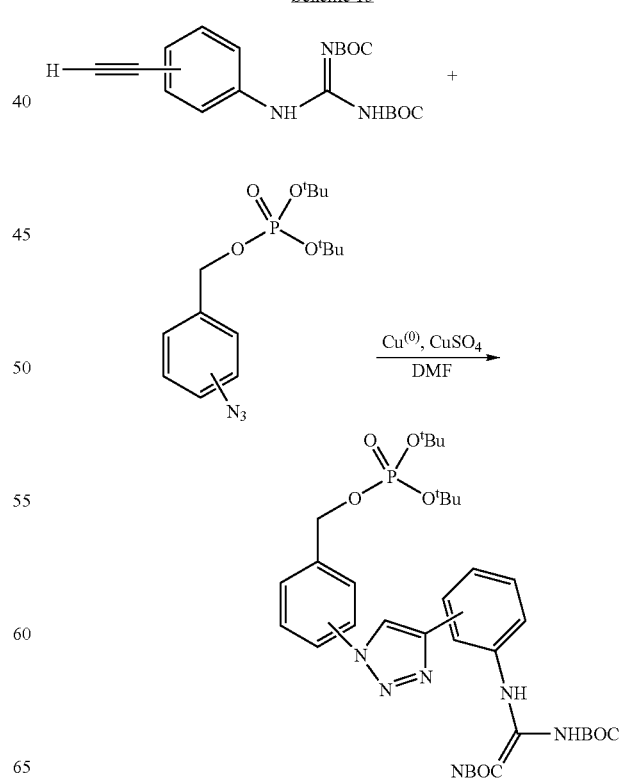

CuSO₄ (0.02 gram, 0.125 mmol, 0.5 molequivalent) and Cu wires, were added to a solution of a N-(ethynylphenyl), N',N'-bis(tert-butoxycarbonyl) guanidine (0.07 gram, 0.212 mmol, 1 molequivalent) and a di-tert-butyl, azidobenzyl phosphate (0.07 gram, 0.205 mmol, 1 molequivalent) in DMF (5 ml) and the resulting mixture was stirred under nitrogen atmosphere overnight. The solution was thereafter extracted with ethyl acetate (10 ml) and the organic layer was washed three times with brine, while the aqueous layer was re-extracted two times with ethyl acetate (2×10 ml). The combined organic phase was concentrated under reduced pressure. The residue was purified by chromatography on silica gel column (using a gradient eluent of hexanes to a 60:40 ethyl acetate/hexanes mixture) to give the protected addition product.

Using this general procedure, the following compounds were prepared:

Protected 3-(4-(3-guanidinophenyl)-1,2,3-triazol-1-yl)benzylphosphoric acid hydrochloride (Protected 3-Gua-3-Phos)

Yield: 85%

¹H NMR (400 MHz, CDCl₃): δ=11.61 (s, 1H), 10.42 (s, 1H), 8.26 (s, 1H), 8.01 (s, 1H), 7.81 (s, 1H), 7.69-7.74 (m, 2H), 7.61 (d, J=7.6 Hz, 1H), 7.48 (t, J=8 Hz, 1H), 7.41 (d, J=7.6 Hz, 1H), 7.35 (t, J=7.9 Hz, 1H), 5.04 (d, J=8 Hz, 2H), 1.51 (bs, 18H).

¹³C NMR (100 MHz, CDCl₃): δ=164.4, 154.7, 154.3, 148.9, 140.0, 138.4, 138.1, 131.8, 130.8, 130.5, 128.5, 123.4, 123.1, 120.8, 120.4, 120.3, 119.0, 84.8, 83.8, 80.6, 68.4, 30.9, 30.3.

³¹P NMR (81 MHz, CDCl₃): δ=−9.3

Protected 3-(4-(2-guanidinophenyl)-1,2,3-triazol-1-yl)benzyl phosphoric acid hydrochloride (Protected 2-Gua-3-Phos)

This compound was obtained as described hereinabove, except that the reaction mixture was stirred for four days.

Yield: 50%

¹H NMR (400 MHz, CDCl₃): δ=8.33 (bs, 1H), 7.98-8.00 (m, 2H), 7.88 (s, 1H), 7.72 (m, 1H), 7.47 (bs, 2H), 7.36 (t, J=7.2 Hz, 1H), 7.23 (t, J=7.6 Hz, 1H), 5.07 (d, J=8.4 Hz, 2H), 1.51 (bs, 18H).

Partial ¹³C NMR (100 MHz, CDCl₃): δ=155.1, 146.1, 140.0, 138.2, 131.4, 129.9, 128.5, 124.7, 120.9, 120.5, 83.8, 68.5, 30.9, 29.1.

³¹P NMR (81 MHz, CDCl₃): δ=−9.3

MS (FAB): m/z calcd for C₃₄H₄₉N₆O₈P (MH⁺)=701.3; found=701.2.

Protected 3-(4-(4-guanidinophenyl)-1,2,3-triazol-1-yl)benzylphosphoric acid hydrochloride (Protected 4-Gua-3-Phos)

Yield: 73%

¹H NMR (400 MHz, CDCl₃): δ=11.67 (s, 1H), 10.48 (s, 1H), 8.20 (s, 1H), 7.86-7.90 (m, 3H), 7.71-7.79 (m, 3H), 7.44-7.58 (m, 2H), 5.10 (d, J=7.7 Hz, 2H), 1.50 (m, 18H).

Partial ¹³C NMR (100 MHz, CDCl₃): δ=163.2, 153.3, 147.9, 138.8, 137.0, 129.8, 127.4, 126.3, 122.3, 119.8, 119.1, 117.2, 83.8, 82.7, 79.7, 67.3, 29.8, 28.0.

³¹P NMR (81 MHz, CDCl₃): δ=−9.3

Protected 4-(4-(3-guanidinophenyl)-1,2,3-triazol-1-yl)benzylphosphoric acid hydrochloride (Protected 3-Gua-4-Phos)

Yield: 90%

¹H NMR (200 MHz, CDCl₃): δ=11.63 (s, 1H), 10.44 (s, 1H), 8.26 (s, 1H), 8.07 (s, 1H), 7.64-7.80 (m, 4H), 7.52-7.56 (bd, 2H), 7.38 (m, 1H), 5.05 (d, J=7.4 Hz, 2H), 1.51 (bs, 9H), 1.24 (bs, 9H).

¹³C NMR (100 MHz, CDCl₃): δ=163.1, 153.4, 153.1, 147.8, 137.2, 136.5, 130.6, 129.4, 128.7, 127.8, 122.1, 121.9, 120.1, 119.2, 117.8, 83.7, 82.5, 79.5, 67.2, 29.6, 27.9.

³¹P NMR (81 MHz, CDCl₃): δ=−9.3

Protected 4-(4-(2-guanidinophenyl)-1,2,3-triazol-1-yl)benzyl phosphoric acid hydrochloride (Protected 2-Gua-4-Phos)

This compound was obtained as described hereinabove, except that the reaction mixture was stirred for 48 hours and reaction was still no completed.

Yield: 43%

¹H NMR (400 MHz, CDCl₃): δ=10.53 (bs, 1H), 8.34 (bs, 1H), 7.81-7.85 (bd, 3H), 7.50-7.55 (m, 2H), 7.38 (t, J=7.4 Hz, 1H), 7.21-7.29 (m, 2H), 5.06 (d, J=7.6 Hz, 2H), 1.49 (bs, 9H), 1.25 (bs, 9H).

Partial ¹³C NMR (100 MHz, CDCl₃): δ=153.9, 144.8, 137.3, 136.6, 128.8, 128.6, 127.9, 127.8, 125.6, 124.5, 123.7, 120.3, 82.7, 82.5, 67.3, 29.5, 28.0.

³¹P NMR (81 MHz, CDCl₃): δ=−9.3

Protected 4-(4-(4-guanidinophenyl)-1,2,3-triazol-1-yl)benzyl phosphoric acid hydrochloride (Protected 4-Gua-4-Phos)

Yield: 75%

¹H NMR (200 MHz, CDCl₃): δ=11.64 (s, 1H), 10.45 (s, 1H), 8.19 (s, 1H), 7.69-7.88 (m, 6H), 7.56 (d, J=8.4 Hz, 2H), 5.06 (d, J=7.6 Hz, 2H), 1.52 (bs, 18H).

¹³C NMR (100 MHz, CDCl₃): δ=163.3, 153.4, 137.5, 137.4, 136.9, 136.6, 128.8, 127.9, 126.5, 126.3, 122.4, 120.3, 83.8, 82.7, 79.7, 67.4, 29.8, 28.1

³¹P NMR (81 MHz, CDCl₃): δ=−9.3

Preparation of MP-1-MP-6 (deprotection of the t-Bu and BOC groups)

The general procedure for deprotecting the t-Bu and BOC protecting groups to thereby obtain the final products is depicted in Scheme 15 below.

Scheme 15

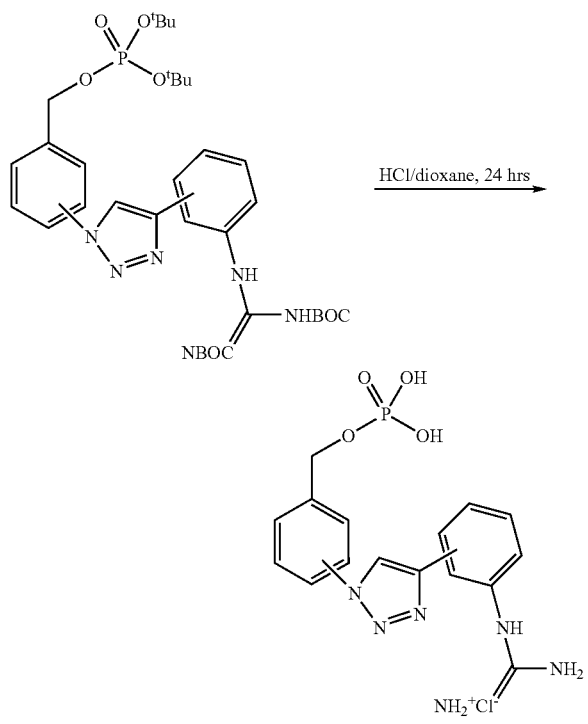

A solution of HCl (4 M in dioxane, 2 ml, 8 mmol, 2.6 molequivalents) and dioxane (6 ml) was added to the protected compounds at 20° C. and the resulting mixture was stirred overnight. The dioxane was thereafter evaporated under reduced pressure to give the final products.

Using this general procedure, the following compounds were prepared (see, FIG. 18, for the chemical structures of the compounds):

3-(4-(3-guanidinophenyl)-1,2,3-triazol-1-yl)benzyl phosphoric acid hydrochloride (3-Gua-3-Phos, MP1)

Yield: 70%

$^1$H NMR (400 MHz, DMSO-d$_6$): δ=10.02 (s, 1H), 9.39 (s, 1H), 7.96 (s, 1H), 7.85 (m, 2H), 7.79 (s, 1H), 7.60 (t, J=7.6 Hz, 1H), 7.54 (bs, 2H), 7.49 (t, J=7.2 Hz, 1H), 7.21 (d, J=7.2 Hz, 1H), 4.98 (d, J=7.2 Hz, 2H), $^{13}$C NMR (100 MHz, DMSO-d$_6$): δ=157.5, 148.1, 141.3, 138.0, 137.5, 133.1, 131.9, 131.5, 128.9, 125.8, 124.8, 122.8, 121.7, 120.7, 120.0, 67.5.

$^{31}$P-NMR (81 MHz, DMSO-d$_6$): δ=−0.6

MS (FAB): m/z calcd for $C_{16}H_{18}N_6O_4P$ (MH$^+$)=389.1; found=389.0.

3-(4-(2-guanidinophenyl)-1,2,3-triazol-1-yl)benzyl phosphoric acid hydrochloride (2-Gua-3-Phos, MP3)

Yield: 72%

$^1$H NMR (400 MHz, DMSO-d$_6$): δ=10.01 (s, 1H), 9.34 (s, 1H), 7.98-8.07 (m, 2H), 7.87 (s, 1H), 7.37-7.56 (m, 6H), 4.89 (bs, 2H).

$^{13}$C NMR (100 MHz, DMSO-d$_6$): δ=158.1, 155.4, 152.9, 145.3, 141.2, 137.9, 132.7, 131.5, 131.2, 130.7, 130.4, 129.2, 123.0, 120.8, 120.2, 67.8.

$^{31}$P NMR (81 MHz, DMSO-d$_6$): δ=−0.6

MS (FAB): m/z calcd for $C_{16}H_{18}N_6O_4P$ (MH$^+$)=389.1; found=389.0.

3-(4-(4-guanidinophenyl)-1,2,3-triazol-1-yl)benzyl phosphoric acid hydrochloride (4-Gua-3-Phos, MP4)

Yield: 72%

$^1$H NMR (400 MHz, DMSO-d$_6$): δ=10.21 (s, 1H), 9.37 (s, 1H), 7.97-8.13 (m, 3H), 7.61 (bs, 3H), 7.33 (bs, 3H), 4.84 (bs, 2H).

$^{13}$C NMR (50 MHz, DMSO-d$_6$): δ=156.4, 147.0, 140.1, 136.9, 135.5, 130.4, 129.0, 127.7, 126.9, 125.1, 120.2, 119.6, 118.9, 66.7.

$^{31}$P NMR (81 MHz, DMSO-d$_6$): δ=−0.6

MS (FAB): m/z calcd for $C_{16}H_{18}N_6O_4P$ (MH$^+$)=389.1; found=389.0.

4-(4-(3-guanidinophenyl)-1,2,3-triazol-1-yl)benzyl phosphoric acid hydrochloride (3-Gua-4-Phos, MP5)

Yield: 75%

$^1$H NMR (200 MHz, DMSO-d$_6$): δ=10.20 (s, 1H), 9.38 (s, 1H), 7.18-7.90 (m, 9H), 4.69 (bs, 2H).

$^{13}$C NMR (100 MHz, DMSO-d$_6$): δ=156.4, 146.8, 138.4, 136.2, 131.9, 130.7, 129.0, 127.9, 124.4, 123.6, 121.4, 120.5, 120.1, 66.6.

$^{31}$P NMR (81 MHz, DMSO-d$_6$): δ=−0.6

MS (FAB): m/z calcd for $C_{16}H_{16}N_6O_4P$ {(M-H)$^-$}=387.1; found=387.1

4-(4-(2-guanidinophenyl)-1,2,3-triazol-1-yl)benzyl phosphoric acid hydrochloride (2-Gua-4-Phos, MP6)

This compound was obtained as described hereinabove, except that the mixing was continued for 22 hours.

Yield: 76%

$^1$H NMR (400 MHz, DMSO-d$_6$): δ=9.91 (s, 1H), 8.47 (s, 1H), 7.87 (bs, 2H), 7.07-7.49 (m, 7H), 4.46 (bs, 2H).

$^{13}$C NMR (100 MHz, DMSO-d$_6$): δ=156.8, 144.0, 137.9, 136.3, 136.0, 131.9, 131.4, 130.8, 130.0, 129.2, 127.9, 121.7, 120.5, 66.6.

$^{31}$P NMR (81 MHz, DMSO-d$_6$): δ=−0.6

MS (FAB): m/z calcd for $C_{16}H_{12}D_4N_6O_4P$ {(M-H)$^-$}=391.1; found=391.4.

4-(4-(4-guanidinophenyl)-1,2,3-triazol-1-yl)benzyl phosphoric acid hydrochloride (4-Gua-4-Phos, MP2)

Yield: 75%

$^1$H NMR (400 MHz, DMSO-d$_6$): δ=10.31 (s, 1H), 9.35 (s, 1H), 7.94-8.02 (m, 3H), 7.59-7.68 (m, 3H), 7.33-7.37 (m, 3H), 4.98 (d, J=7.6 Hz, 2H).

$^{31}$P NMR (81 MHz, DMSO-d$_6$): δ=−0.6

Example 6

GSK-3 Inhibition by MP Molecules

Figure 19:
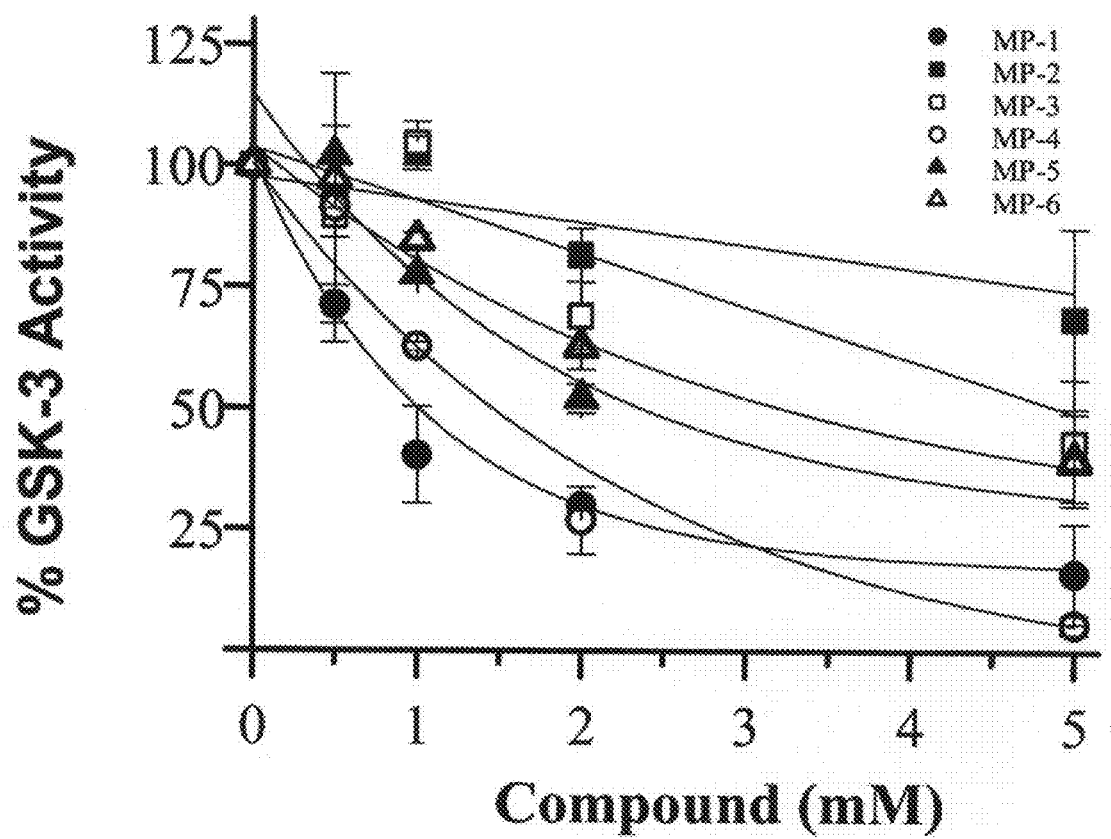
FIG. 19 presents comparative plots demonstrating the GSK-3 inhibition activity of MP-1, MP-2, MP-3, MP-4, MP-5 and MP-6 in in vitro inhibition assays with p9CREB peptide substrate.

The ability of GSK-3 to phosphorylate p9CREB peptide substrate was measured in the presence of indicated concentrations of MP molecules, using the protocol described hereinabove in Example 3. The results, presented in FIG. 19, represent the percentage of GSK-3 activity in control incubation in which inhibitors were omitted. Results are mean of 2 independent experiments±SEM, where each point was assayed in duplicate.

As shown in FIG. 19, MP-1 and MP-4 were found to exhibit the best inhibition activity with IC50 values of about 1 mM.

TABLE 2

REMARK FILENAME = "refine_1_4.pdb"
REMARK
================================================================
REMARK overall, bonds, angles, improper, vdw, noe, cdih
REMARK energies: 49.6206, 2.76302, 18.089, 2.9318, 0.894357, 24.9424,
$CDIH
REMARK
================================================================
REMARK bonds, angles, impropers, noe, cdih
REMARK rms-d: 4.019702E−03, 0.622994, 0.465061, 9.195132E−02, 0
REMARK
================================================================
REMARK noe, cdih
REMARK violations.: 0, 0
REMARK
================================================================
REMARK DATE: 27 Apr. 2000 08:12:42          created by user: orish

| | | | | | | | | | |
|---|---|---|---|---|---|---|---|---|---|
| ATOM | 1 | CA | ILE | 1 | 11.861 | −0.265 | −1.755 | 1.00 | 0.00 |
| ATOM | 2 | HA | ILE | 1 | 11.773 | 0.710 | −1.305 | 1.00 | 0.00 |
| ATOM | 3 | CB | ILE | 1 | 11.788 | −0.143 | −3.278 | 1.00 | 0.00 |
| ATOM | 4 | HB | ILE | 1 | 10.810 | 0.216 | −3.564 | 1.00 | 0.00 |
| ATOM | 5 | CG1 | ILE | 1 | 12.034 | −1.514 | −3.911 | 1.00 | 0.00 |
| ATOM | 6 | HG11 | ILE | 1 | 12.789 | −2.041 | −3.347 | 1.00 | 0.00 |
| ATOM | 7 | HG12 | ILE | 1 | 12.368 | −1.385 | −4.930 | 1.00 | 0.00 |
| ATOM | 8 | CG2 | ILE | 1 | 12.852 | 0.841 | −3.766 | 1.00 | 0.00 |
| ATOM | 9 | HG21 | ILE | 1 | 13.794 | 0.326 | −3.880 | 1.00 | 0.00 |
| ATOM | 10 | HG22 | ILE | 1 | 12.963 | 1.638 | −3.045 | 1.00 | 0.00 |
| ATOM | 11 | HG23 | ILE | 1 | 12.551 | 1.256 | −4.717 | 1.00 | 0.00 |
| ATOM | 12 | CD1 | ILE | 1 | 10.735 | −2.319 | −3.895 | 1.00 | 0.00 |
| ATOM | 13 | HD11 | ILE | 1 | 10.871 | −3.209 | −3.300 | 1.00 | 0.00 |
| ATOM | 14 | HD12 | ILE | 1 | 10.472 | −2.596 | −4.905 | 1.00 | 0.00 |
| ATOM | 15 | HD13 | ILE | 1 | 9.945 | −1.718 | −3.469 | 1.00 | 0.00 |
| ATOM | 16 | C | ILE | 1 | 10.762 | −1.195 | −1.232 | 1.00 | 0.00 |
| ATOM | 17 | O | ILE | 1 | 10.856 | −2.402 | −1.334 | 1.00 | 0.00 |
| ATOM | 18 | N | ILE | 1 | 13.205 | −0.849 | −1.475 | 1.00 | 0.00 |
| ATOM | 19 | HT1 | ILE | 1 | 13.115 | −1.875 | −1.335 | 1.00 | 0.00 |
| ATOM | 20 | HT2 | ILE | 1 | 13.599 | −0.414 | −0.615 | 1.00 | 0.00 |
| ATOM | 21 | HT3 | ILE | 1 | 13.839 | −0.665 | −2.278 | 1.00 | 0.00 |
| ATOM | 22 | N | LEU | 2 | 9.722 | −0.643 | −0.667 | 1.00 | 0.00 |
| ATOM | 23 | HN | LEU | 2 | 9.666 | 0.337 | −0.591 | 1.00 | 0.00 |
| ATOM | 24 | CA | LEU | 2 | 8.619 | −1.500 | −0.136 | 1.00 | 0.00 |
| ATOM | 25 | HA | LEU | 2 | 8.809 | −2.544 | −0.349 | 1.00 | 0.00 |
| ATOM | 26 | CB | LEU | 2 | 8.630 | −1.265 | 1.375 | 1.00 | 0.00 |
| ATOM | 27 | HB1 | LEU | 2 | 7.626 | −1.058 | 1.714 | 1.00 | 0.00 |
| ATOM | 28 | HB2 | LEU | 2 | 9.269 | −0.424 | 1.604 | 1.00 | 0.00 |
| ATOM | 29 | CG | LEU | 2 | 9.156 | −2.514 | 2.083 | 1.00 | 0.00 |
| ATOM | 30 | HG | LEU | 2 | 9.725 | −3.111 | 1.384 | 1.00 | 0.00 |
| ATOM | 31 | CD1 | LEU | 2 | 10.056 | −2.100 | 3.249 | 1.00 | 0.00 |
| ATOM | 32 | HD11 | LEU | 2 | 11.090 | −2.148 | 2.940 | 1.00 | 0.00 |
| ATOM | 33 | HD12 | LEU | 2 | 9.897 | −2.770 | 4.081 | 1.00 | 0.00 |
| ATOM | 34 | HD13 | LEU | 2 | 9.816 | −1.091 | 3.548 | 1.00 | 0.00 |
| ATOM | 35 | CD2 | LEU | 2 | 7.977 | −3.332 | 2.615 | 1.00 | 0.00 |
| ATOM | 36 | HD21 | LEU | 2 | 7.730 | −3.000 | 3.613 | 1.00 | 0.00 |
| ATOM | 37 | HD22 | LEU | 2 | 8.246 | −4.378 | 2.640 | 1.00 | 0.00 |
| ATOM | 38 | HD23 | LEU | 2 | 7.123 | −3.195 | 1.968 | 1.00 | 0.00 |
| ATOM | 39 | C | LEU | 2 | 7.279 | −1.067 | −0.736 | 1.00 | 0.00 |
| ATOM | 40 | O | LEU | 2 | 7.213 | −0.161 | −1.544 | 1.00 | 0.00 |
| ATOM | 41 | N | SER | 3 | 6.209 | −1.707 | −0.349 | 1.00 | 0.00 |
| ATOM | 42 | HN | SER | 3 | 6.283 | −2.435 | 0.304 | 1.00 | 0.00 |
| ATOM | 43 | CA | SER | 3 | 4.875 | −1.331 | −0.898 | 1.00 | 0.00 |
| ATOM | 44 | HA | SER | 3 | 4.861 | −0.288 | −1.173 | 1.00 | 0.00 |
| ATOM | 45 | CB | SER | 3 | 4.700 | −2.201 | −2.142 | 1.00 | 0.00 |
| ATOM | 46 | HB1 | SER | 3 | 5.077 | −1.671 | −3.007 | 1.00 | 0.00 |
| ATOM | 47 | HB2 | SER | 3 | 3.655 | −2.421 | −2.286 | 1.00 | 0.00 |
| ATOM | 48 | OG | SER | 3 | 5.414 | −3.418 | −1.967 | 1.00 | 0.00 |
| ATOM | 49 | HG | SER | 3 | 4.796 | −4.082 | −1.654 | 1.00 | 0.00 |
| ATOM | 50 | C | SER | 3 | 3.777 | −1.630 | 0.126 | 1.00 | 0.00 |
| ATOM | 51 | O | SER | 3 | 3.504 | −2.771 | 0.442 | 1.00 | 0.00 |
| ATOM | 52 | N | ARG | 4 | 3.145 | −0.613 | 0.646 | 1.00 | 0.00 |
| ATOM | 53 | HN | ARG | 4 | 3.380 | 0.300 | 0.375 | 1.00 | 0.00 |
| ATOM | 54 | CA | ARG | 4 | 2.063 | −0.839 | 1.649 | 1.00 | 0.00 |
| ATOM | 55 | HA | ARG | 4 | 1.545 | −1.766 | 1.443 | 1.00 | 0.00 |
| ATOM | 56 | CB | ARG | 4 | 2.784 | −0.921 | 3.001 | 1.00 | 0.00 |
| ATOM | 57 | HB1 | ARG | 4 | 2.113 | −0.610 | 3.789 | 1.00 | 0.00 |
| ATOM | 58 | HB2 | ARG | 4 | 3.648 | −0.270 | 2.990 | 1.00 | 0.00 |

TABLE 2-continued

| | | | | | | | | |
|---|---|---|---|---|---|---|---|---|
| ATOM | 59 | CG | ARG | 4 | 3.234 | −2.362 | 3.257 | 1.00 | 0.00 |
| ATOM | 60 | HG1 | ARG | 4 | 4.312 | −2.395 | 3.326 | 1.00 | 0.00 |
| ATOM | 61 | HG2 | ARG | 4 | 2.906 | −2.991 | 2.444 | 1.00 | 0.00 |
| ATOM | 62 | CD | ARG | 4 | 2.627 | −2.865 | 4.571 | 1.00 | 0.00 |
| ATOM | 63 | HD1 | ARG | 4 | 1.720 | −2.327 | 4.798 | 1.00 | 0.00 |
| ATOM | 64 | HD2 | ARG | 4 | 3.341 | −2.763 | 5.378 | 1.00 | 0.00 |
| ATOM | 65 | NE | ARG | 4 | 2.321 | −4.302 | 4.326 | 1.00 | 0.00 |
| ATOM | 66 | HE | ARG | 4 | 1.389 | −4.605 | 4.292 | 1.00 | 0.00 |
| ATOM | 67 | CZ | ARG | 4 | 3.292 | −5.157 | 4.155 | 1.00 | 0.00 |
| ATOM | 68 | NH1 | ARG | 4 | 4.516 | −4.825 | 4.463 | 1.00 | 0.00 |
| ATOM | 69 | HH11 | ARG | 4 | 4.710 | −3.915 | 4.830 | 1.00 | 0.00 |
| ATOM | 70 | HH12 | ARG | 4 | 5.259 | −5.481 | 4.333 | 1.00 | 0.00 |
| ATOM | 71 | NH2 | ARG | 4 | 3.038 | −6.344 | 3.677 | 1.00 | 0.00 |
| ATOM | 72 | HH21 | ARG | 4 | 2.100 | −6.599 | 3.441 | 1.00 | 0.00 |
| ATOM | 73 | HH22 | ARG | 4 | 3.782 | −7.000 | 3.546 | 1.00 | 0.00 |
| ATOM | 74 | C | ARG | 4 | 1.081 | 0.336 | 1.636 | 1.00 | 0.00 |
| ATOM | 75 | O | ARG | 4 | 1.468 | 1.482 | 1.752 | 1.00 | 0.00 |
| ATOM | 76 | N | ARG | 5 | −0.187 | 0.062 | 1.495 | 1.00 | 0.00 |
| ATOM | 77 | HN | ARG | 5 | −0.480 | −0.873 | 1.402 | 1.00 | 0.00 |
| ATOM | 78 | CA | ARG | 5 | −1.192 | 1.168 | 1.475 | 1.00 | 0.00 |
| ATOM | 79 | HA | ARG | 5 | −0.705 | 2.127 | 1.595 | 1.00 | 0.00 |
| ATOM | 80 | CB | ARG | 5 | −1.844 | 1.083 | 0.094 | 1.00 | 0.00 |
| ATOM | 81 | HB1 | ARG | 5 | −2.917 | 1.041 | 0.204 | 1.00 | 0.00 |
| ATOM | 82 | HB2 | ARG | 5 | −1.499 | 0.192 | −0.412 | 1.00 | 0.00 |
| ATOM | 83 | CG | ARG | 5 | −1.465 | 2.316 | −0.727 | 1.00 | 0.00 |
| ATOM | 84 | HG1 | ARG | 5 | −0.748 | 2.908 | −0.179 | 1.00 | 0.00 |
| ATOM | 85 | HG2 | ARG | 5 | −2.350 | 2.907 | −0.918 | 1.00 | 0.00 |
| ATOM | 86 | CD | ARG | 5 | −0.848 | 1.876 | −2.057 | 1.00 | 0.00 |
| ATOM | 87 | HD1 | ARG | 5 | −0.300 | 0.955 | −1.931 | 1.00 | 0.00 |
| ATOM | 88 | HD2 | ARG | 5 | −0.202 | 2.651 | −2.445 | 1.00 | 0.00 |
| ATOM | 89 | NE | ARG | 5 | −2.008 | 1.659 | −2.965 | 1.00 | 0.00 |
| ATOM | 90 | HE | ARG | 5 | −2.795 | 2.241 | −2.903 | 1.00 | 0.00 |
| ATOM | 91 | CZ | ARG | 5 | −1.977 | 0.695 | −3.845 | 1.00 | 0.00 |
| ATOM | 92 | NH1 | ARG | 5 | −0.857 | 0.392 | −4.441 | 1.00 | 0.00 |
| ATOM | 93 | HH11 | ARG | 5 | −0.022 | 0.898 | −4.225 | 1.00 | 0.00 |
| ATOM | 94 | HH12 | ARG | 5 | −0.834 | −0.347 | −5.115 | 1.00 | 0.00 |
| ATOM | 95 | NH2 | ARG | 5 | −3.067 | 0.035 | −4.127 | 1.00 | 0.00 |
| ATOM | 96 | HH21 | ARG | 5 | −3.925 | 0.267 | −3.670 | 1.00 | 0.00 |
| ATOM | 97 | HH22 | ARG | 5 | −3.043 | −0.704 | −4.801 | 1.00 | 0.00 |
| ATOM | 98 | C | ARG | 5 | −2.236 | 0.954 | 2.575 | 1.00 | 0.00 |
| ATOM | 99 | O | ARG | 5 | −2.260 | −0.078 | 3.214 | 1.00 | 0.00 |
| ATOM | 100 | N | PRO | 6 | −3.068 | 1.946 | 2.758 | 1.00 | 0.00 |
| ATOM | 101 | CA | PRO | 6 | −4.149 | 1.876 | 3.807 | 1.00 | 0.00 |
| ATOM | 102 | HA | PRO | 6 | −3.740 | 1.628 | 4.790 | 1.00 | 0.00 |
| ATOM | 103 | CB | PRO | 6 | −4.710 | 3.304 | 3.802 | 1.00 | 0.00 |
| ATOM | 104 | HB1 | PRO | 6 | −4.213 | 3.918 | 4.537 | 1.00 | 0.00 |
| ATOM | 105 | HB2 | PRO | 6 | −5.780 | 3.296 | 3.976 | 1.00 | 0.00 |
| ATOM | 106 | CG | PRO | 6 | −4.411 | 3.814 | 2.426 | 1.00 | 0.00 |
| ATOM | 107 | HG1 | PRO | 6 | −4.357 | 4.887 | 2.428 | 1.00 | 0.00 |
| ATOM | 108 | HG2 | PRO | 6 | −5.177 | 3.477 | 1.740 | 1.00 | 0.00 |
| ATOM | 109 | CD | PRO | 6 | −3.087 | 3.236 | 2.027 | 1.00 | 0.00 |
| ATOM | 110 | HD2 | PRO | 6 | −3.044 | 3.093 | 0.948 | 1.00 | 0.00 |
| ATOM | 111 | HD1 | PRO | 6 | −2.275 | 3.877 | 2.353 | 1.00 | 0.00 |
| ATOM | 112 | C | PRO | 6 | −5.282 | 0.893 | 3.432 | 1.00 | 0.00 |
| ATOM | 113 | O | PRO | 6 | −6.393 | 1.035 | 3.902 | 1.00 | 0.00 |
| ATOM | 114 | N | SER | 7 | −5.030 | −0.093 | 2.607 | 1.00 | 0.00 |
| ATOM | 115 | HN | SER | 7 | −4.145 | −0.207 | 2.235 | 1.00 | 0.00 |
| ATOM | 116 | CA | SER | 7 | −6.110 | −1.051 | 2.233 | 1.00 | 0.00 |
| ATOM | 117 | HA | SER | 7 | −5.833 | −1.603 | 1.348 | 1.00 | 0.00 |
| ATOM | 118 | CB | SER | 7 | −6.238 | −2.001 | 3.415 | 1.00 | 0.00 |
| ATOM | 119 | HB1 | SER | 7 | −6.552 | −2.972 | 3.057 | 1.00 | 0.00 |
| ATOM | 120 | HB2 | SER | 7 | −6.974 | −1.619 | 4.102 | 1.00 | 0.00 |
| ATOM | 121 | OG | SER | 7 | −4.984 | −2.104 | 4.077 | 1.00 | 0.00 |
| ATOM | 122 | HG | SER | 7 | −5.045 | −2.814 | 4.720 | 1.00 | 0.00 |
| ATOM | 123 | C | SER | 7 | −7.430 | −0.316 | 2.010 | 1.00 | 0.00 |
| ATOM | 124 | O | SER | 7 | −8.251 | −0.211 | 2.899 | 1.00 | 0.00 |
| ATOM | 125 | N | TYR | 8 | −7.643 | 0.184 | 0.831 | 1.00 | 0.00 |
| ATOM | 126 | HN | TYR | 8 | −6.966 | 0.078 | 0.127 | 1.00 | 0.00 |
| ATOM | 127 | CA | TYR | 8 | −8.925 | 0.904 | 0.559 | 1.00 | 0.00 |
| ATOM | 128 | HA | TYR | 8 | −9.535 | 0.924 | 1.451 | 1.00 | 0.00 |
| ATOM | 129 | CB | TYR | 8 | −8.533 | 2.329 | 0.179 | 1.00 | 0.00 |
| ATOM | 130 | HB1 | TYR | 8 | −9.278 | 2.738 | −0.498 | 1.00 | 0.00 |
| ATOM | 131 | HB2 | TYR | 8 | −7.570 | 2.317 | −0.324 | 1.00 | 0.00 |
| ATOM | 132 | CG | TYR | 8 | −8.466 | 3.172 | 1.458 | 1.00 | 0.00 |
| ATOM | 133 | CD1 | TYR | 8 | −7.422 | 4.091 | 1.648 | 1.00 | 0.00 |
| ATOM | 134 | HD1 | TYR | 8 | −6.664 | 4.205 | 0.901 | 1.00 | 0.00 |
| ATOM | 135 | CD2 | TYR | 8 | −9.451 | 3.035 | 2.465 | 1.00 | 0.00 |
| ATOM | 136 | HD2 | TYR | 8 | −10.261 | 2.331 | 2.352 | 1.00 | 0.00 |
| ATOM | 137 | CE1 | TYR | 8 | −7.360 | 4.861 | 2.815 | 1.00 | 0.00 |
| ATOM | 138 | HE1 | TYR | 8 | −6.553 | 5.566 | 2.952 | 1.00 | 0.00 |

TABLE 2-continued

| | | | | | | | | | |
|---|---|---|---|---|---|---|---|---|---|
| ATOM | 139 | CE2 | TYR | 8 | −9.379 | 3.809 | 3.629 | 1.00 | 0.00 |
| ATOM | 140 | HE2 | TYR | 8 | −10.134 | 3.702 | 4.394 | 1.00 | 0.00 |
| ATOM | 141 | CZ | TYR | 8 | −8.336 | 4.721 | 3.803 | 1.00 | 0.00 |
| ATOM | 142 | OH | TYR | 8 | −8.270 | 5.483 | 4.951 | 1.00 | 0.00 |
| ATOM | 143 | HH | TYR | 8 | −7.345 | 5.662 | 5.136 | 1.00 | 0.00 |
| ATOM | 144 | C | TYR | 8 | −9.680 | 0.230 | −0.587 | 1.00 | 0.00 |
| ATOM | 145 | O | TYR | 8 | −9.400 | 0.456 | −1.747 | 1.00 | 0.00 |
| ATOM | 146 | N | ARG | 9 | −10.639 | −0.592 | −0.266 | 1.00 | 0.00 |
| ATOM | 147 | HN | ARG | 9 | −10.848 | −0.751 | 0.681 | 1.00 | 0.00 |
| ATOM | 148 | CA | ARG | 9 | −11.423 | −1.283 | −1.334 | 1.00 | 0.00 |
| ATOM | 149 | HA | ARG | 9 | −11.870 | −0.561 | −1.999 | 1.00 | 0.00 |
| ATOM | 150 | CB | ARG | 9 | −10.408 | −2.140 | −2.099 | 1.00 | 0.00 |
| ATOM | 151 | HB1 | ARG | 9 | −9.528 | −1.554 | −2.314 | 1.00 | 0.00 |
| ATOM | 152 | HB2 | ARG | 9 | −10.849 | −2.477 | −3.027 | 1.00 | 0.00 |
| ATOM | 153 | CG | ARG | 9 | −10.015 | −3.354 | −1.253 | 1.00 | 0.00 |
| ATOM | 154 | HG1 | ARG | 9 | −10.141 | −3.120 | −0.206 | 1.00 | 0.00 |
| ATOM | 155 | HG2 | ARG | 9 | −8.982 | −3.606 | −1.444 | 1.00 | 0.00 |
| ATOM | 156 | CD | ARG | 9 | −10.907 | −4.543 | −1.618 | 1.00 | 0.00 |
| ATOM | 157 | HD1 | ARG | 9 | −11.932 | −4.342 | −1.351 | 1.00 | 0.00 |
| ATOM | 158 | HD2 | ARG | 9 | −10.556 | −5.439 | −1.125 | 1.00 | 0.00 |
| ATOM | 159 | NE | ARG | 9 | −10.781 | −4.677 | −3.096 | 1.00 | 0.00 |
| ATOM | 160 | HE | ARG | 9 | −11.439 | −4.252 | −3.684 | 1.00 | 0.00 |
| ATOM | 161 | CZ | ARG | 9 | −9.794 | −5.361 | −3.607 | 1.00 | 0.00 |
| ATOM | 162 | NH1 | ARG | 9 | −8.770 | −5.684 | −2.865 | 1.00 | 0.00 |
| ATOM | 163 | HH11 | ARG | 9 | −8.742 | −5.408 | −1.904 | 1.00 | 0.00 |
| ATOM | 164 | HH12 | ARG | 9 | −8.014 | −6.208 | −3.256 | 1.00 | 0.00 |
| ATOM | 165 | NH2 | ARG | 9 | −9.831 | −5.723 | −4.860 | 1.00 | 0.00 |
| ATOM | 166 | HH21 | ARG | 9 | −10.615 | −5.476 | −5.429 | 1.00 | 0.00 |
| ATOM | 167 | HH22 | ARG | 9 | −9.074 | −6.247 | −5.252 | 1.00 | 0.00 |
| ATOM | 168 | C | ARG | 9 | −12.504 | −2.167 | −0.705 | 1.00 | 0.00 |
| ATOM | 169 | OT1 | ARG | 9 | −13.492 | −2.425 | −1.372 | 1.00 | 0.00 |
| ATOM | 170 | OT2 | ARG | 9 | −12.324 | −2.570 | 0.433 | 1.00 | 0.00 |
| END | | | | | | | | | |

TABLE 3

REMARK FILENAME = "refine_1_20.pdb"
REMARK
===================================================
REMARK overall, bonds, angles, improper, vdw, noe, cdih
REMARK energies: 104.733, 3.47295, 70.7767, 3.51384, 6.64866,
20.3204, $CDIH
REMARK
===================================================
REMARK bonds, angles, impropers, noe, cdih
REMARK rms-d: 4.442149E−03, 1.21652, 0.496579, 7.90724E−02, 0
REMARK
===================================================
REMARK        noe, cdih
REMARK violations.: 0, 0
REMARK
===================================================
REMARK DATE: 03 Apr. 2000 08:41:00        created by user: orish

| | | | | | | | | | |
|---|---|---|---|---|---|---|---|---|---|
| ATOM | 1 | CA | ILE | 1B | −9.783 | −1.457 | −0.558 | 1.00 | 0.00 |
| ATOM | 2 | HA | ILE | 1B | −9.677 | −0.665 | −1.298 | 1.00 | 0.00 |
| ATOM | 3 | CB | ILE | 1B | −11.259 | −1.637 | −0.199 | 1.00 | 0.00 |
| ATOM | 4 | HB | ILE | 1B | −11.578 | −0.796 | 0.417 | 1.00 | 0.00 |
| ATOM | 5 | CG1 | ILE | 1B | −11.441 | −2.945 | 0.598 | 1.00 | 0.00 |
| ATOM | 6 | HG11 | ILE | 1B | −12.251 | −2.816 | 1.316 | 1.00 | 0.00 |
| ATOM | 7 | HG12 | ILE | 1B | −10.519 | −3.167 | 1.135 | 1.00 | 0.00 |
| ATOM | 8 | CG2 | ILE | 1B | −12.101 | −1.660 | −1.481 | 1.00 | 0.00 |
| ATOM | 9 | HG21 | ILE | 1B | −12.492 | −0.662 | −1.677 | 1.00 | 0.00 |
| ATOM | 10 | HG22 | ILE | 1B | −12.930 | −2.357 | −1.358 | 1.00 | 0.00 |
| ATOM | 11 | HG23 | ILE | 1B | −11.480 | −1.978 | −2.318 | 1.00 | 0.00 |
| ATOM | 12 | CD1 | ILE | 1B | −11.776 | −4.119 | −0.334 | 1.00 | 0.00 |
| ATOM | 13 | HD11 | ILE | 1B | −11.998 | −5.004 | 0.263 | 1.00 | 0.00 |
| ATOM | 14 | HD12 | ILE | 1B | −10.926 | −4.325 | −0.983 | 1.00 | 0.00 |
| ATOM | 15 | HD13 | ILE | 1B | −12.644 | −3.866 | −0.941 | 1.00 | 0.00 |
| ATOM | 16 | C | ILE | 1B | −8.973 | −1.137 | 0.677 | 1.00 | 0.00 |
| ATOM | 17 | O | ILE | 1B | −9.510 | −0.787 | 1.709 | 1.00 | 0.00 |
| ATOM | 18 | N | ILE | 1B | −9.351 | −2.764 | −1.130 | 1.00 | 0.00 |
| ATOM | 19 | HT1 | ILE | 1B | −8.379 | −2.681 | −1.489 | 1.00 | 0.00 |
| ATOM | 20 | HT2 | ILE | 1B | −9.987 | −3.028 | −1.910 | 1.00 | 0.00 |
| ATOM | 21 | HT3 | ILE | 1B | −9.383 | −3.494 | −0.391 | 1.00 | 0.00 |
| ATOM | 22 | N | LEU | 2 | −7.676 | −1.250 | 0.593 | 1.00 | 0.00 |
| ATOM | 23 | HN | LEU | 2 | −7.221 | −1.531 | −0.230 | 1.00 | 0.00 |
| ATOM | 24 | CA | LEU | 2 | −6.745 | −0.970 | 1.725 | 1.00 | 0.00 |

TABLE 3-continued

| | | | | | | | | | |
|---|---|---|---|---|---|---|---|---|---|
| ATOM | 25 | HA | LEU | 2 | −7.286 | −0.659 | 2.617 | 1.00 | 0.00 |
| ATOM | 26 | CB | LEU | 2 | −6.051 | −2.305 | 1.992 | 1.00 | 0.00 |
| ATOM | 27 | HB1 | LEU | 2 | −5.606 | −2.675 | 1.069 | 1.00 | 0.00 |
| ATOM | 28 | HB2 | LEU | 2 | −6.782 | −3.027 | 2.359 | 1.00 | 0.00 |
| ATOM | 29 | CG | LEU | 2 | −4.955 | −2.110 | 3.041 | 1.00 | 0.00 |
| ATOM | 30 | HG | LEU | 2 | −5.142 | −1.190 | 3.595 | 1.00 | 0.00 |
| ATOM | 31 | GD1 | LEU | 2 | −4.955 | −3.296 | 4.007 | 1.00 | 0.00 |
| ATOM | 32 | HD11 | LEU | 2 | −5.261 | −2.958 | 4.997 | 1.00 | 0.00 |
| ATOM | 33 | HD12 | LEU | 2 | −3.952 | −3.720 | 4.062 | 1.00 | 0.00 |
| ATOM | 34 | HD13 | LEU | 2 | −5.651 | −4.055 | 3.651 | 1.00 | 0.00 |
| ATOM | 35 | CD2 | LEU | 2 | −3.595 | −2.020 | 2.345 | 1.00 | 0.00 |
| ATOM | 36 | HD21 | LEU | 2 | −3.732 | −1.671 | 1.322 | 1.00 | 0.00 |
| ATOM | 37 | HD22 | LEU | 2 | −3.127 | −3.004 | 2.334 | 1.00 | 0.00 |
| ATOM | 38 | HD23 | LEU | 2 | −2.956 | −1.320 | 2.884 | 1.00 | 0.00 |
| ATOM | 39 | C | LEU | 2 | −5.725 | 0.080 | 1.347 | 1.00 | 0.00 |
| ATOM | 40 | O | LEU | 2 | −4.915 | 0.491 | 2.155 | 1.00 | 0.00 |
| ATOM | 41 | N | SER | 3 | −5.747 | 0.528 | 0.122 | 1.00 | 0.00 |
| ATOM | 42 | HN | SER | 3 | −6.390 | 0.212 | −0.547 | 1.00 | 0.00 |
| ATOM | 43 | CA | SER | 3 | −4.806 | 1.562 | −0.398 | 1.00 | 0.00 |
| ATOM | 44 | HA | SER | 3 | −4.771 | 1.557 | −1.486 | 1.00 | 0.00 |
| ATOM | 45 | CB | SER | 3 | −5.388 | 2.889 | 0.083 | 1.00 | 0.00 |
| ATOM | 46 | HB1 | SER | 3 | −6.272 | 3.133 | −0.510 | 1.00 | 0.00 |
| ATOM | 47 | HB2 | SER | 3 | −4.648 | 3.677 | −0.034 | 1.00 | 0.00 |
| ATOM | 48 | OG | SER | 3 | −5.738 | 2.778 | 1.457 | 1.00 | 0.00 |
| ATOM | 49 | HG | SER | 3 | −6.250 | 3.554 | 1.696 | 1.00 | 0.00 |
| ATOM | 50 | C | SER | 3 | −3.416 | 1.369 | 0.164 | 1.00 | 0.00 |
| ATOM | 51 | O | SER | 3 | −3.131 | 1.747 | 1.283 | 1.00 | 0.00 |
| ATOM | 52 | N | ARG | 4 | −2.534 | 0.782 | −0.597 | 1.00 | 0.00 |
| ATOM | 53 | HN | ARG | 4 | −2.747 | 0.466 | −1.515 | 1.00 | 0.00 |
| ATOM | 54 | CA | ARG | 4 | −1.116 | 0.522 | −0.175 | 1.00 | 0.00 |
| ATOM | 55 | HA | ARG | 4 | −0.840 | 1.104 | 0.716 | 1.00 | 0.00 |
| ATOM | 56 | CB | ARG | 4 | −1.095 | −0.975 | 0.176 | 1.00 | 0.00 |
| ATOM | 57 | HB1 | ARG | 4 | −1.739 | −1.526 | −0.506 | 1.00 | 0.00 |
| ATOM | 58 | HB2 | ARG | 4 | −1.453 | −1.114 | 1.200 | 1.00 | 0.00 |
| ATOM | 59 | CG | ARG | 4 | 0.323 | −1.521 | 0.077 | 1.00 | 0.00 |
| ATOM | 60 | HG1 | ARG | 4 | 1.018 | −0.714 | −0.142 | 1.00 | 0.00 |
| ATOM | 61 | HG2 | ARG | 4 | 0.369 | −2.273 | −0.711 | 1.00 | 0.00 |
| ATOM | 62 | CD | ARG | 4 | 0.681 | −2.146 | 1.415 | 1.00 | 0.00 |
| ATOM | 63 | HD1 | ARG | 4 | −0.203 | −2.604 | 1.849 | 1.00 | 0.00 |
| ATOM | 64 | HD2 | ARG | 4 | 1.067 | −1.373 | 2.079 | 1.00 | 0.00 |
| ATOM | 65 | NE | ARG | 4 | 1.715 | −3.169 | 1.096 | 1.00 | 0.00 |
| ATOM | 66 | HE | ARG | 4 | 2.519 | −3.100 | 1.652 | 1.00 | 0.00 |
| ATOM | 67 | CZ | ARG | 4 | 1.576 | −4.075 | 0.168 | 1.00 | 0.00 |
| ATOM | 68 | NH1 | ARG | 4 | 1.048 | −5.233 | 0.460 | 1.00 | 0.00 |
| ATOM | 69 | HH11 | ARG | 4 | 0.750 | −5.424 | 1.395 | 1.00 | 0.00 |
| ATOM | 70 | HH12 | ARG | 4 | 0.942 | −5.927 | −0.252 | 1.00 | 0.00 |
| ATOM | 71 | NH2 | ARG | 4 | 1.965 | −3.825 | −1.052 | 1.00 | 0.00 |
| ATOM | 72 | HH21 | ARG | 4 | 2.370 | −2.938 | −1.276 | 1.00 | 0.00 |
| ATOM | 73 | HH22 | ARG | 4 | 1.859 | −4.520 | −1.764 | 1.00 | 0.00 |
| ATOM | 74 | C | ARG | 4 | −0.156 | 0.835 | −1.306 | 1.00 | 0.00 |
| ATOM | 75 | O | ARG | 4 | 0.292 | −0.044 | −2.015 | 1.00 | 0.00 |
| ATOM | 76 | N | ARG | 5 | 0.150 | 2.088 | −1.507 | 1.00 | 0.00 |
| ATOM | 77 | HN | ARG | 5 | −0.225 | 2.805 | −0.970 | 1.00 | 0.00 |
| ATOM | 78 | CA | ARG | 5 | 1.062 | 2.546 | −2.605 | 1.00 | 0.00 |
| ATOM | 79 | HA | ARG | 5 | 1.447 | 1.693 | −3.157 | 1.00 | 0.00 |
| ATOM | 80 | CB | ARG | 5 | 0.167 | 3.349 | −3.540 | 1.00 | 0.00 |
| ATOM | 81 | HB1 | ARG | 5 | 0.684 | 3.496 | −4.489 | 1.00 | 0.00 |
| ATOM | 82 | HB2 | ARG | 5 | −0.044 | 4.319 | −3.089 | 1.00 | 0.00 |
| ATOM | 83 | CG | ARG | 5 | −1.142 | 2.596 | −3.784 | 1.00 | 0.00 |
| ATOM | 84 | HG1 | ARG | 5 | −1.832 | 3.235 | −4.334 | 1.00 | 0.00 |
| ATOM | 85 | HG2 | ARG | 5 | −1.587 | 2.319 | −2.828 | 1.00 | 0.00 |
| ATOM | 86 | CD | ARG | 5 | −0.861 | 1.333 | −4.602 | 1.00 | 0.00 |
| ATOM | 87 | HD1 | ARG | 5 | −1.790 | 0.801 | −4.798 | 1.00 | 0.00 |
| ATOM | 88 | HD2 | ARG | 5 | −0.168 | 0.687 | −4.058 | 1.00 | 0.00 |
| ATOM | 89 | NE | ARG | 5 | −0.259 | 1.834 | −5.868 | 1.00 | 0.00 |
| ATOM | 90 | HE | ARG | 5 | 0.592 | 1.404 | −6.094 | 1.00 | 0.00 |
| ATOM | 91 | CZ | ARG | 5 | −0.804 | 2.756 | −6.613 | 1.00 | 0.00 |
| ATOM | 92 | NH1 | ARG | 5 | −2.099 | 2.919 | −6.607 | 1.00 | 0.00 |
| ATOM | 93 | HH11 | ARG | 5 | −2.673 | 2.338 | −6.031 | 1.00 | 0.00 |
| ATOM | 94 | HH12 | ARG | 5 | −2.516 | 3.626 | −7.178 | 1.00 | 0.00 |
| ATOM | 95 | NH2 | ARG | 5 | −0.054 | 3.515 | −7.365 | 1.00 | 0.00 |
| ATOM | 96 | HH21 | ARG | 5 | 0.938 | 3.389 | −7.370 | 1.00 | 0.00 |
| ATOM | 97 | HH22 | ARG | 5 | −0.472 | 4.221 | −7.936 | 1.00 | 0.00 |
| ATOM | 98 | C | ARG | 5 | 2.235 | 3.432 | −2.176 | 1.00 | 0.00 |
| ATOM | 99 | O | ARG | 5 | 3.149 | 3.598 | −2.959 | 1.00 | 0.00 |
| ATOM | 100 | N | PRO | 6 | 2.225 | 4.009 | −0.990 | 1.00 | 0.00 |
| ATOM | 101 | CA | PRO | 6 | 3.362 | 4.885 | −0.604 | 1.00 | 0.00 |
| ATOM | 102 | HA | PRO | 6 | 3.562 | 5.623 | −1.380 | 1.00 | 0.00 |
| ATOM | 103 | CB | PRO | 6 | 2.877 | 5.579 | 0.665 | 1.00 | 0.00 |
| ATOM | 104 | HB1 | PRO | 6 | 2.405 | 6.534 | 0.423 | 1.00 | 0.00 |

TABLE 3-continued

| | | | | | | | | |
|---|---|---|---|---|---|---|---|---|
| ATOM | 105 | HB2 | PRO | 6 | 3.704 | 5.730 | 1.362 | 1.00 | 0.00 |
| ATOM | 106 | CG | PRO | 6 | 1.867 | 4.642 | 1.236 | 1.00 | 0.00 |
| ATOM | 107 | HG1 | PRO | 6 | 1.119 | 5.192 | 1.780 | 1.00 | 0.00 |
| ATOM | 108 | HG2 | PRO | 6 | 2.357 | 3.932 | 1.887 | 1.00 | 0.00 |
| ATOM | 109 | CD | PRO | 6 | 1.228 | 3.922 | 0.080 | 1.00 | 0.00 |
| ATOM | 110 | HD2 | PRO | 6 | 1.038 | 2.890 | 0.343 | 1.00 | 0.00 |
| ATOM | 111 | HD1 | PRO | 6 | 0.316 | 4.415 | −0.219 | 1.00 | 0.00 |
| ATOM | 112 | C | PRO | 6 | 4.587 | 4.040 | −0.334 | 1.00 | 0.00 |
| ATOM | 113 | O | PRO | 6 | 5.195 | 4.120 | 0.714 | 1.00 | 0.00 |
| ATOM | 114 | N | SRP | 7 | 4.973 | 3.235 | −1.287 | 1.00 | 0.00 |
| ATOM | 115 | HN | SRP | 7 | 4.501 | 3.180 | −2.153 | 1.00 | 0.00 |
| ATOM | 116 | CA | SRP | 7 | 6.178 | 2.345 | −1.198 | 1.00 | 0.00 |
| ATOM | 117 | C | SRP | 7 | 5.986 | 1.217 | −0.187 | 1.00 | 0.00 |
| ATOM | 118 | O | SRP | 7 | 6.890 | 0.401 | 0.000 | 1.00 | 0.00 |
| ATOM | 119 | CB | SRP | 7 | 7.409 | 3.196 | −0.806 | 1.00 | 0.00 |
| ATOM | 120 | OG1 | SRP | 7 | 7.614 | 4.247 | −1.816 | 1.00 | 0.00 |
| ATOM | 121 | PG2 | SRP | 7 | 9.111 | 4.826 | −1.692 | 1.00 | 0.00 |
| ATOM | 122 | OG3 | SRP | 7 | 9.841 | 4.741 | −3.126 | 1.00 | 0.00 |
| ATOM | 123 | OG2 | SRP | 7 | 9.883 | 4.016 | −0.692 | 1.00 | 0.00 |
| ATOM | 124 | OG4 | SRP | 7 | 9.056 | 6.362 | −1.210 | 1.00 | 0.00 |
| ATOM | 125 | HA | SRP | 7 | 6.354 | 1.890 | −2.170 | 1.00 | 0.00 |
| ATOM | 126 | HG3 | SRP | 7 | 10.770 | 4.312 | −3.012 | 1.00 | 0.00 |
| ATOM | 127 | HG4 | SRP | 7 | 8.124 | 6.751 | −1.413 | 1.00 | 0.00 |
| ATOM | 128 | HB1 | SRP | 7 | 8.290 | 2.553 | −0.751 | 1.00 | 0.00 |
| ATOM | 129 | HB2 | SRP | 7 | 7.240 | 3.659 | 0.163 | 1.00 | 0.00 |
| ATOM | 130 | N | TYR | 8 | 4.845 | 1.147 | 0.452 | 1.00 | 0.00 |
| ATOM | 131 | HN | TYR | 8 | 4.121 | 1.772 | 0.312 | 1.00 | 0.00 |
| ATOM | 132 | CA | TYR | 8 | 4.521 | 0.098 | 1.463 | 1.00 | 0.00 |
| ATOM | 133 | HA | TYR | 8 | 4.788 | 0.421 | 2.466 | 1.00 | 0.00 |
| ATOM | 134 | CB | TYR | 8 | 3.001 | −0.061 | 1.371 | 1.00 | 0.00 |
| ATOM | 135 | HB1 | TYR | 8 | 2.757 | −1.115 | 1.255 | 1.00 | 0.00 |
| ATOM | 136 | HB2 | TYR | 8 | 2.631 | 0.495 | 0.510 | 1.00 | 0.00 |
| ATOM | 137 | CG | TYR | 8 | 2.351 | 0.471 | 2.630 | 1.00 | 0.00 |
| ATOM | 138 | CD1 | TYR | 8 | 2.895 | 0.164 | 3.884 | 1.00 | 0.00 |
| ATOM | 139 | HD1 | TYR | 8 | 3.776 | −0.453 | 3.953 | 1.00 | 0.00 |
| ATOM | 140 | CD2 | TYR | 8 | 1.202 | 1.269 | 2.544 | 1.00 | 0.00 |
| ATOM | 141 | HD2 | TYR | 8 | 0.776 | 1.504 | 1.579 | 1.00 | 0.00 |
| ATOM | 142 | CE1 | TYR | 8 | 2.293 | 0.655 | 5.048 | 1.00 | 0.00 |
| ATOM | 143 | HE1 | TYR | 8 | 2.713 | 0.417 | 6.014 | 1.00 | 0.00 |
| ATOM | 144 | CE2 | TYR | 8 | 0.600 | 1.759 | 3.710 | 1.00 | 0.00 |
| ATOM | 145 | HE2 | TYR | 8 | −0.284 | 2.374 | 3.643 | 1.00 | 0.00 |
| ATOM | 146 | CZ | TYR | 8 | 1.146 | 1.452 | 4.961 | 1.00 | 0.00 |
| ATOM | 147 | OH | TYR | 8 | 0.553 | 1.936 | 6.110 | 1.00 | 0.00 |
| ATOM | 148 | HH | TYR | 8 | 1.222 | 2.407 | 6.613 | 1.00 | 0.00 |
| ATOM | 149 | C | TYR | 8 | 5.198 | −1.217 | 1.126 | 1.00 | 0.00 |
| ATOM | 150 | O | TYR | 8 | 5.057 | −1.728 | 0.033 | 1.00 | 0.00 |
| ATOM | 151 | N | ARG | 9 | 5.936 | −1.788 | 2.046 | 1.00 | 0.00 |
| ATOM | 152 | HN | ARG | 9 | 6.065 | −1.397 | 2.951 | 1.00 | 0.00 |
| ATOM | 153 | CA | ARG | 9 | 6.655 | −3.095 | 1.832 | 1.00 | 0.00 |
| ATOM | 154 | HA | ARG | 9 | 5.958 | −3.901 | 1.569 | 1.00 | 0.00 |
| ATOM | 155 | CB | ARG | 9 | 7.597 | −2.847 | 0.639 | 1.00 | 0.00 |
| ATOM | 156 | HB1 | ARG | 9 | 7.078 | −2.256 | −0.115 | 1.00 | 0.00 |
| ATOM | 157 | HB2 | ARG | 9 | 7.886 | −3.805 | 0.204 | 1.00 | 0.00 |
| ATOM | 158 | CG | ARG | 9 | 8.858 | −2.097 | 1.089 | 1.00 | 0.00 |
| ATOM | 159 | HG1 | ARG | 9 | 8.772 | −1.825 | 2.139 | 1.00 | 0.00 |
| ATOM | 160 | HG2 | ARG | 9 | 8.975 | −1.193 | 0.489 | 1.00 | 0.00 |
| ATOM | 161 | CD | ARG | 9 | 10.085 | −2.996 | 0.895 | 1.00 | 0.00 |
| ATOM | 162 | HD1 | ARG | 9 | 10.070 | −3.810 | 1.617 | 1.00 | 0.00 |
| ATOM | 163 | HD2 | ARG | 9 | 10.998 | −2.408 | 1.013 | 1.00 | 0.00 |
| ATOM | 164 | NE | ARG | 9 | 9.950 | −3.518 | −0.493 | 1.00 | 0.00 |
| ATOM | 165 | HE | ARG | 9 | 9.658 | −4.453 | −0.534 | 1.00 | 0.00 |
| ATOM | 166 | CZ | ARG | 9 | 10.193 | −2.808 | −1.561 | 1.00 | 0.00 |
| ATOM | 167 | NH1 | ARG | 9 | 11.414 | −2.436 | −1.833 | 1.00 | 0.00 |
| ATOM | 168 | HH11 | ARG | 9 | 12.163 | −2.695 | −1.223 | 1.00 | 0.00 |
| ATOM | 169 | HH12 | ARG | 9 | 11.600 | −1.892 | −2.651 | 1.00 | 0.00 |
| ATOM | 170 | NH2 | ARG | 9 | 9.215 | −2.471 | −2.357 | 1.00 | 0.00 |
| ATOM | 171 | HH21 | ARG | 9 | 8.280 | −2.756 | −2.149 | 1.00 | 0.00 |
| ATOM | 172 | HH22 | ARG | 9 | 9.402 | −1.927 | −3.175 | 1.00 | 0.00 |
| ATOM | 173 | C | ARG | 9 | 7.449 | −3.492 | 3.057 | 1.00 | 0.00 |
| ATOM | 174 | OT1 | ARG | 9 | 7.344 | −2.801 | 4.057 | 1.00 | 0.00 |
| ATOM | 175 | OT2 | ARG | 9 | 8.155 | −4.485 | 2.985 | 1.00 | 0.00 |
| END | | | | | | | | | |

TABLE 4

| Orientation Type | Activity EC50 | E of Interaction Kcal/mole | E total Kcal/mole | Arg 96 (Å) | Arg 180 (Å) | Lys 205 (Å) | Asp 90 (Å) | Glu 97 (Å) | Asp 181 (Å) | Glu 211 (Å) | Glu 200 (Å) | Gln 89 (Å) | Phe 67 (Å) | Tyr 216 (Å) | Else ### (Å) |
|---|---|---|---|---|---|---|---|---|---|---|---|---|---|---|---|
| GSC-4 | 181 | 1.7 | −646.311 | −10317.1 | 1.82 | 2.12 | | | | 2.95 | | | | | 2.77 | Ile 217 1.97 |
| GSC-5 | 97 | >1.7 | −716.207 | −8990.75 | 1.8 | 3.34 | | | 4.47 | | | | | 2.87 | | |
| GSC-6 | 181 | | −691.37 | −9190.39 | 1.68 | 2.02 | | | 3.38 | 2.03 | | | | | 3.35 | |
| GSC-7 | 90 | | −858.297 | −9144.78 | 1.69 | 2.44 | | 3.48 | 4.92 | | | 5.16 | | 3.75 | | |
| GSC-8 | 90 | | −822.804 | −9084.56 | 2.06 | 2.63 | | 1.71 | 1.88 | | | | | 3.6 | | |
| GSC-9 (1) | 90 | | −922.065 | 9221.27 | 1.87 | 2.77 | | 3.43 | 2.38 | | | 2.12 | 2.3 | 4.07 | | |
| GSC-9 (2) | 90 | | | | 1.8 | 2.65 | | 2.41 | 2.51 | | | 1.99 | | 4.74 | | |

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES

Aberle H, Bauer A, Stappert J, Kispert A and Kemler R, "beta-catenin is a target for the ubiquitin-proteasome pathway", *EMBO J,* 16:3797-802 (1997)

American Diabetes Association, "Standards of Medical Care for Patients With Diabetes Mellitus", 21 Diabetes Care (1998).

Beasley C, Cotter D, Khan N, Pollard C, Sheppard P, Varndell I, Lovestone S, Anderton B and Everall I, "Glycogen synthase kinase-3 beta immunoreactivity is reduced in the prefrontal cortex in schizophrenia" *Neurosci Lett* 302:117-20 (2001)

Behrense J, Von Kries J P, Kuhl M, Bruhn L, Weldlich D, Grosschedl R and Birchmeier W, "Functional interaction of beta-catenin with the transcription factor LEF-1" *Nature,* 382" 638-42 (1996)

Berridge M J, Downes C P and Hanley M R, "Neural and developmental actions of lithium: a unifying hypothesis", *Cell* 59:411-419 (1989)

Bhat R V and Budd S L "GSK-3 beta signaling" casting a wide net in Alzheimer's disease" *Neurosignals* 11:251-61 (2002)

Bijur G N, De Sarno P, R S. J Glycogen synthase kinase-3 beta facilitates staurosporine- and heat shock-induced apoptosis. Protection by lithium *J Biol Chem* 275:7583-90 (2000)

Bradford M M, *Anal Biochem* 72:248-254 (1976)

Burke et al, "4'-O-[2-(2-fluoromalonyl)]-L-tyrosine: a phosphotyrosyl mimic for the preparation of signal transduction inhibitory peptides", *J Med Chem* 39(5):1021-1027 (1996a)

Burke et al, "Nonhydrolyzable phosphotyrosyl mimetics for the preparation of phosphatase-resistant SH2 domain inhibitors", *Biochemistry* 33(21):6490-6494 (1994a)

Burke et al, "Potent inhibition of insulin receptor dephosphorylation by a hexamer peptide containing the phosphotyrosyl mimetic F2Pmp", *Biochem Biophys Res Commun* 204 (1):129-133 (1994b)

Burke et al, "Small molecule interactions with protein-tyrosine phosphatase PTP1B and their use in inhibitor design", *Biochemistry* 35(50):15989-15996 (1996b)

Chen et al, "Why is phosphonodifluoromethyl phenylalanine a more potent inhibitory moiety than phosphonomethyl phenylalanine toward protein-tyrosine phosphatases?", *Biochem Biophys Res Commun* 216(3):976-984 (1995)

Chen G, Huang L D, Jiang Y M and Manji H K "The mood-stabilizing agent valproate inhibits the activity of glycogen synthase kinase-1" *J Neurochem* 72:1327-30 (1999)

Cheng K, Creacy S, Larner J Insulin-like effect of lithium ion on isolated rat adipocytes stimulation of glycogenesis beyond glucose transport. *Mol. Cell. Biochem.* 56:177-182 (1983)

Cheng, K., Creacy, S. & Larner, J. *Molecular & Cellular Biochemistry* 56, 183-9 (1983)

Cheng, K., Creacy, S. & Larner, J. *Molecular & Cellular Biochemistry* 56, 177-82 (1983)

Chu et al, "Sequential phosphorylation by mitogen-activated protein kinase and glycogen synthase kinase 3 represses transcriptional activation by heat shock factor-1", *J Biol Chem* 271(48):30847-30857 (1996)

Coghlan, M. P., Culbert, A. A., Cross, D. A., Corcoran, S. L., Yates, J. W., Pearce, N. J., Rausch, O. L., Murphy, G. J., Carter, P. S., Roxbee Cox, L., Mills, D., Brown, M. J., Haigh, D., Ward, R. W., Smith, D. G., Murray, K. J., Reith, A. D. & Holder, J. C. *Chemistry & Biology* 7, 793-803 (2000)

Cohen, P. Muscle glycogen synthase, The enzymes, edited by Boyer. P, and Krebs, E. G. (Academic Press, Orlando, Fla.) (1986)

Coyle-Rink L, Del Valle L, Sweet T, Khalili K and Amini S, "development expression of Wnt signaling factors in mouse brain" *Cancer Biol Ther* 1:640-5 (2002)

Cross D. A., Culbert A. A., Chalmers K. A., Facci L., Skaper S. D., Reith, A. D. *J Neurochem* 77:94-102 (2001).

Cross et al, "Inhibition of glycogen synthase kinase-3 by insulin mediated by protein kinase B", *Nature* 378(6559): 785-78 (1995)

Cross, D. A., Alessi, D. R., Vandenheede, J. R., McDowell, H. E., Hundal, H. S. & Cohen, P. *Biochem. J.* 303, 21-26 (1994)

Crowder R J, R S. F Glycogen synthase kinase-3 beta activity is critical for neuronal death caused by inhibiting phosphatidylinositol 3-kinase or Akt but not for death caused by nerve growth factor withdrawal. *J Biol Chem* 275:34266-71 (2000)

Dajani et al., "Crystal structure of glycogen synthase kinase 3β: structural basis for phosphate-primed substrate specificity and auto inhibition", *Cell* 105:721-732 (2001)

Damiens, E., Baratte, B., Marie, D., Eisenbrand, G. & Meijer, L. *Oncogene* 20, 3786-97 (2001)

Davies, S. P., Reddy, H., Caivano, M. & Cohen, P. *Biochemical Journal* 351, 95-105 (2000)

Devlin, *Textbook of Biochemistry with Clinical Correlations*, 4th Ed. (Wiley-Liss, Inc., 1997)

Dugas et al, *Bioorganic Chemistry* (Springer-Verlag, New York, 1981), pp 54-92

Eldar-Finkelman et al, "Expression and characterization of glycogen synthase kinase-3 mutants and their effect on glycogen synthase activity in intact cells", *Proc Natl Acad Sci USA* 93(19):10228-10233 (1996)

Eldar-Finkelman et al, "Increased glycogen synthase kinase-3 activity in diabetes- and obesity-prone C57BL/6J mice", *Diabetes* 48(8):1662-1666 (1999)

Eldar-Finkelman et al, "Phosphorylation of insulin receptor substrate 1 by glycogen synthase kinase 3 impairs insulin action", *Proc Natl Acad Sci USA* 94(18):9660-9664 (1997)

Eldar-Finkelman, H. & Krebs, E. G. *Proc. Natl. Acad. Sci.* 94, 9660-9664 (1997)

Eldar-Finkelman, H. *Trend Mol. Med.* 8, 126-132 (2002)

Eldar-Finkelman, H., Agrast, G. M., Foord, O., Fischer, E. H. & Krebs, E. G. *Proc. Natl. Acad. Sci. USA* 93, 10228-10233 (1996)

Eldar-Finkelman, H., Schreyer, S. A., Shinohara, M. M., LeBoeuf, R. C. & Krebs, E. G. *Diabetes* 48, 1662-1666 (1999)

Emoto, M., Langille, S. E. & Czech, M. P. *J. Biol. Chem.* 276, 10677-82 (2001)

Fiol et al, "A secondary phosphorylation of CREB341 at Ser129 is required for the cAMP-mediated control of gene expression. A role for glycogen synthase kinase-3 in the control of gene expression", *J Biol Chem* 269(51):32187-32193 (1994)

Fiol et al, "Formation of protein kinase recognition sites by covalent modification of the substrate. Molecular mechanism for the synergistic action of casein kinase II and glycogen synthase kinase 3", *J Biol Chem* 262(29):14042-14048 (1987)

Fiol et al, "Ordered multisite protein phosphorylation. Analysis of glycogen synthase kinase 3 action using model peptide substrates", *J Biol Chem* 265(11):6061-6065 (1990)

Fiol et al, "Phosphoserine as a recognition determinant for glycogen synthase kinase-3: phosphorylation of a synthetic peptide based on the G-component of protein phosphatase-1 *Arch Biochem Biophys* 267(2):797-802 (1988)

Fiol, C. J., Mahrenholz, A. M., Wang, Y., Roeske, R. W. & Roach, P. J. (1987) *J. Biol. Chem.* 262, 14042-8.

Fu et al, Design and synthesis of a pyridone-based phosphotyrosine mimetic", *Bioorg Med Chem Lett* 8(19):2813-2816 (1998)

Gao et al, "Inhibition of Grb2 SH2 domain binding by non-phosphate-containing ligands. 2. 4-(2-Malonyl)phenylalanine as a potent phosphotyrosyl mimetic", *J Med Chem* 43(5):911-920 (2000)

Gething et al, "Cell-surface expression of influenza haemagglutinin from a cloned DNA copy of the RNA gene *Nature* 293(5834):620-625 (1981)

Groves et al, "Structural basis for inhibition of the protein tyrosine phosphatase 1B by phosphotyrosine peptide mimetics", *Biochemistry* 37(51):17773-17783 (1998)

Hallstrom et al, "Regulation of transcription factor Pdr1p function by an Hsp70 protein in *Saccharomyces cerevisiae*", *Mol Cell Biol* 18(3):1147-1155 (1998)

Hawiger J, "Cellular import of functional peptides to block intracellular signaling *Curr Opin Immunol* 9(2):189-194 (1997)

Hawiger, J., *Current Opinion in Chem. Biol.*, 3, 89-94 (1999)

Heinemann, L., Pfutzner, A. & Heise, T. *Curr. Pharm. Des.* 14, 1327-1351 (2001)

Herbst, J. J., Andrews, G. C., Contillo, L. G., Singleton, D. H., Genereux, P. E., Gibbs, E. M. & Lienhard, G. E. *J. Biolo. Chem.* 270, 26000-5 (1995)

Hernandez F, Borrell J, Guaza C, Avila J and Lucas J J "Spatila learning deficit in transgenic mice that conditionally over-express GSK-3 beta in the brain but do not form tau filaments" *J Neurohem* 83:1529-33 (2002)

Higashimoto et al, "Human p53 is phosphorylated on serines 6 and 9 in response to DNA damage-inducing agents", *J Biol Chem* 275(30):23199-23203 (2000)

Ikeda S, Kishida S, Yamamoto H. Murai H, Koyama S and Kikuchi A "Axin, a negative regulator of the Wnt signaling pathway, forms a complex with GSK-3 beta and beta-catenin and promotes GSK-3 beta-dependent phosphorylation of beta-catenin" *EMBO J* 17:1371-84 (1998)

Jope R S and Bijur G N "Mood stabilizers, glycogen synthase kinase-3 beta and cell survival" *Molecular Psychiatry* 7(1): S35-45 (2002)

Jung, T., Kamm, W., Breitenbach, A., Kaiserling, E., Xiao, J. X. & Kissel, T. *Euro. J Pharma. Biopharma.* 50, 147-60 (2000)

Katagiri, H., Asano, T., Ishihara, H., Inukai, K., Shibasaki, Y., Kikuchi, M., Yazaki, Y. & Oka, Y. *J Biol Chem* 271, 16987-90 (1996)

Klein P S, Melton D A "A Molecular Mechanism for the Effect of Lithium on Development". *Proc. Natl. Acad. Sci. USA* 93:8455-8459 (1996).

Kole et al, "Protein-tyrosine phosphatase inhibition by a peptide containing the phosphotyrosyl mimetic, L-O-malonyltyrosine", *Biochem Biophys Res Commun* 209(3):817-822 (1995)2

Kole et al, "Specific inhibition of insulin receptor dephosphorylation by a synthetic dodecapeptide containing sulfotyrosyl residues as phosphotyrosyl mimetic", *Indian J Biochem Biophys* 34(1-2):50-55 (1997)

Latimer et al, "Stimulation of MAP kinase by v-raf transformation of fibroblasts fails to induce hyperphosphorylation of transfected tau", *FEBS Lett* 365:42-46 (1995)

Lawrence, J. C., Guinovart, J. J. & Larner, J. *J. Biol. Chem.* 252, 444-450 (1977)

Lovestone et al, *Curr Biol* 4:1077-1086 (1995)

Lucas J J, Hernandez F, Gomez-Ramos P, Moran M A, Hen R, J. A "Decreased nuclear beta-catenin, tahyperphosphorylation and neurodegeneration in GSK-3beta conditional transgenic mice". *EMBO J* 20:27-39 (2001)

Mandelkow E M, Drewes G, Biernat J, et al "Glycogen synthase kinase-3 and the Alzheimer-like state of microtubule-associated protein tau". *Febs Lett.* 314:315-21 (1992)

Mandelkow et al, "Tau as a marker for Alzheimer's disease", *Trends Biochem Sci.* 18(12):480-483 (1983)

Manji et al, "Lithium at 50: have the neuroprotective effects of this unique cation been overlooked?", *Biol Psychiatry* 46(7):929-940 (1999)

Manji H K and Lenox R H "Signaling: cellular insights into the pathophysiology of bipolar disorder" *Biol. Psych.* 48:518-30 (2001)

Mauvais-Jarvis, F., Ueki, K., Fruman, D. A., Hirshman, M. F., Sakamoto, K., Goodyear, L. J., Iannacone, M., Accili, D., Cantley, L. C. & Kahn, C. R. *J. Clin. Invest.* 109, 141-9 (2002)

McKinsey et al, "Phosphorylation of the PEST domain of IkappaBbeta regulates the function of NF-kappaB/IkappaB-beta complexes", *J Biol Chem* 272(36):22377-22380 (1997)

Merrifield et al, *J Am Chem Soc* 85:2149 (1964)

Mikol et al, "The crystal structures of the SH2 domain of p56lck complexed with two phosphonopeptides suggest a gated peptide binding site", *J Mol Biol* 246(2):344-355 (1995)

Miller J R and Moon R T "Signal transduction through beta-catenin and specofocation of cell fate during embryogenesis" *Genes & development* 10:2527-39 (1996)

Morfini, G., Szebenyi, G., Elluru, R., Ratner, N. & Brady, S. T. *EMBO J.* 21, 281-93 (2002)

Morrison et al, *Organic Chemistry*, 6th Ed. (Prentice Hall, 1992)

Mulot et al, "Phosphorylation of tau by glycogen synthase kinase-3 beta in vitro produces species with similar electrophoretic and immunogenic properties to PHF-tau from Alzheimer's disease brain", *Biochem Soc Trans* 23(1):45S (1995)

Myers et al, "RS-1 activates phosphatidylinositol 3'-kinase by associating with src homology 2 domains of p85d", *Proc Natl Acad Sci USA* 89(21):10350-10354 (1992)

Nicolaou et al, "Design and synthesis of a peptidomimetic employing β-D-glucose for scaffolding" in *Peptides*, Rivier and Marshall (eds) ESCOM (1990)

Nikoulina et al, "Potential role of glycogen synthase kinase-3 in skeletal muscle insulin resistance of type 2 diabetes", *Diabetes* 49(2):263-271 (2000)

Nonaka et al., *Proc. Natl. Acad. Sci. USA*, 95:2642-2647 (1998)

Otaka et al, *Chem Commun* (12):1081-1082 (2000)

Otaka et al, *Tetrahedron Lett* 36(6):927-30 (1995)

Pap M, Cooper G "Role of glycogen synthase kinase-3 in the phosphatidylinositol 3-Kinase/Akt cell survival pathway". *J. Biol. Chem.* 273:19929-32 (1998)

Peifer M and Polakis P "Wnt signaling in oncogensis and embryogenesis—a look outside the nucleus" *Science* 287:1606-9 (2000)

Porsolt R D, Le Pichon M and Jalfre M "Depression: a new animal model sensitive to antidepressant treatments" *Nature* 266:730-2 (1977)

Rich D H, in *Protease Inhibitors*, Barrett and Selveson (eds) Elsevier (1986)

Ricort, J. M., Tanti, J. F., Van Obberghen, E. & Le Marchand-Brustel, Y. *Eur. J. Biochem.* 239, 17-22 (1996)

Rojas, M., Yao, S. & Lin, Y. Z. *J. Biol. Chem.* 271, 27456-61 (1996)

Roller et al, "Potent inhibition of protein-tyrosine phosphatase-1B using the phosphotyrosyl mimetic fluoro-O-malonyl tyrosine (FOMT)", *Bioorg Med Chem Lett* 8(16):2149-2150 (1998)

Sakanaka C, Weiss J B and Williams L T "Bridging of beta-catenin and glycogen synthase kinase-3 beta by axin and inhibition of beta-catenin mediated transcription" *Proc Natl Acad Sci USA* 95:3020-3 (1998)

Sakaue, H., Ogawa, W., Takata M, Kuroda S, Kotani K, Matsumoto M, Sakaue M, Nishio S, Ueno, H. & Kasuga, M. K. *Mol. Endocrin.* 10, 1552-62 (1997)

Sambrook et al, *Molecular Cloning: A Laboratory Manual*, 2nd Ed. (Cold Spring Harbor Press, 1989)

Schiller et al, *Int J Pent Prot Res* 25:171 (1985)

Senel, S., Kremer, M., Nagy, K. & Squier, C. *Curr. Pharm. Biotechnol.* 2, 175-186 (2001)

Shapiro et al, "Combined Fmoc-Alloc strategy for a general SPPS of phosphoserine peptides; preparation of phosphorylation-dependent tau antisera", *Bioorg Med Chem* 5(1):147-56 (1997)

Sherman et al, *J Am Chem Soc* 112:433 (1990)

Shulman et al, "Quantitation of muscle glycogen synthesis in normal subjects and subjects with non-insulin-dependent diabetes by 13C nuclear magnetic resonance spectroscopy", *N Engl J Med* 322(4):223-228 (1990)

Stambolic V, Ruel L, Woodgett J R "Lithium inhibits glycogen synthase kinase-3 activity and mimics wingless signalling in intact cells". *Curr. Biol.* 6:1664-1668 (1996).

Surwit, R. S., Kuhn, C. M., Cochrane, C., McCubbin, J. A. & Feinglos, M. N. *Diabetes* 37, 1163-67 (1988)

Ter Haar et al., "Structure of GSK-3 beta reveals a primed phosphorylation mechanism", *Nat. Struct. Biol.* 8(7):593-6 (2001)

Thomas, J. A., Schlender, K. K. & Larner, J. *Anal. Biochem.* 25, 486-499 (1968)

Thomas, *J. Am. Geriatr. Soc.*, 43:1279-89 (1995)

Thorsett et al, "Dipeptide mimics. Conformationally restricted inhibitors of angiotensin-converting enzyme", *Biochem Biophys Res Commun* 111(1):166-171 (1983)

Tong N, Sanchez J F, Maggirwar S B, et al "Activation of glycogen synthase kinase 3 beta (GSK-3beta) by platelet activating factor mediates migration and cell death in cerebellar granule neurons". *Eur J Neurosci* 13:1913-22 (2001)

Ueki, K., Yballe, C. M., Brachmann, S. M., Vicent, D., Watt, J. M., Kahn, C. R. & Cantley, L. C. *Proc. Natl. Acad. Sci. USA* 99, 419-24 (2002)

Veber et al, "Conformationally restricted bicyclic analogs of somatostatin", *Proc Natl Acad Sci USA* 75(6):2636-2640 (1978)

Wang, Y. & Roach, P. J. *J. Biol. Chem.* 268, 23876-23880 (1993)

Wiemann et al, *Tetrahedron* 56:1331-1337 (2000)

Woodgett, J. R. & Cohen, P. *Biochim. Biophys. Acta.* 788, 339-47 (1984)

Woodgett, J. R. *Sci. STKE* 100, RE12 (2001)

Ye et al, "L-O-(2-malonyl)tyrosine: a new phosphotyrosyl mimetic for the preparation of Src homology 2 domain inhibitory peptides", *J Med Chem* 38(21):4270-4275 (1995)

Yost C, Torres M, Miller J, Huang E, Kimelman D and Moon R "The axis-inducing activity, stability and subcellular distribution of beta-catenin is regulated in *Xenopus* embryos by glycogen synthase kinase 3" *Genes* 10:1443-1454 (1996)

Zasloff, M. *Nature* 415, 389-95 (2002)

Zhang, W., Depaoli-Roach, A. A. & Roach, P. J. *Arch. Biochem. Biophys.* 304, 219-25 (1993)

Zhang, Z. H., Johnson, J. A., Chen, L., El-Sherif, N., Mochly-Rosen, D. & Boutjdir, M. *Circ. Res.* 80, 720-9 (1997)

What is claimed is:

1. A compound comprising a negatively charged group and at least one amino moiety-containing group, the compound having a general formula II:

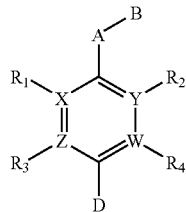

Formula II wherein:
X, Y, Z and W are each a carbon atom;
A is an unsubstituted alkyl;
B is phosphate;
D in Formula II is selected from the group consisting of hydrogen, alkyl, $C_1$ to $C_6$ substituted alkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonamide, carbonyl, ketoester, thiocarbonyl, ester, ether, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanyloalkyl, guanidino, guanidinoalkyl, amino, hydrazine, aminoalkyl and a hydrophobic moiety; and
$R_1$, $R_2$, $R_3$ and $R_4$ are each independently selected from the group consisting of said amino moiety-containing group, hydrogen, a lone pair of electrons, alkyl, trihaloalkyl, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azo, sulfonamide, carbonyl, ketoester, thiocarbonyl, ester, ether, thioether, thiocarbamate, urea, thiourea, O-carbamyl, N-carbamyl, O-thiocarbamyl, N-thiocarbamyl, C-amido, N-amido, C-carboxy, O-carboxy, sulfonamido, trihalomethanesulfonamido, guanyl, guanyloalkyl, guanidino, guanidinoalkyl, amino, aminoalkyl, hydrazine and an ammonium ion,
or a pharmaceutically acceptable salt thereof,
provided that at least one of $R_3$ and $R_4$ is an amino moiety-containing group selected from the group consisting of guanidino, guanidinoalkyl, amino, aminoalkyl, guanyl, guanyloalkyl and any combination thereof.

2. The compound of claim 1, wherein said amino moiety-containing group comprises at least one positively charged group.

3. The compound of claim 2, wherein said at least one positively charged group is selected from the group consisting of ammonium ion and guanidinium ion.

4. The compound of claim 2, wherein said at least one positively charged group has a chemical structure derived from a side chain of a positively charged amino acid.

5. The compound of claim 1, wherein at least two of $R_1$, $R_2$, $R_3$ and $R_4$ are said amino-moiety containing groups.

6. The compound of claim 1, wherein said D in Formula II is a hydrophobic moiety.

7. The compound of claim 1, wherein at least one of $R_3$ and $R_4$ is selected from the group consisting of guanidino and guanidinoalkyl.

8. The compound of claim 1, wherein each of $R_3$ and $R_4$ is selected from the group consisting of guanidino and guanidinoalkyl.

9. A pharmaceutical composition comprising, as an active ingredient, the compound of claim 1 and a pharmaceutically acceptable carrier.

10. The pharmaceutical composition of claim 9, packaged in a packaging material and identified in print, on or in said packaging material, for use in the treatment of a biological condition associated with GSK-3 activity.

11. The pharmaceutical composition of claim 9, further comprising at least one additional active ingredient that is capable of modulating an activity of GSK-3.

12. A method of inhibiting a phosphorylation activity and/or an autophosphorylation activity of GSK-3, the method comprising contacting cells expressing GSK-3 with an inhibitory effective amount of the compound of claim 1.

13. The method of claim 12, wherein inhibiting said activity of a GSK-3 comprises diminishing a binding of a substrate to a catalytic domain of a GSK-3.

14. The method of claim 12, further comprising contacting said cells with at least one an additional active ingredient, said additional active ingredient being capable of modulating an activity of GSK-3.

15. A method of potentiating insulin signaling, the method comprising contacting insulin responsive cells with an effective amount of the compound of claim 1.

16. The method of claim 15, further comprising contacting said cells with insulin.

17. The compound of claim 1, being selected from the group consisting of:
3,5-bis(2-aminoethyl)benzyl phosphate (GSC-21);
3-(guanidinomethyl)benzyl phosphate (GSC-5);
3-guanidinobenzyl phosphate (GSC-4);
3-(guanidinoethyl)benzyl phosphate (GSC-6);
3,5-bisguanidinobenzyl phosphate (GSC-7);
3,5-bis(guanidinomethyl)benzyl phosphate (GSC-8); and
3,5-bis(guanidinoethyl)benzyl phosphate (GSC-9).

18. A method of inhibiting a phosphorylation activity and/or an autophosphorylation activity of GSK-3, the method comprising contacting cells expressing GSK-3 with an inhibitory effective amount of the compound of claim 17.

19. The method of claim 18, wherein inhibiting said activity of a GSK-3 comprises diminishing a binding of a substrate to a catalytic domain of a GSK-3.

20. The method of claim 18, further comprising contacting said cells with at least one an additional active ingredient, said additional active ingredient being capable of modulating an activity of GSK-3.

21. A method of potentiating insulin signaling, the method comprising contacting insulin responsive cells with an effective amount of the compound of claim 17.

22. The method of claim 21, further comprising contacting said cells with insulin.

23. A method of treating a biological condition selected from the group consisting of non-insulin dependent diabetes mellitus, and an insulin-dependent condition, the method comprising administering to a subject in need thereof a therapeutically effective amount of the compound of claim 17.

24. The method of claim 23, further comprising co-administering to said subject at least one additional active ingredient, said at least one additional active ingredient being capable of modulating an activity of GSK-3.

* * * * *

SEQUENCE LISTING

<160> NUMBER OF SEQ ID NOS: 4

<210> SEQ ID NO 1
<211> LENGTH: 5
<212> TYPE: PRT
<213> ORGANISM: Artificial sequence
<220> FEATURE:
<223> OTHER INFORMATION: GSK-3 recognition motif consensus
<220> FEATURE:
<221> NAME/KEY: misc_feature
<222> LOCATION: (1)..(1)
<223> OTHER INFORMATION: Ser or Thr
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Phosphorylated Ser or Thr

<400> SEQUENCE: 1

Xaa Xaa Xaa Xaa Xaa
1               5

<210> SEQ ID NO 2
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: PHOSPHORYLATION

<400> SEQUENCE: 2

Ile Leu Ser Arg Arg Pro Ser Tyr Arg
1               5

<210> SEQ ID NO 3
<211> LENGTH: 9
<212> TYPE: PRT
<213> ORGANISM: Artificial sequence
<220> FEATURE:
<223> OTHER INFORMATION: Synthetic peptide

<400> SEQUENCE: 3

Ile Leu Ser Arg Arg Pro Ser Tyr Arg
1               5

<210> SEQ ID NO 4
<211> LENGTH: 9
<212> TYPE: PRT
<213> ORGANISM: Artificial sequence
<220> FEATURE:
<223> OTHER INFORMATION: Synthetic peptide

<400> SEQUENCE: 4

Ile Leu Ser Arg Arg Pro Glu Tyr Arg
1               5